（12）United States Patent
Edwards et al.

(10) Patent No.: US 11,172,690 B2
(45) Date of Patent: Nov. 16, 2021

(54) ENCLOSING MATERIALS IN NATURAL TRANSPORT SYSTEMS

(71) Applicant: INCREDIBLE FOODS, INC., Boston, MA (US)

(72) Inventors: David A. Edwards, Boston, MA (US); Laurent Robert Adrien Milon, Paris (FR); Heloise Vilaseca, Barcelona (ES)

(73) Assignee: Incredible Foods, Inc., Boston, MA (US)

( * ) Notice: Subject to any disclaimer, the term of this patent is extended or adjusted under 35 U.S.C. 154(b) by 0 days.

(21) Appl. No.: 16/259,110

(22) Filed: Jan. 28, 2019

(65) Prior Publication Data

US 2019/0223466 A1 Jul. 25, 2019

Related U.S. Application Data

(63) Continuation of application No. 14/374,069, filed as application No. PCT/US2013/023500 on Jan. 28, 2013, now abandoned.

(60) Provisional application No. 61/591,225, filed on Jan. 26, 2012, provisional application No. 61/591,054, filed on Jan. 26, 2012, provisional application No.
(Continued)

(51) Int. Cl.
*A23G 9/24* (2006.01)
*A23P 10/30* (2016.01)
*A23P 20/10* (2016.01)
*A23L 19/00* (2016.01)
*A61K 9/48* (2006.01)

(52) U.S. Cl.
CPC .............. *A23G 9/245* (2013.01); *A23L 19/01* (2016.08); *A23L 19/05* (2016.08); *A23P 10/30* (2016.08); *A23P 20/105* (2016.08); *A61K 9/4808* (2013.01)

(58) Field of Classification Search
CPC .......... A23G 3/20; A23G 3/2007; A23G 3/22; A23G 3/32; A23G 3/34; A23G 3/54; A23G 9/245; A23G 4/18; A23G 4/00; A23L 19/05; A23L 19/01; A23P 20/105; A23P 10/30; A61K 9/4808
See application file for complete search history.

(56) References Cited

U.S. PATENT DOCUMENTS 4,822,622 A 4/1989 Dokuzovic et al.
4,828,845 A 5/1989 Zamudio-Tena et al.
(Continued)

FOREIGN PATENT DOCUMENTS

CA 2703807 A1 11/2011
EP 0273856 A1 7/1988
(Continued)

OTHER PUBLICATIONS

Burey et al. "Hydrocolloid Gel Particles: Formation, Characterization, and Application Abstract." May 2, 2008. Critical Reviews in Food Science and Nutrition. vol. 48. Issue 5. (Year: 2008).*
(Continued)

*Primary Examiner* — Ericson M Lachica
(74) *Attorney, Agent, or Firm* — Hogan Lovells US LLP

(57) ABSTRACT

An edible composition, particularly an edible transport system, comprising an edible substance and a cross-linked matrix encapsulating the edible substance, the cross-linked matrix comprising (1) at least one edible polymer and edible particles or (2) a plurality of edible polymers.

10 Claims, 16 Drawing Sheets

ALGINIC ACID

SODIUM ALGINATE

STRUCTURE OF ALGINATE POLYMER
-(M)ₘ-(G)ₙ - (M: MANNURONATE; G: GULURONATE)

Related U.S. Application Data

61/591,233, filed on Jan. 26, 2012, provisional application No. 61/591,262, filed on Jan. 26, 2012, provisional application No. 61/601,866, filed on Feb. 22, 2012, provisional application No. 61/601,852, filed on Feb. 22, 2012, provisional application No. 61/647,721, filed on May 16, 2012, provisional application No. 61/713,100, filed on Oct. 12, 2012, provisional application No. 61/713,063, filed on Oct. 12, 2012, provisional application No. 61/713,138, filed on Oct. 12, 2012.

(56) References Cited

U.S. PATENT DOCUMENTS

| | | | |
|---|---|---|---|
| 4,985,263 A | 1/1991 | Klug et al. | |
| 5,240,396 A * | 8/1993 | Bremyer | B29C 48/30 425/133.1 |
| 5,888,567 A * | 3/1999 | Daouse | A23G 9/285 425/133.1 |
| 6,338,863 B1 * | 1/2002 | Amiel | A23G 9/04 426/101 |
| 2004/0121051 A1 | 6/2004 | Fenn et al. | |
| 2006/0073190 A1 | 4/2006 | Carroll et al. | |
| 2006/0222745 A1 * | 10/2006 | Baumer | A23C 9/13 426/306 |
| 2007/0148285 A1 * | 6/2007 | Yang | A23G 3/54 426/5 |
| 2007/0160707 A1 * | 7/2007 | Garcia | A23G 3/0068 426/3 |
| 2007/0254071 A1 * | 11/2007 | Rosskam | A23G 9/44 426/95 |
| 2008/0063748 A1 | 3/2008 | Massey et al. | |
| 2008/0206426 A1 * | 8/2008 | Rousset | A23D 7/003 426/576 |
| 2009/0036844 A1 * | 2/2009 | Fristrup | A61J 1/1406 604/288.04 |
| 2009/0214729 A1 * | 8/2009 | Shimek | A23G 3/346 426/312 |
| 2011/0189109 A1 * | 8/2011 | Pilgaonkar | A23C 9/1544 424/49 |
| 2013/0316053 A1 * | 11/2013 | Rifkin | A23G 3/007 426/280 |
| 2015/0250203 A1 * | 9/2015 | Edwards | A23L 19/01 426/101 |

FOREIGN PATENT DOCUMENTS

| | | |
|---|---|---|
| JP | S6443152 A | 2/1989 |
| JP | H05244872 A | 9/1993 |
| JP | 2011-512818 A | 4/2001 |
| JP | 2005-522991 A | 8/2005 |
| JP | 2008-514235 A | 5/2008 |
| JP | 2009-532059 A | 9/2009 |
| JP | 2009-539719 A | 11/2009 |
| WO | 0151196 A | 7/2001 |
| WO | 2003/043659 A1 | 5/2003 |
| WO | 2004098318 A1 | 11/2004 |
| WO | 2006/039487 A2 | 4/2006 |
| WO | 2007114719 A1 | 10/2007 |
| WO | 2007/149276 A2 | 12/2007 |
| WO | 2009108769 A2 | 9/2009 |
| WO | 2011056904 A1 | 5/2011 |
| WO | 2011103594 A1 | 8/2011 |
| WO | 2011/117727 A1 | 9/2011 |
| WO | 2011/117738 A2 | 9/2011 |

OTHER PUBLICATIONS

International Search Report from corresponding PCT Application No. PCT/US2013/023500, dated Jul. 25, 2013, 6 pages.

* cited by examiner

ALGINIC ACID

SODIUM ALGINATE

STRUCTURE OF ALGINATE POLYMER
-(M)m-(G)n - (M: MANNURONATE; G: GULURONATE)

POLYMERIZATION OF SODIUM
ALGINATES VIA DIVALENT CATIONS
(e.g. $Ca^{2+}$) [USTL Lille]

WIKICELLS ARE EDIBLE CONTAINERS OF FOOD AND DRINKS THAT CAN BE PRODUCED AT MASS SCALE, ARE STABLE OVER EXTENDED PERIODS OF TIME, AND CAN BE DESIGNED BY CONSUMERS TO A PRACTICALLY UNLIMITED DEGREE.

(A)　　(B)　　(C)　　(D)　　(E)　　(F)

ENCLOSING MATERIALS IN NATURAL TRANSPORT SYSTEMS

RELATED APPLICATIONS

This application is a continuation of U.S. application Ser. No. 14/374,069, filed on Jul. 23, 2014, which is the U.S. National Stage of International Application No. PCT/US2013/023500, filed Jan. 28, 2013, published in English, which claims the benefit of U.S. Provisional Application No. 61/591,225, filed on Jan. 26, 2012, U.S. Provisional Application No. 61/591,054, filed on Jan. 26, 2012, U.S. Provisional Application No. 61/291,233, filed on Jan. 26, 2012, U.S. Provisional Application No. 61/591,262, filed on Jan. 26, 2012, U.S. Provisional Application No. 61/601,866, filed on Feb. 22, 2012, U.S. Provisional Application No. 61/601,852, filed on Feb. 22, 2012, U.S. Provisional Application No. 61/647,721, filed on May 16, 2012, U.S. Provisional Application No. 61/713,100, filed on Oct. 12, 2012, U.S. Provisional Application No. 61/713,063, filed on Oct. 12, 2012, and U.S. Provisional Application No. 61/713,138, filed on Oct. 12, 2012; the entire teachings of these applications are incorporated herein by reference.

TECHNICAL FIELD

This disclosure relates to vessels for encasing edible materials, and more particularly to edible and/or biodegradable vessels.

BACKGROUND

Mankind has filled, carried, and transported water, other liquids (as well as solids, emulsions, slurries, foams, etc.) and edible materials in vessels made of pottery, glass, plastics and other materials since prehistoric times. While the nature of these vessels has evolved with advances in material manufacture and design, the basic principle of a vessel in the form of a container with a surface that encloses the edible material, either partially or completely, and from which the edible material can be removed, emptying the vessel, which can be refilled or discarded, has essentially not varied. Users continue to fill and empty containers with water, other liquids, and edible materials for various practical purposes.

SUMMARY

In certain embodiments, an edible composition, particularly an edible transport system, comprises an edible substance and a cross-linked matrix encapsulating the edible substance, the cross-linked matrix comprising (1) at least one edible polymer and edible particles or (2) a plurality of edible polymers.

In certain embodiments of the edible composition the at least one edible polymer and the edible particles or the plurality of edible polymers are charge cross-linked by multivalent ions, including cross-linking interactions between the edible particles and edible polymer or plurality of edible polymers via bridges formed by the multivalent ions.

In some embodiments of the edible composition, the edible particles of the edible composition are one of the group consisting of a positively charged edible particle, a neutrally charged edible particle, a negatively charged edible particle, an amphipathic edible particle, a zwitterionic edible particle, and combinations thereof.

In some embodiments of the edible composition, the edible polymer is one of the group consisting of a positively charged edible polymer, a neutrally charged edible polymer, a negatively charged edible particle, an amphipathic edible polymer, a zwitterionic edible polymer, and combinations thereof.

In some embodiments of the edible composition, the edible particles comprise a second edible particle having a characteristic dimension of less than 75% (e.g., less than 50%, 25%, less than 10%, less than 5%, or less than 1% of) a characteristic dimension of the first edible particle.

In some embodiments of the edible composition, the matrix comprising the first and second edible particles has a lower mass loss rate than a similar edible composition without the first and second edible particles. In some embodiments of the edible composition, the first particles provide structural stability to the matrix.

In some embodiments of the edible composition, the polymer comprises a polysaccharide selected from the group consisting of a hydrocolloid, shellac, and fibers.

In some embodiments of the edible composition, the polymer comprises a hydrocolloid selected from the group consisting of an alginate, an agar, a starch, a gelatin, carrageenan, xanthan gum, gellan gum, galactomannan, gum arabic, a pectin, a milk protein, a cellulosic, a carboxymethylcellulosic, a methylcellulosic, gum tragacanth and karaya, xyloglucan, curdlan, a cereal β-glucan, soluble soybean polysaccharide, a bacterial cellulose, a microcrystalline cellulose, chitosan, inulin, an emulsifying polymer, konjac mannan/konjac glucomannan, a seed gum, and pullulan. In some embodiments, the hydrocolloid comprises an alginate selected from the group consisting of sodium alginate, ammonium alginate, potassium alginate, and propylene glycol alginate.

In some embodiments of the edible composition, the cross-linked matrix further comprises particles selected from the group comprising a hydrocolloid, shellac, fibers, bagasse, tapioca, chitosan, sugar derivatives, chocolate, seaweed, and combinations thereof, and wherein the particles comprise a compound different from the polymer compound.

In some embodiments of the edible composition, the edible particles comprise a size having a volume mean distribution between about 0.1 microns and about 1.0 microns, between about 0.1 microns and about 10.0 microns, between about 0.1 microns and about 100.0 microns, between about 0.1 microns and about 1.0 millimeters, between about 0.1 and about 3 millimeters. In certain embodiments, the edible particles are particles selected from the group consisting of particles of a food, particles of an energy supplement, particles of a dietary supplement, particles of a confection, particles of a nutraceutical, particles of a pharmaceutical, particles of a sleep aid compound, particles of a weight loss compound, particles of a powdered vegetable, particles of a flavoring agent, particles of a sweetener, particles of a metabolic intermediate of a pharmaceutical, particles of a metabolic by-product of a pharmaceutical, and combinations thereof.

In some embodiments of the edible composition, the edible substance comprises at least one of a powder, a gel, an emulsion, a foam, a solid, and combinations thereof.

In some embodiments of the edible composition, the edible substance is selected from the group consisting of fruit, vegetable, meat, a dairy product, a carbohydrate food product, a botanical, an energy supplement, a dietary supplement, a confection, a nutraceutical, a pharmaceutical, a sleep aid compound, a weight loss compound, a powdered vegetable, a flavoring agent, a sweetener, a powdered food product, and combinations thereof.

In some embodiments of the edible composition, the edible substance comprises a liquid, particularly wherein the liquid comprises at least one of water, an alcohol, a juice, an alcohol mixed drink, a coffee product, a tea product, a soft drink, an energy supplement product, a dietary supplement, a confection, and combinations thereof.

In some embodiments of the edible composition, the edible composition further comprises an outer shell enclosing the matrix, the shell being more structurally resilient than the matrix at room temperature. In some embodiments is an edible barrier layer between the matrix and the outer shell. In certain embodiments, the barrier layer reduces a force required to separate the matrix from the outer shell. In other embodiments the barrier layer limits the transfer of water out of the edible substance encapsulated in the matrix.

In some embodiments of the edible composition is a second cross-linked matrix encapsulating the cross-linked matrix, the second cross-linked matrix comprising (1) at least one edible polymer and edible particles or (2) a plurality of edible polymers. In some embodiments is a particle layer arranged between each cross-linked matrix. In certain embodiments the particle layer comprises particles selected from the group consisting of particles of a food, particles of an energy supplement, particles of a dietary supplement, particles of a confection, particles of a nutraceutical, particles of a pharmaceutical, particles of a sleep aid compound, particles of a weight loss compound, particles of a powdered vegetable, particles of a flavoring agent, particles of a sweetener, particles of a metabolic intermediate of a pharmaceutical, particles of a metabolic by-product of a pharmaceutical, and combinations thereof.

In one embodiment of the edible composition is a method of preparing an edible composition, comprising the steps of providing an edible substance; encapsulating the edible substance in a cross-linked matrix comprising (1) at least one edible polymer and edible particles or (2) a plurality of edible polymers.

In some embodiments of method for preparing the edible composition, the edible polymer and the edible particles or the plurality of edible polymers are charge cross-linked by multivalent ions, including cross-linking interactions between the edible particles and edible polymer or plurality of edible polymers via bridges formed by the multivalent ions.

In some embodiments of method for preparing the edible composition, the edible particles are one of the group consisting of a positively charged edible particle, a neutrally charged edible particle, a negatively charged edible particle, an amphipathic edible particle, a zwitterionic edible particle, and combinations thereof.

In some embodiments of method for preparing the edible composition, the edible polymer is one of the group consisting of a positively charged edible polymer, a neutrally charged edible polymer, a negatively charged edible particle, an amphipathic edible polymer, a zwitterionic edible polymer, and combinations thereof.

In some embodiments of method for preparing the edible composition, the edible particles comprise a second edible particle having a characteristic dimension of less than 75% (e.g., less than 50%, 25%, less than 10%, less than 5%, or less than 1% of) a characteristic dimension of the first edible particle.

In some embodiments of method for preparing the edible composition, the matrix comprising the first and second edible particles has a lower mass loss rate than a similar edible composition without the first and second edible particles.

In some embodiments of method for preparing the edible composition, the first particles provide structural stability to the matrix.

In some embodiments of method for preparing the edible composition, the polymer comprises a polysaccharide selected from the group consisting of a hydrocolloid, shellac, and fibers. In some embodiments, the polymer comprises a hydrocolloid selected from the group consisting of an alginate, an agar, a starch, a gelatin, carrageenan, xanthan gum, gellan gum, galactomannan, gum arabic, a pectin, a milk protein, a cellulosic, a carboxymethylcellulosic, a methylcellulosic, gum tragacanth and karaya, xyloglucan, curdlan, a cereal β-glucan, soluble soybean polysaccharide, a bacterial cellulose, a microcrystalline cellulose, chitosan, inulin, an emulsifying polymer, konjac mannan/konjac glucomannan, a seed gum, and pullulan.

In some embodiments of method for preparing the edible composition, the hydrocolloid comprises an alginate selected from the group consisting of sodium alginate, ammonium alginate, potassium alginate, and propylene glycol alginate.

In some embodiments of method for preparing the edible composition, the cross-linked matrix further comprises particles selected from the group comprising particles of a hydrocolloid, particles of shellac, fibers, particles of bagasse, particles of tapioca, particles of chitosan, particles of sugar derivatives, particles of chocolate, particles of seaweed, and combinations thereof, and wherein the particles comprise a compound different from the polymer compound.

In some embodiments of method for preparing the edible composition, the edible particles comprise a size having a volume mean distribution between about 0.1 microns and about 1.0 microns, between about 0.1 microns and about 10.0 microns, between about 0.1 microns and about 100.0 microns, between about 0.1 microns and about 1.0 millimeters, between about 0.1 and about 3 millimeters.

In some embodiments of method for preparing the edible composition, the edible particles are particles selected from the group consisting of particles of a food, particles of an energy supplement, particles of a dietary supplement, particles of a confection, particles of a nutraceutical, particles of a pharmaceutical, particles of a sleep aid compound, particles of a weight loss compound, particles of a powdered vegetable, particles of a flavoring agent, particles of a sweetener, particles of a metabolic intermediate of a pharmaceutical, particles of a metabolic by-product of a pharmaceutical, and combinations thereof.

In some embodiments of method for preparing the edible composition, the edible substance comprises at least one of a powder, a gel, an emulsion, a foam, a solid, and combinations thereof. In certain embodiments, the edible substance is selected from the group consisting of fruit, vegetable, meat, a dairy product, a carbohydrate food product, a botanical, an energy supplement, a dietary supplement, a confection, a nutraceutical, a pharmaceutical, a sleep aid compound, a weight loss compound, a powdered vegetable, a flavoring agent, a sweetener, a powdered food product, and combinations thereof.

In some embodiments of method for preparing the edible composition, the edible substance comprises a liquid, particularly wherein the liquid comprises at least one of water, an alcohol, a juice, an alcohol mixed drink, a coffee product, a tea product, a soft drink, an energy supplement product, a dietary supplement, a confection, and combinations thereof.

In some embodiments of method for preparing the edible composition is an outer shell enclosing the matrix, the shell being more structurally resilient than the matrix at room temperature.

In some embodiments of method for preparing the edible composition is an edible barrier layer between the matrix and the outer shell. In some embodiments of method for preparing the edible composition, the barrier layer reduces a force required to separate the matrix from the outer shell. In some embodiments of method for preparing the edible composition, the barrier layer limits the transfer of a liquid out of the edible substance encapsulated in the matrix.

In some embodiments of method for preparing the edible composition is a second cross-linked matrix encapsulating the cross-linked matrix, the second cross-linked matrix comprising (1) at least one edible polymer and edible particles or (2) a plurality of edible polymers. In some embodiment, a particle layer is arranged between each edible matrix. In certain embodiments the particle layer is comprised of particles selected from the group consisting of particles of a food, particles of an energy supplement, particles of a dietary supplement, particles of a confection, particles of a nutraceutical, particles of a pharmaceutical, particles of a sleep aid compound, particles of a weight loss compound, particles of a powdered vegetable, particles of a flavoring agent, particles of a sweetener, particles of a metabolic intermediate of a pharmaceutical, particles of a metabolic by-product of a pharmaceutical, and combinations thereof.

In one embodiment is an ingestible article comprising an edible fruit material comprising a fruit-derived material; and an exterior surface material disposed on the fruit material, wherein the exterior surface material comprises an edible or biodegradable component, wherein the exterior surface material is substantially moldable, wherein the ingestible article has a conformation substantially similar to the fruit from which the fruit-derived material is derived.

In some embodiments of an ingestible article, the fruit-derived material is liquid or semi-solid.

In some embodiments of an ingestible article, the fruit-derived material comprises water.

In some embodiments of an ingestible article, the fruit-derived material comprises at least one nutritive compound not substantially present in the fruit from which the fruit-derived material is derived.

In some embodiments of the ingestible article, the at least one nutritive compound comprises a vitamin or a mineral, a protein or peptide, a dietary fiber material, a lipid, or a combination thereof. In some embodiments is an odorant, a colorant, a texturant, a flavoring agent, or a combination thereof.

In certain embodiments the ingestible article has at least as much nutritional content as is present in the fruit from which the fruit-derived material is derived.

In certain embodiments of the ingestible article, the exterior surface material comprises a polymeric material.

In certain embodiments of the ingestible article, the exterior surface material is, in part, formed using a solution containing multivalent cations.

In certain embodiments, the ingestible article has at least about 50% fruit-derived material on a weight to weight basis.

In certain embodiments, the exterior surface material comprises an insertion region suitable for insertion of an evacuation means. In certain embodiments the evacuation means comprises a straw.

In certain embodiments of the ingestible article, the exterior surface material is capable of maintaining the moisture content of the fruit material.

In one embodiment is a method of preparing a reconstituted fruit object, comprising the steps of providing a fruit-derived material having at least one exterior surface, and contacting the fruit-derived material with an exterior surface material under conditions such that the exterior surface material is disposed on the exterior surface of the fruit-derived material.

In some embodiments of the method of preparing a reconstituted fruit object, the exterior surface material is edible or biodegradable.

In some embodiments of the method of preparing a reconstituted fruit object, the exterior surface material is moldable such that the reconstituted fruit object has a conformation substantially similar to the fruit from which the fruit-derived material is derived.

In some embodiments of the method of preparing a reconstituted fruit object, the exterior surface material comprises an odorant, colorant, texturant, flavoring agent, or combination thereof.

In some embodiments of the method of preparing a reconstituted fruit object, the fruit-derived material is semi-solid or solid when contacted with the exterior surface material.

In one embodiment is a system for enclosing a substance in an edible membrane, the system comprising: a first station having a first inlet that receives an edible or potable substance; a first cage that is connected to a first movement device, the movement device configured to raise and lower the cage into a first fluid bath; and a first outlet that receives the edible or potable substance from the first cage, the first outlet being arranged at a generally lower vertical position than the first inlet relative to the first fluid bath; and a second station having: a second inlet that receives the edible or potable substance from the first outlet; a second cage that is connected to a second movement device, the movement device configured to raise and lower the cage into a second fluid bath; and a second outlet that receives the edible or potable substance from the second cage, the second outlet being arranged at a generally lower vertical position than the second inlet relative to the second fluid bath.

In some embodiments is a system for enclosing a substance in an edible membrane, the first movement device comprises a piston.

In some embodiments is a system for enclosing a substance in an edible membrane is a chute extending between the first outlet and the second inlet. In another embodiment is a third station having: a third inlet that receives an edible or potable substance; a third cage that is connected to a third movement device, the third movement device configured to raise and lower the cage into a third fluid bath; and a third outlet that receives the edible or potable substance from the third cage, the third outlet being arranged at a generally lower vertical position than the third inlet relative to the third fluid bath.

In some embodiments the second station is configured to contain liquid nitrogen.

In some embodiments is a system for enclosing a substance in an edible membrane the first cage comprise members at least partially defining an interior space, the members defining apertures through which fluid can flow as the first cage is raised out of and lowered into the first fluid bath.

In some embodiments is a system for enclosing a substance in an edible membrane the members at least partially defining the interior space comprise perforated metal sheets.

In one embodiment for enclosing a substance in an edible membrane is a method comprising: lowering an edible or potable substance into a first liquid bath and coating the edible or potable substance with a first membrane that is substantially impermeable to the edible or potable substance at room temperature; raising the cooled edible or potable substance from the first liquid bath; lowering the cooled edible or potable substance in the first membrane into a second liquid bath and coating the cooled edible or potable substance in the first membrane with a second membrane that is structurally stable at room temperature; and raising the cooled edible or potable substance in the first and second membranes from the second liquid bath.

In some embodiments for a method of enclosing a substance in an edible membrane, the edible or potable substance is in liquid nitrogen.

In some embodiments for a method of enclosing a substance in an edible membrane is the step of immersing the edible or potable substance in liquid nitrogen occuring after raising the cooled edible or potable substance from the first liquid bath and before lowering the edible or potable substance into the second liquid bath.

In some embodiments for a method of enclosing a substance in an edible membrane, lowering the edible or potable substance into the second liquid bath comprises lowering the edible or potable substance into an alginate solution.

In some embodiments for a method of enclosing a substance in an edible membrane, lowering the edible or potable substance into the first liquid bath comprises lowering the edible or potable substance into a gelling solution. Other embodiments comprise lowering the edible or potable substance into a gelling solution after lowering the edible or potable substance into the alginate solution.

In some embodiments the method of enclosing a substance in an edible membrane, comprises freezing the edible or potable substance before the lowering the edible or potable substance into the first liquid bath.

In one embodiment is a system for enclosing a substance in an edible membrane, the system comprising: a first station having a reservoir, the first station operable to lower a portion of the substance into the reservoir of the first station and then raise the portion of the substance out of the reservoir of the first station; a second station having a reservoir, the second station operable to lower the portion of the substance into the reservoir of the second station and then raise the portion of the substance out of the reservoir of the second station; and a mechanism connecting the first station and the second station operable to transfer the portion of the substance between the first station and the second station.

In some embodiments for a system for enclosing a substance in an edible membrane, the first station comprises a cage moveable between a first position in which the cage is disposed in the reservoir of the first station and a second position in which the cage is disposed at least partially outside the reservoir of the first station. In some embodiments, the first station comprises a piston operable to position the cage.

In some embodiments for a system for enclosing a substance in an edible membrane, the cage comprise members at least partially defining an interior space, the members defining apertures through which fluid can flow as the cage is raised out of and lowered into the reservoir of the first station.

In some embodiments for a system for enclosing a substance in an edible membrane, the mechanism connecting the first station and the second station comprises a slanted chute extending between the first station and the second station.

In some embodiments for a system for enclosing a substance in an edible membrane, the reservoir of the second station is configured to contain liquid nitrogen.

Figure 1:
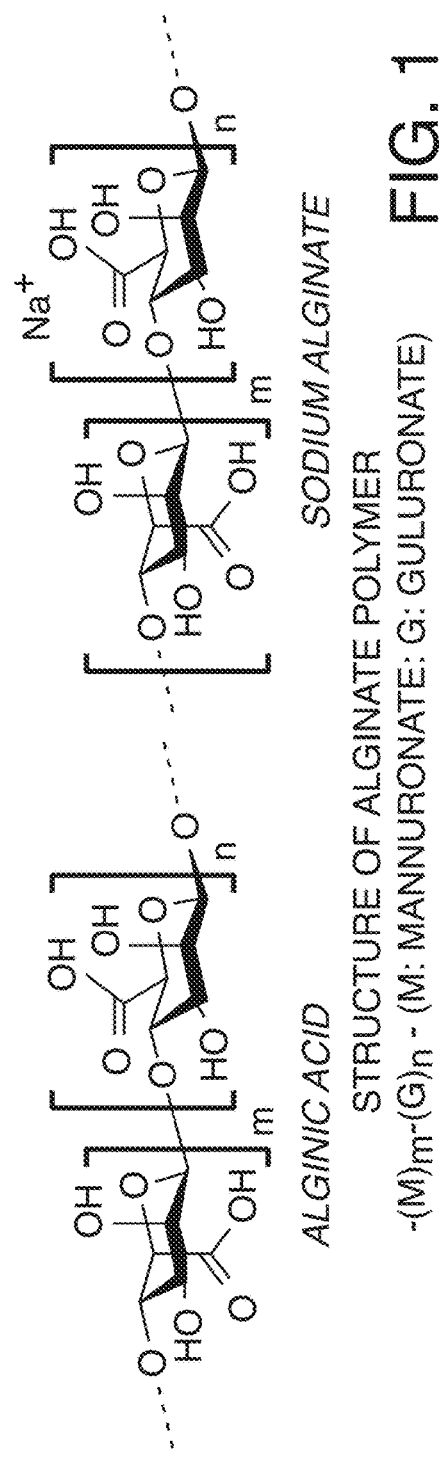
FIG. 1 shows the chemical structure of an alginate polymer $-(M)_m-(G)_n-$(M: mannuronate; G: guluronate).

FIGS. 17*a-d* illustrate a process for arranging a barrier layer around a transport system and enclosing the transport system and barrier layer within a shell.

FIG. 18 illustrates another example of a transport system arranged within an edible shell.

FIG. 19 is a perspective view of a system for coating objects to form natural transport systems.

FIG. 20 is a front view of another system for coating objects to form natural transport systems.

FIGS. 21*a-c* illustrate a multi-membrane packaging of a strawberry product.

DETAILED DESCRIPTION

Transport systems contain and protect ingestible/edible substances, such as food, within edible or biodegradable membranes (matrix or matrices) and/or shells. The edible membranes/shells of transport systems can be formed from various substances allowing different compositions to be transported and consumed. As used herein, the terms "membrane(s)," "matrix" or "matrices," and "shell(s)" may refer to similar or different materials or kinds of materials, depending on the type of object, how many barrier layers of any sort it may have, or the properties and contents of any such barrier layers. Thus, for some embodiments, the terms can be used interchangeably. In certain embodiments, membranes and/or membranes and shells are edible, providing nutritious benefits as well as reducing concerns about littering and waste. Embodiments of transport system described herein can have, e.g., varying shell or membrane thickness, one or more of a variety of chemical constituents, varying numbers of membranes, various consumable payloads, various shapes, and are constructed from various shell/membrane properties to provide a variety of flavors and textures and membrane characteristics. Embodiments of the transport systems can be made at large scale, using, for example, injection techniques, spray and spray drying techniques, fluidized-bed and other technologies. See, for example, PCT application WO 2011/103594, hereby incorporated in its entirety.

Edible materials are generally solid, semi-solid or liquid in form, are capable of providing nutrition when consumed, and are typically provided in a form suitable for ingestion. Edible materials can be derived from many sources including plants and animals, particularly those generated by agriculture, or from artificial production methods including chemical synthesis. Edible refers to any substance that can provide for an organism's (e.g., a human or other mammal) nutritional needs or sensory desires, typically when consumed orally, and is usually non-toxic when properly consumed. Biodegradable refers to capable of being decomposed by actions of biological agents such as microorganisms, or by non-biological effects such as environmental exposure. Liquid refers to having a consistency like that of water or oil, that is to say, flowing freely but of constant volume. Solid refers to being characterized by structural rigidity and resistance to changes of shape and volume. Semi-solid refers to having a rigidity intermediate between a solid and a liquid. Viscosity refers to a fluid's resistance to flow, wherein gel-like liquids have higher viscosity—for example, honey is more viscous than water. Foam refers to a mass of small bubbles formed on or in a substrate, typically a liquid, but also includes ice cream, frozen yogurts and gellato. Frozen refers to a phase change in which a liquid is turned into a solid when its temperature is lowered beyond its freezing point. In some embodiments, the food material may be liquid, partially liquid, viscous, partially or fully solid, or contains several states of matter having different degrees of liquidity or solidness.

Ingestible substances include those that are edible or potable such as, for example, juice, chocolate, various medicines, and various other solids, liquids, slurries, emulsions, foams, etc. For example, foods, particularly fruits and vegetables, such as berries, plants, and beans, are provided in various states of matter: liquid, semi-solid, solid, and frozen. They can be mixed with each other and optionally one or more nutrients and additives in varying proportions can be added to the mixture to produce a large variety of novel food objects. Their texture and consistency can be manipulated by physical, chemical or biochemical means.

Membranes and shells of transport systems may be made by using any one of many edible and/or biodegradable polymers. FIG. 1 illustrates alginate (alginic acid) as an example of a polymer that can be used in forming a membrane of transport systems. Alginate is an anionic, polymeric polysaccharide, widely present in the cell walls of brown algae. It is a copolymer -$(M)_m$-$(G)_n$- segments composed of mannuronate M (manurronic acid) and guluronate G (guluronic acid) monomeric subunits. The values of m and n, the ratio m/n, and the space distribution between M and G (i.e. presence of consecutive G-subunits and M-subunits, or randomly organized subunits) all play key roles in the chemical and physical properties of the final membrane.

Figure 2:
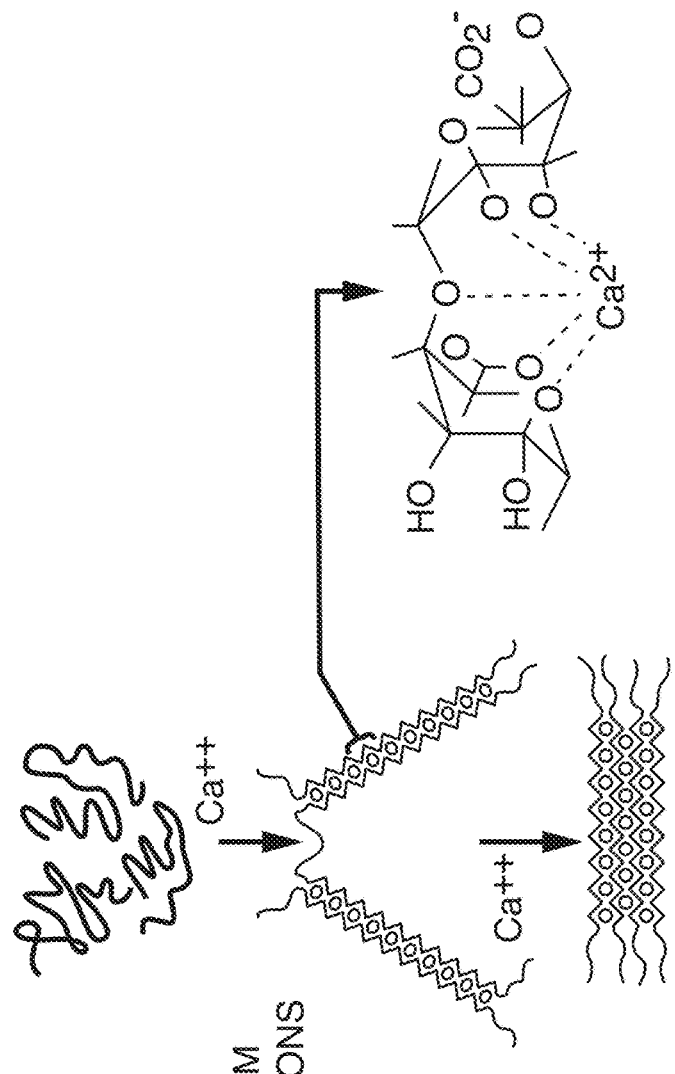
FIG. 2 illustrates polymerization of sodium alginates via divalent cations (e.g., $Ca^{2+}$).

Alginates have been applied to pharmaceutical preparations, impression-making materials (e.g., in dentistry and in prosthetics manufacturing), and in the food industry. Sodium alginates also have found application in restaurants, e.g., to create spheres of liquid surrounded by a thin jelly membrane. Modern chefs such as Faran Adria have used sodium alginates to create "melon caviar," "false fish eggs," etc., by adding sodium alginates into a liquid (e.g., melon juice), then dropping the preparation in a calcium bath (calcium lactate or calcium chloride). Beyond their biocompatibility to human use, polymers such as alginate have the capacity to easily form a gel. To induce rapid gelation by electrostatic cross-linking, the naturally present $Na^+$ ions are removed and replaced by divalent cations (e.g., $Ca^{2+}$ or another multi-valent cation such as $Mg^{2+}$; FIG. 2).

Our approach involves forming encapsulated vessels (transport systems) that use various particles, particulates and polymers, in combination or separately, to create desired properties of strength, stability, permeability, edibility and biodegradability for the transport systems to be easily moved and consumed. As used herein, the terms particle(s) and particulate(s) are used interchangeably.

In some embodiments, a consumable, edible product is encased in a polysaccharide membrane, for example, an alginate membrane. Methods for encasing a consumable edible product are found in U.S. Patent Application No. 61/591,054, U.S. Patent Application No. 61/601,852, U.S. Patent Application No. 61/591,262, U.S. Patent Application No. 61/591,233, U.S. Patent Application No. 61/591,225, U.S. Patent Application 61/647,721, U.S. Patent Application 61/713,138, U.S. Patent Application 61/713,100, U.S. Patent Application 61/601,866 and U.S. Patent Application 61/713,063 herein incorporated in their entirety.

In some embodiments, ingestible particles embedded in a membrane are shown to improve the physical, chemical and/or physico-chemical characteristics of the membrane. In certain embodiments, the ingestible particles impart a flavor, for example chocolate or various fruit flavors. When particles are charged and possess the same charge state as other membrane polymers or particulates, one can vary membrane component concentrations (for example, decreasing the membrane polymer concentration and increasing the membrane particulate concentration) while maintaining or optimizing membrane performance. In certain embodiments of, for example, an alginate based membrane, when particles carry the opposite charge state as alginate polymers or particulates, one can minimize or eliminate the need for a calcium solution or another multivalent ion by using particles to bind with alginates or another charged polymer. For non-alginate based systems, combinations of or homogenous particles can be used to encapsulate the edible material, or can be used in combination with polymers at lower weight %-by-mass than the particles (for example, less than 80%, less than 70%, less than 60%, less than 50%, less than 40%, less than 30%, less than 20%, less than 10% polymer). In certain embodiments, a thinner membrane can be sufficient to encapsulate a larger quantity of ingestible material, which may have further advantages of taste and texture. Particles contemplated herein include large food particles, for example greater than 1 millimeter (linseeds, sesame seeds, poppy seeds, chia seeds, chopped or pulverized foods including fruits, fruit skins, vegetables, etc.), small grains, and pulverized seeds, nuts, etc. In some embodiments, compositions use particulates less than about 1 millimeter.

In certain embodiments, particulates used for the membrane(s) can advantageously affect the membrane strength, diffusion permeability, and stability. Important variables when considering particulates as components for membranes include: 1) the particle charge or net charge of a heterogenous or homogenous particulate mix, 2) the specific combinations of particulates for a heterogenous mix, 3) the hydroscopic or hydrophilic nature of the particulates, 4) solubility of particulates in a liquid polymer, 5) aqueous solubility of the particles, 6) particle solubility in polar, non-polar or amphipathic solvents, 7) particle size, 8) heterogeneity of particle size, 9) heterogeneity of particle sizes in a heterogenous or homogenous mix of particles, 10) shape of particulates in a heterogenous or homogenous mix of particles, and 11) chemical and physical nature of the edible or potable substance to be encased in the membrane when interacting with the particulates.

In some embodiments, the particles are neutrally charged. In some embodiments, the particulates have various charge states, and can have an opposite charge as the membrane polymer or other membrane constituents. The overall charge state of the membrane polymer or other membrane constituents influences the choice of particulates, as particles oppositely charged to the charge state of the membrane polymer or particle matrix are likely incorporated into the membrane matrix and preferentially bonded. Oppositely charged particles could contribute to the formation of salt bridges within the membrane matrix and/or membrane polymeric subunit architecture.

In certain embodiments, polysaccharide polymers are used as the membrane polymer. Polysaccharide polymer based membranes are porous, with porosity determined by the chemical content and 2- and 3-dimensional geometry of the polymeric structure of the membrane, for example the structure of the polysaccharide chain. Therefore, particulates are used that can be appropriately accommodated by the pore structure of the membrane, whether as particles that can be intercalated between polymeric chains and/or embedded into the pores to act as a plug based on a particulate size and shape, electrostatically bind to create salt bridges, enhance Van der vaal's interactions that can contribute to overall membrane stability, etc. As described herein, various physical and chemical characteristics of the particulates are matched to the membrane structure and chemistry to achieve a desired effect, for example increased impermeability, elasticity, membrane strength-to-weight ratio, color, syneresis, etc.

In some embodiments, the particulates used for the membrane are sized at about 0.01 microns, at about 0.1 microns, at about 0.1 to 1.0 microns, at about 0.1 to 10 microns, at about 0.1 to 100 microns, at about 0.01 to about 1 millimeter or to about 3 millimeters, or at about 0.1 to about 1 millimeter or to about 3 millimeters. The size of the particulates may be important for embedment characteristics into the porous structure of the membrane.

The porosity of membranes is also determined in part by the ratios of the subunits and or the particulates that assemble to form the membrane. For example, alginate based membranes are composed of manurronic acid and guluronic acid subunits. In general, for alginates, increasing the number of guluronic acid subunits relative to the number of manurronic acid subunits will contribute to a loss of mobility of the membrane polymers, resulting in a stiffer and more stable membrane. However, the stability is also offset by increased porosity of the membrane. Also contributing to porosity can be the overall concentration of polymer used when in solution. All else being equal, increasing the concentration (and therefore the density) of a polymer can decrease the porosity of the final membrane. However, other considerations such as consumer preference or gustatory experience when ingesting the membrane will likely limit the range of desirable polymer concentrations. Therefore, ratios of polymeric building blocks and/or particulates of a membrane may be considered for determining membrane porosity with respect to particulate embedment, solution diffusion, and membrane permeability, and how these characteristics are related to each other.

In certain embodiments, the molecular weight of the membrane polymer is between about 2000 daltons and about 2,000,000 daltons or larger. In other embodiments, the polysaccharide polymer present in solution is between about 0.1% by weight and about 5% by weight, between about 0.1% and 10%, by weight, or greater.

In certain embodiments, not all of the particulates are incorporated into the membrane. Instead, in some embodiments, a layer of particulates remain unincorporated, and form a layer next to a membrane or between two or more membrane layers. The additional particulate layer therefore contributes to, for example, permeability, elasticity, strength, durability, syneresis, hydroscopy, hydrophobicity, etc., changes across and within membrane layers. Thus, the chemical nature of the particulates, for example if a hydrophobic particulate is used, can contribute to impeding the flow of liquid diffusion across an inner layer to an outer layer surface boundary. In some embodiments, particulates can be layered so that the particulate layer has multiple effects, for example an inner impermeability layer, a middle flavor/texture/payload (e.g. a pharmaceutical or supplement) layer, and an outer strength improving layer.

In some embodiments, the particulate used may serve as a flavoring agent, a sweetener, a bittering agent, or to impart a salty flavor. Various foods and flavorings in powdered or extract form are contemplated, including fruits, vegetables, herbs and spices, and various food salts (onion salt, garlic salt, sea salt, etc). Some embodiments use any of a variety of herbal extracts, energy supplements, dietary supplements, pharmaceuticals, over-the-counter drugs, sleep aids, appetite suppressants, weight gain agents, antioxidants, nutraceuticals, confections, and the like. As used herein, over-the-counter drugs refer to pharmaceutical compounds and compositions that had required a prescription but have been released from such prescription requirement for purchase and consumption.

In some embodiments, the edible or potable substance can be coated in a plurality of membranes. In certain embodiments, the membrane layers are distinct and melded. In other embodiments, the membrane layers are separate and distinct from other membrane layers. In certain embodiments, the same polymer, particulate, or combination of polymer(s) and/or particulate(s) is used for each of the multi-membrane coatings as described herein. In certain embodiments, different polymers, particulates, or combination of polymer(s) and/or particulate(s) are used for each membrane in a multi-membrane layer. In some embodiments, a multilayered outer membrane has the same polymer, particulate, or combination of polymer(s) and/or particulate(s) in each of the outer layers, but the membrane components are different than that used in, for example, the inner membrane or other inner membrane layers.

To accomplish the use of the same membrane components in a multi-membrane layered system while keeping the layers separate and distinct, in some embodiments, the inner membrane is first constructed, with or without additional particulates and/or polymers incorporated into the inner membrane. The membrane coated substance can then be layered with one or more additional polymer/particulate layers of homogenous or heterogenous polymer/particulates, and then the particulate layer can be coated again with another membrane. The process may be repeated as many times as desired to construct a multilayered product. can we physically distinguish multi-layers?

Various membrane polymers are contemplated for use in the membrane forming layers. Considerations for choice of membrane polymers include inherent physico-chemical characteristics (charge states, functional groups, kinetic reaction rates of polymerization, ion complex formation and cross-linking, etc.), texture, polymerization characteristics, reactivity to chemical interactions and reactions such as pH, ionic strength, specific ions and ratios of ions during polymerization, presence of complexing agents (e.g., phosphates, citrate, ethylenediaminetetraacetic (EDTA) acid, acids, glucono-delta-lactone (GDL), etc.), shielding susceptability of electrostatic character of polymer and polymeric strands, and cost effectiveness if used for commercial production. Polysaccharide polymers contemplated herein include, but are not limited to, shellac, various fibers and hydrocolloids such as alginate, an agar, a starch, a gelatin, carrageenan, xanthum gum, gellan gum, galactomannan, gum arabic, a pectin, a milk protein, a cellulosic, gum tragacanth and karaya, xyloglucan, curdlan, a cereal β-glucan, soluble soybean polysaccharide, a bacterial cellulose, a microcrystalline cellulose, chitosan, inulin, an emulsifying polymer, konjac mannan/konjac glucomannan, a seed gum, and pullulan. Combinations of these polysaccharides are also contemplated herein.

Other membrane compounds considered for use as structure forming compounds to modify or be used in combination with a polymer-based membrane (for example, a membrane consisting of a polysaccharide) include bagasse, tapioca, chitosan, polylactic acid, processed seaweed, chocolate, starch, gum arabic, cellulose based fibers, natural and synthetic amino acids and polymers thereof, proteins and sugars/sugar derivatives. Combinations of these compounds and compositions are also contemplated herein.

A multi-layered and/or multi-component membrane for transport systems can have several advantages: increased longevity or freshness of the edible or potable substance; limited diffusion of aqueous components of membrane polymers or edible and potables substances; decreased water activity of the potable or edible payload; wider spectrum of taste sensation and experience by a consumer when powders of different flavors and mouth feel sensations are used, for example, between layers in a multilayered composition, taste improvement of a pharmaceutical or over the counter drug(s) if used as the particulate, etc. Incorporation of particulates into the outer most membrane can modify membrane performance, for example the prevention of the outer membrane from polymerizing and or mechanically bonding with the inner or proximate membrane layer. Unincorporated particulates also likely form a physical barrier between membranes so that a chemical or mechanical bonding between membranes does not occur. Electrostatic repulsion/attraction, hydrophobicity and/or hydrophilicity of particulates and other solvent/solute interactions between particulates and membrane polymer components when may also contribute to preventing an interaction between a polymerized layer and a non-polymerized membrane component.

In some embodiments of a multilayered membrane, the proximately located membrane layers are made using the same polymer and the same particulates. In some embodiments, the proximately located membrane layers are made using different polymers and the same particulates to form the multiple membrane layers. In some embodiments, the proximately located membrane layers are made using the same polymers and different particulates to form the multiple membrane layers. In some embodiments, the proximately located membranes layers are made using different polymers and different particulates to form the multiple membrane layers. In some embodiments, different membranes are chosen wherein there is no inherent chemical or mechanical bonding between the membrane layers, thereby requiring no addition of particulates to the outer surface of the innermost membrane.

In some embodiments, membrane components, for example polysaccharides or proteins, are chemically modified with methods and compositions well known in the art. Modifications are important for altering functional groups of the membrane components which, in turn, can alter polymerization characteristics, chemical characteristics, physico-chemical characteristics, bonding propensities, electrostatics, hydrophobicity or hydrophilicity changes, diffusion propensity and resistance to diffusion, elasticity, stability, etc., in the final polymerized membrane. Modifications include, but are not limited to, carbamoylation, graft polymerization, etherification, esterification, reduction, oxidation, amination (e.g., (poly) lysine, arginine) halogenation, polymerization and degradation, complex formation with metals and salts, etc. See, for example, *Chemical and Functional Properties of Food Saccharides* (ISBN 978-0-8493-1486-5).

In some embodiments, various ions are employed for use in the polymerized membrane and related chemical processes. In, for example, the alginate polysaccharide membrane, ions are used to form cross-linkages between and among individual polymer strands. Various ion/counter ion salt complexes are contemplated for use herein, including, but not limited to, divalent cations such as calcium, potassium, magnesium, manganese, iron, zinc; trivalent cations including, but not limited to, manganese and iron; and salts thereof including, but not limited to, calcium lactate and calcium chloride.

In some embodiments, it is contemplated herein that micelles are formed within membranes and between membrane layers and/or between the inner membrane and the edible or potable substance. Micelles can alter the taste experience or mouth feel for the final encased product. Additionally, micelles engineered into the final membrane coated product may contain other ingestibles including sweeteners, flavors (fruits, herbs and spices, etc.), herbal extracts, energy supplements, dietary supplements, pharmaceuticals, over the counter drugs, sleep aids, appetite suppressants, weight gain agents, antioxidants, nutraceuticals, confections, and the like.

Certain embodiments of natural and artificial flavors contemplated for particulates include, but are not limited to, stevia rebaudioside A, glycyrrizin, thaumatin, sorbitol, erythritol, mannitol, monk fruit, pentadin, xylitol, brazen, sugar, dextrose, crystalline fructose, maltodextrin, trehalose, molasses, aspartame, aspartame acesulfame salt, neotame, acesulfame, saccharin, sucralose, neohesperidin dihydrochalcone, sodium, saccharin, cyclamates, alitame and dulcim.

Flavoring compounds contemplated for use in the membrane may be used to give the formulation payload a taste preferred by the end user, increase or enhance particular flavors or the perception of flavors. Flavors choices can include any fruit or vegetable flavor, or any artificial flavor, to elicit a desired taste perception (sweet, sour, bitty, salty and/or umami, and associated food or flavoring, e.g. mint, taste), as well as herbal or plant flavors that can otherwise be considered non-food (e.g., cinnamon), such as coffee, chocolate, and other confectionary flavors. Other flavor compounds considered as a novelty flavoring include, for example, beer and other alcoholic beverages, hemp, vomitus, and novel combinations of flavors (e.g. beer flavoring with caffeine).

Generally, dietary supplements may be considered as vitamins and/or minerals taken in addition to naturally obtained vitamins/minerals in food. Dietary supplements can be taken 1) to enhance the physical well-being or state of health of the end user, 2) as a health related supplement, or 3) as supplements required for enhancing deficient vitamin/mineral states in the end user. Dietary supplements can also add to a higher quality or perceived quality of the health state of the end user.

In certain embodiments, dietary supplements contemplated for use as membrane particles include, but are not limited to, Ascorbic Acid (Vitamin C), B Vitamins, Biotin, Fat Soluble Vitamins, Folic Acid, HCA (Hydroxycitric Acid), Inositol, pyruvate, Mineral Ascorbates, Mixed Tocopherols, Niacin (Vitamin B3), Orotic Acid, PABA (Para-Aminobenzoic Acid), Pantothenates, Pantothenic Acid (Vitamin B5), Pyridoxine Hydrochloride (Vitamin B6), Riboflavin (Vitamin B2), Synthetic Vitamins, Thiamine (Vitamin B1), Tocotrienols, Vitamin A, Vitamin D, Vitamin E, Vitamin F, Vitamin K, Vitamin Oils, Vitamin Premixes, Vitamin-Mineral Premixes, Water Soluble Vitamins, arsenic, boron, calcium, chloride, chromium, cobalt, copper, fluorine, iodine, iron, magnesium, manganese, molybdenum, nickel, phosphorous, potassium, selenium, silicon, sodium, strontium, sulfur, vanadium and zinc.

Energy supplements are designed to boost mental or physical activity. Various embodiments of ingestible energy supplements contemplated for use in membrane formulations include, but are not limited to, American ginseng, Red ginseng, Siberian ginseng, maca, rhodiola, ginger, guarana, turmeric, acetyl-L-carnitine, L-carnitine, creatine, taurine, L-phenylalanine, L-arginine, tyrosine, acetyl-tyrosine, N-acetyl L-tyrosine, ginko biloba, yerba-mate, kola nut, gotu kola, maitake, cordyceps sinensis, guarana, acai-berry, L-theanine, caffeine, quercitine, synephrine, green tea extract, theophylline, epigallocatechin gallate (EGCG), capsaicin, bee pollen, alpha-lipoic acid, and 1,3 dimethylamylamine (geranium), D-ribose, Fo-Ti, cha de bugre extract and St. Johns wort.

Oral health compounds can contribute to decreasing unwanted bacterial flora and/or covering up unwanted odors and/or flavors. Control of the unwanted flora can decrease incidence of tooth decay, halitosis, and potentially contributes to long-term health benefits including incidence of heart disease.

In certain embodiments, oral health compounds for use as membrane particles include, but are not limited to, fluoride, vitamin C, vitamin B, zinc, menthol, thymol, eucaleptic, sodium bicarbonate, vitamin K, chlorhexidine, and xylitol.

Weight loss compounds are commonly divided into groups categorized as appetite suppressants, acting to manipulate hormonal and chemical processes in the body that otherwise increase hunger and/or the sense of feeling satiated (e.g. anorectics such as epinephrine and norepinephrine/noradrenaline), fat or cholesterol uptake inhibitors (such as green tea extract), gastrointestinal fillers, and thermogeneic compounds which boost a normal metabolic rate of the individual and result in metabolism of fat stores, all of which are contemplated for use in the present invention. Weight loss compounds can be synthetic or natural.

In certain embodiments, weight loss compositions contemplated herein as particles for the membrane include, but are not limited to, hoodia, chitosan, chromium picolinate, conjugated linoleic acid, glucomannan, green tea extract, guar gum, guarana, guggal, senna, ephedra, bitter orange, fucoxanthin, white bean extract, vitamin D, human chorionic gonadotropin, resveratrol, capsaicin, chia, hoodia, L-carnitine, raspberry ketones, banana leaf, red clover, ginger, almonds, acai berry, flax seeds, leucine and lipodrene.

Sleep-aid compounds can assist in slowing the metabolic resting rate of an individual to allow one to relax and gain more restful or longer sleep periods. In certain embodiments, sleep aid compositions contemplated herein for use as membrane particles include, but are not limited to melatonin, 5-hydroxytryptophan, 5-hydroxytrypatmine, diphenhydramine, doxylamine, benzodiazepine, kava, serenite, chamomile, phenibut, catnip herb, chamomile, glycine, hops, L-theanine, L-tryptophan, glycine, GABA and valerian.

Various over the counter and prescription based (pharmaceutical) drugs are contemplated for easier ingestion, and in some instances a more pleasant taste, as would be experienced by the user.

In certain embodiments, over-the-counter (OTC) and prescription (pharmaceutical) drugs contemplated for use as a membrane particle include, but are not limited to, amikacin, gentamicin, kanamycin, neomycin, netilmicin, tobramycin, paromomycin, geldanamycin, herbimycin, loracarbef, ertapenem, doripenim, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spectinomycin, aztreonam, furazolidone, nitrofurantoin, amoxicillin, ampicillin, azlocillin, carbenicillin, cloxacillin, dicloxacillin, flucloxacillin, mezlocillin, methicillin, nafcillin, oxacillin, penicillin, piperacillin, temocillin, ticarcillin, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacine, temafloxacin, mafenide, sulfonamidochrysoiodine, sulfacetamide, sulfadiazine, silver, sulfadiazine, sulfamethizole, sulfamethoxazole, sulfanilamide, sulfasalazine, sulfisoxazole, trimethoprim, trimethoprim-sulfamethoxazole, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, linezolid, metronidazole, mupriocin, platensimycin, quinupristin/dalfopristin, rifaximin, thiamphenicol, tigecycline, tinidazole, Fluoxetine, sertraline, paroxetine, fluvoxamine, citalopram, escitalopram, mirtazapine, triazolam, quazepam, estazolam, temazepam, zolpidem eszopiclone zalepon, Trazodone, citalopram, escitalopram, desvenlafaxine, duloxetine, milnacipran, venlafaxine, tramadol, sibutramine, etoperidone, lubazodone, nefazodone, trazodone, reboxetine, viloxazine, atomoxetine, bupropion, dexmethylphenidate, methylphenidate, amphetamine, dextroamphetamine, dextromethamphetamine, lisdexamfetamine, amitriptyline, butriptyline, clomipramine, desipramine, dosulepin, doxepin, imipramine, iprindole, lofepramine, melitracen, nortriptyline, opipramol, protriptyline, trimipramine, amoxapine, maprotiline, mianserin, mirtazapine, isocarboxazid, moclobemide, phenelzine, selegiline, tranylcypromine, pirlindone, busipirone, tandospirone, aripiprazole, vilazodone, quetiapine, agomelatine, nefazodone, quetiapine, asenapine, carbamazepine, lithium, olanzapine, valproic acid, alprazolam, lorazipam, chlordiazepoxide, clonazepam, etizolam, tofizopam, Azelastine, cetirizine, clemastine, desloratadine, dimenhydrinate, diphenhydramine, doxylamine, fexofenadine, loratadine (Claritin), ketorolac tromethamine, pemirolast potassium, ketotifen, neodocromil sodium, loteprednol etabonate, ipratropium bromide, beclomethasone, dexamethasone, epinastine, fluticasone, oxymetazoline, triamcinolone, cromolyn sodium, flunisolide, mometasone, ciclesonide, carbinoxamine maleate, olopatadine, budesonide, montelukast, clemastine, epinephrine, fluticasone furoate and levocetirizine, Celecoxib (Celebrex), etodolac (Iodine), meloxicam (Mobic), rofecoxib (Vioxx), valdecoxib (Bextra), ibuprofen, naproxen, diclofenac, flurbiprofen, indomethacin, ketoprofen, ketorolac, nabumetone, oxaprozin, piroxicam, sulindac, Aspirin, Acetaminophen, Pseudoephedrine HCl, Dextromethorphan, Chlorpheniramine Maleate, Pseudoephedrine HCl, Xylometazoline, Benzododecinium, Butamirate citrate, Clemastine, diphenynhydramine citrate, diphenynhydramine, Chlorpheniramine Maleate, Dextromethorphan Hydrobromide, Oxymetazoline hydrochloride, guaifenesin, ibuprofin, phenylephrin, Acid production control (omeprazole), laxative (loperimide) smoking (nicotine), Ezetimibe, Simvastatin, Eptifibatide, Sitagliptin, Metformin, Losartan Potassium, Hydrochlorothiazide, Finasteride, Enalapril maleate, Hydrochlorothiazide, raltegravir, peginterferon alpha-2b, caspofungin acetate, imipenem and cilastatin sodium, ertapenem sodium, moxifloxacin, posaconazole, Indinavir sulfate, efavirenz, ribavirin USP, peginterferon alfa and ribavirin, rizatriptan benzoate, dorzolamide hydrochloride, Montelukast sodium, infliximab, mometasone furoate monohydrate, desloratadine, etoricoxib, mometasone furoate, golimumab, albuterol sulfate, mometasone furoate/formoterol fumarate, temozolomide, fosaprepitant dimeglumine, Interferon alfa-2b, Gardasil™, ProQuad™, MMR II™, Varivax™, RotaTeq™, Pneumovax™, Zostavax™, alendronate sodium, etonogestrel/ethinyl estradiol, follitropin beta, etonogestrel, desogestrel, Zelephon, Zolpidem Tartrate, estazolam, flurazepam, temazepam, eszopiclone, zaleplon, zolpidem, Ramelteon, amitriptyline, doxepin, mirtazipine and trazodone, and pharmaceutically active metabolic products and/or metabolic intermediates thereof. In particular embodiments, the pharmaceutical is a sustained release pharmaceutical compound.

Various other compounds are contemplated for use as membrane particles. For example, antioxidants, hormones and other proteins, enzymes, amino acids, probiotics, etc., may be desirable.

In certain embodiments, hormones are used for hormone replacement and supplementation. Various hormones contemplated for use as a membrane particle include, but are not limited to, apidonectin, aldosterone, androgen, natriuretic peptide, 7-Keto-DHEA, Androstenedione, dihydroepiandrosterone (DHEA), Melatonin, Nor-Androstenedione, pregnenolone, progesterone, 19 Nor-4-Androstendiol, 19 Nor-4-Androstendione, 19 Nor-5-Androstenediol, 19 Nor-5-Androstendione, 3-Indolebutyric Acid, 4 Androstendiol, 4 Androstendione, 6 Furfurylaminopurene, 6-Benzylaminopurine, calcitonin, cortisol, erythropoietin, gonadotropin, human growth hormone (HGH), incretins, leptin, lutenizing hormone, orexin, parathyroid hormone, pregnenolone, progesterone, prolactin, relaxin, renin, testosterone, and vasopressin.

In other embodiments, enzymes and amino acids are contemplated for use as a membrane particle, and include, but are not limited to, alpha galactosidase, amylase, bromelain, cellulase, papain, peptidase, protease, proteolytic enzymes, superoxide dismutase, trypsin, betaine, casein, glutamic Acid, L-alanine, L-arginine, L-cysteine, L-glutamine, L-glycine, L-histidine, L-isoleucine, L-leucine, L-lysine, L-methionine, L-ornithine, L-phenylalanine, L-proline, L-taurine, L-threonine, L-tryptophan, L-tyrosine, L-valine, N-acetly-L-cysteine, protein soluble soy, soy protein isolates, and whey protein isolates.

In certain embodiments, antioxidants contemplated for use as membrane particulates include, but are not limited to, carotenoids, flavonoids, isoflavones, tocopherol, tocotrienol, lipoic acid, melatonin, superoxide dismutase, coenzyme Q10, alpha lipoic acid, vitamin A, chromium biotin, selenium and ascorbic acid.

In certain embodiments, carotenoids contemplated for use as membrane particles include alpha-carotene, beta-carotene, cryptoxanthin, lycopene, lutein, zeaxathin, apocarotenal astaxanthin, canthaxanthin, lutein/lutein esters, etc.

In some embodiments, flavonoid used as membrane particles include esveratrol, quercetin, rutin, catechin, proanthocyanidins, acai berry extract, raspberry extract, cranberry extract, pomegranate extract, plum extract, cherry extract, rosemary extract, etc.

In some embodiments, isoflavones are used as membrane particles, including, but not limited to, genistein, daidzein, biochanin A, and formononetin.

Further embodiments for particulates in membranes include probiotics to re-establish healthy intestinal bacterial flora. In certain embodiments, probiotics for use in the present invention include, but are not limited to, *Bacillus coagulans* GBI-30, 6086, *Bifidobacterium animalis* subsp. *lactis* BB-12, *Bifidobacterium longum* subsp. *infantis* 35624, *Lactobacillus acidophilus* NCFM, *Lactobacillus paracasei* St11 (or NCC2461), *Lactobacillus johnsonii* NCC533), *Lactobacillus plantarum* 299v, *Lactobacillus reuteri* ATCC 55730 (*Lactobacillus reuteri* SD2112), *Lactobacillus reuteri* Protectis (DSM 17938, daughter strain of ATCC 55730), *Saccharomyces boulardii, Lactobacillus rhamnosus* GR-1 & *Lactobacillus reuteri* RC-14, *Lactobacillus acidophilus* NCFM & *Bifidobacterium bifidum* BB-12, *Lactobacillus acidophilus* CL1285 & *Lactobacillus casei* LBC80R, *Lactobacillus plantarum* HEAL 9 & *Lactobacillus paracasei* 8700:2, *Lactobacillus bulgaricus, Streptococcus thermophiles*, and/or *Bifidobacterium* spp.

Plants and plant extracts can provide compositions for dietary supplements, energy products, antioxidants, sleep-aids, weight-loss products, nutraceuticals, oral health compounds, novelty products, etc. Such compositions may be categorized as botanical supplements and botanical extracts. Aqueous or oil based botanical supplements can be combined at low volume with powdered components or be combined into membrane components, edible or potable substances, or into micelles engineered into membranes.

In certain embodiments, botanical extracts and plant-based supplements for use as membrane components include, but are not limited to, Acerola Extracts, Alfalfa, Blue Green algea, Aloe, Amla, Angelica Root, Bacopa Monnieri, Mucuna Pruriens, Anise Seed, Arnica, Artichoke, Ashwagandha, Astragalus, Ayurvedic Herbs, Barberry, Barley Grass, Barley Sprout Extract, Benzoin, Bilberry, Bioflavonoids, Bitter Melon, Bitter Orange, Black Cohosh, Black Currant, Black Walnut, Bladderwrack, Blue Cohosh, Blueberry, Boswellia, Brahmi, Broccoli, Burdock, Butcher's Broom, Calendula, Capsicum, Cascara Sagrada, Cat's Claw, Catnip herb, Cayenne, Celery Seed, Certified Organic Herbs, Chamomile, Chapparal, Chaste Berry, Chicory Root, Chinese Herbs, Chlorella, Chlorophyll, Citrus Aurantium, Cocoa, Coriander, Corn Silk, Cranberry, Curcuminoids, Damiana, Dandelion, Devil's Claw, Diosgenin, Dong Quai, Echinacea, Elderberry, Elecampane Root, Ephedra, Essential Oils, Eucalyptus, Evening Primrose, Eyebright, Fennel, Fenugreek, Feverfew, Flax Products, Garcinia, Cambogia, Garlic, Gentian, Ginger, Ginkgo, Biloba, Ginseng (American), Ginseng (Panax), Ginseng (Siberian), Goldenseal, Gotu Kola, Grape Seed Extract, Grape Skin Extract, Grapefruit Seed Extract, Green Food Products, Green Lipped Mussel Powder, Green Tea, *Griffonia simplicifolia*, Guarana, Guggul, Gymnema Sylvestre, Hawthorne, Herbal Extracts, Herbal Teas, Hops, Horehound, Horse Chestnut, Horsetail, Hysop, Ipriflavone, Jojoba Oil, Juniper Berries, Kava Kava, Kelp Extract, Kombucha, Kudzu, Larch, Lavender, Lemon Balm, Licorice Extract, Linden Flowers, Lobelia, Maca, Maitake Mushroom, Marshmallow, Milk Thistle, Molasses, Mushrooms, Neem, Nettle, Noni, Nopal, Oatstraw, Octacosanol, Olive Extract, Orange Peel Extract, Oregano Oil, Oregon Mountain Grape, Organic Sweeteners, Parsley, Passion Flower, Pau d'Arco, Pennyroyal, Peppermint, Pfaffia Paniculata, Pine Bark Extract, Piper Longum, Pygeum Africanum, Quercitin, Raspberry Powder, Reishi Mushroom, Resveratrol Extract, Rhubarb Root, Rice Products, Rose Hips, Rosemary Extract, Sage, Sarsaparilla, Saw Palmetto, Schizandra, Seaweed extracts, Senna, Shatavari, Shiitake Mushroom, Silymarin, Skullcap, Slippery Elm, Soy Isoflavones, Soybean Products, Spirulina, St. John's Wort, Stevia, Summa, Tea Tree Oil, *Terminalia ajruna, Tribulus terrestris*, Triphala, Tumeric, Uva Ursi, Valerian Extract, Vegetable Extracts, Vitex, Wheat Germ, White Willow Bark, Wild Cherry bark, Wild Yam, Witch Hazel, Wormwood, Yarrow, Yellow Dock, Yerba Sante, Yohimbine, Yucca, 20-ECD 7-9%, Acetyl L-Carnitine HCl 99%, 4-Androstenedione 99%, Adenophora Tetraohylla Ext 5:1, Alisma Extract 10:1, Alpha Lipoic Acid 99%, Angelica Root Extract, Arbutin 99%, Artemisia Extract 4:1, Artichoke Extract 5%, Globe Asparagus Extract 4:1, Asparagus Powder, Astragulus Extract 10:1, Astragulus Extract 4:1, Astragulus Extract 5:1, Astragulus Root Extract 0.5%, Astragulus Root Powder, Atractylodes Extract 10:1, Avena Sativa Extract 10:1, Avena Sativa Extract 4:1, Barbed Skullcap Extract 10:1, Barberry Extract 10%, Bee Pollen Powder, Beta-Sisterol 35%, Bilberry Extract 10:1, Bitter Melon Extract 8:1, Black Cohosh Extract 2.5%, Black Cohosh Root Powder, Black Pepper Extract 4:1, Black Soy Bean Extract 10:1, Bone Powder, Boswellia Serrata Extract 65%, Broccoli Sprout Extract 10:1, Buchu Leaf Powder, Buplerum (Chai Hu) Extract 5:1, Burdock Root Extract 4:1, Cabbage Extract 4:1, Caffeine (Natural) 86-87%, Caffeine 99%, Calcium Citrate Granular 21%, Calcium-Pyruvate 99%, Carrot Root Extract 4:1, Cassia Nomame Extract 4:1, Catnip Extract 4:1, Cat's Claw (Inner Bark), Powder Cauliflower Extract 4:1, Celandine (Greater) Extract 4:1, Celery Seed Extract, Cetyl Myristoleate 11%, Cetyl Myristoleate 20%, Chaenomeles Extract 4:1, Chamomile Flower Extract 10:1, Chamomile Flower Extract 4:1, Chaste Tree Berry Extract 4:1, Chitin Chitosan 80%, Chitosan 90%, Chondroitin Sulfate 90%, Chrysin 99%, Cinnamon Powder, Cistanches Extract 5:1, Citrus Aurantium Extract 6%, Citrus Bioflavonoid Complex 13%, Citrus Peel Extract 5:1, Clove Extract 5:1, Clove Powder, Coca Extract 4:1, Codonopsis Pilosula Extract 5:1, Colostrum, Common Peony Extract 8:1, Cordyceps Extract 7%, Cornsilk Extract 4:1, Cornsilk Powder, Corydalis Extract 10:1, Cranberry Extract 4:1, Cranberry Powder, Curcumin Extract 95%, Cuscuta Extract 5:1, Damiana Extract 4:1, Damiana Leaves Powder, Dandelion Powder, Dandelion Root Extract 6:1, Danshen Extract 80%, D-Calcium Pantothenate, Devil's Claw Extract 2.5%, Devil's Claw Extract 4:1, Devil's Claw Root Powder, DHEA 99%, Diosgenin 95%, DL-Phenyl Alanine, DMAE Bitartrate, Dong Quai Extract 10:1, Dong Quai Extract 4:1, Dong Quai Root Powder, D-Ribose, Echinacea Angustifolia Extract 4:1, Echinacea Leaf Powder, Echinacea Purpurea Extract 10:1, Echinacea Purpurea Extract 4%, Echinacea Purpurea Extract 4:1, Echinacea Purpurea Root Powder, Elder Flower Extract 4:1, Elderberry Extract 20:1, Elderberry Extract 4:1, Epimedium Extract 10%, Epimedium Extract 10:1, Epimedium Extract 4:1, Epimedium Extract 5%, Epimedium Powder, Eucommia (Du Zhong) Extract 5:1, Fennel Seed Extract 4:1, Fennel Seed Powder, Fenugreek Extract 4:1, Fenugreek Extract 6:1, Feverfew Extract 5:1, Fisetin, Fish Oil Powder, Forbidden Palace Flower Extract 5:1, Forskolin 8%, Fo-Ti Extract 12:1, Fo-Ti Extract 8:1, Fo-Ti Powder, Gardenia Extract 8:1, Garlic Extract 4:1, Garlic Powder, Gentian Root Extract 6:1, Ginger Extract 4:1, Ginger Root Extract 5%, Ginger Root Powder, Ginkgo Biloba Extract 8:1, Ginkgo Extract 24/6%, Ginkgo Extract 24/6%<5, Ginkgo Extract 24/7%, Ginkgo Leaf Extract 4:1, Ginkgo Leaf Powder, Ginseng (Korean) Powder, Ginseng (Panax) Extract 5%, Ginseng (Panax) Extract 8%, Ginseng (Panax) Extract 80%, Glucomannans Konjac Powder, Glucosamine HCl 95%, Granulation Glucosamine HCl 99%, Glucsosamine Sulfate Potassium, Glucsosamine Sulfate Sodium 95%, Granulation Glucsosamine Sulfate Sodium 99%, Goldenrod Extract 4:1, Goldenrod Powder, Goldenseal Root Extract 14%, Goldenseal Root Powder, Gotu Kola Extract 16%, Gotu Kola Extract 4:1, Gotu Kola Extract 8:1, Gotu Kola Powder, Grape Fruit Powder, Grape Seed, Grape Seed Extract 10:1, Grape Seed Extract 20:1, Grape Seed Extract 4:1, Grape Seed Extract 5:1, Grape Seed Extract 95%, Grape Seed Powder, Grape Skin Extract 20:1, Grape Skin Extract 4:1, Grass-Leaved Sweetflai Extract, Green Lip Mussel Extract, Green Tea Extract 30%, Green Tea Extract 4:1, Green Tea Extract 95%, Guarana Seed Extract 10%, Guarana Seed Extract 22%, Guarana Seed Extract 25%, Guggul Extract 10%, Guggul Extract 2.5%, Gugulipid Extract 10%, Gymnema Sylvestre Extract 25%, Gymnema Sylvestre Powder, Hawthorne Berry Extract 4:1, Hawthorne Berry Powder, Hawthorne Leaf Extract 2%, Hearbacious Peony Extract 5:1, Hesperidin Extract 98%, Honeysuckle Herb Extract 4:1, Hops Flower Extract 4:1, Horehound Extract 10:1, Horehound Extract 4:1, Horehound Herb Powder, Horse Chestnut Extract 20%, Horse Chestnut Extract 4:1, Horse Chestnut Powder, Horsetail Extract 7%, Horsetail Powder, Houttuynia Cordata Extract 5:1, Hydrangea Extract 8:1, Hydroxy Apatite, Hyssop Extract 4:1, Indole-3-Carbinol 99%, Isodon Glaucocalyx Extract 10:1, Japanese Knotweed Extract, Jiaogulan Extract 4:1, Jin Qian Cao Extract 4:1, Jingjie Extract 4:1, Jujube Fruits Extract 4:1, Kava Kava Extract 30%, Kava Kava Powder, Kelp Extract 4:1, Kelp Powder, Kidney Bean Extract 10:1, Kidney Bean Pole 4:1, Kidney Bean Pole 8:1, Kidney Bean Powder, Kola Nut Extract 10%, Kudzu Extract 4:1, Kudzu Extract 6:1, Lettuce Extract 4:1, L-Glutamine, L-Glycine, Licorice Extract 10%, Licorice Extract 5:1, Licorice Powder, Lotus Leaf Powder, L-Tyrosine, Lycium Fruit Extract 4:1, Lycium Fruit Extract 5:1, Ma Huang Extract 6%, Ma Huang Extract 8%, Maca Extract 0.6%, Maca Root Powder, Magnesium Stearate, Magnolia Bark Powder, Magnolia Officinal Extract 4:1, Maca Extract 4:1, Maitake Mushroom Extract 4:1, Marigold Extract (Lutein 5%), Methozyisoflavone 99%, Methylsufonylmethane 99%, Milk Thistle Extract 4:1, Milk Thistle Seed Extract 80% silymarin, Morinda Extract 5:1, Motherwort Extract 4:1, Motherwort Powder, Mucuna Pruriens Extract (15% L-Dopa), Muira Puama Extract 12:1, Muira Puama Extract 4:1, Muira Puama Powder, Mushroom Extract 10:1 (feishi), Mustard Seed Extract 8:1, Myrobalan Extract 4:1, Myrrha Gum Extract 2.5%, N-Acetyl-D-Glucosamine, N-Acetyl-L-Cysteine, Nettle Extract 7%, Nettle Leaf Extract 4:1, Nettle Leaf Powder, Noni Powder, Olive Leaf Extract 18%, Olive Powder Orange Peel Extract 4:1, Orange Peel Powder, Oroxylum Indicum Extract 4:1, Oroxylum Indicum Powder, Oyster Meat Powder, Oyster Shell Powder, Papaya Fruit Extract 4:1, Parsley Extract 10:1, Parsley Extract 4:1, Parsley Leaf Extract 4:1, Parsley Powder, Passion Flower Extract 4:1, Passion Flower Powder, Pau D'Arco Powder, Peppermint Extract 4:1, Peppermint Powder, Perilla Seed Extract 4:1, Periwinkle Extract 4:1, Pharbitidis Extract 4:1, Phosphatidyl Serine 20%, Pine Bark Extract 4:1, Plantago Asiatica Leaf Extract 5:1, Polygala Tenoifolia Extract 4:1, Polygonum Extract, Polygonum Extract 4:1, Pregnenolone 99%, Propolis Extract 3%, Pseudoginseng Extract, Psyllium extract 4:1, Pumpkin Seed Extract 4:1, Purple Willow Bark Extract 4:1, Purslane Herb Extract 4:1, Pygeum Extract 4:1, Quercetin, Radish Extract 4:1, Radix Isatidis Extract 4:1, Radix Polygoni Extract 4:1, Red Clover Extract 4:1, Red Pepper Extract 4:1, Red Yeast Rice, Red Yeast Rice Extract 10:1, Red Yeast Rice Powder, Rehmannia Root Extract 4:1, Reishi Mushroom Extract 4:1, Rhodiola Rosea Extract 4:1, Rhododendron Extract 4:1, Rhododendron Powder, Rhubarb Extract 4:1, Rhubarb Root Powder, Riboflavin (B2), Rice Powder, Rosemary Extract 20%, Rumex Madaid Extract 4:1, Salvia Extract 10:1, Salvia Extract 4:1, SAMe, Saw Palmetto Extract 25%, Saw Palmetto Extract 4:1, Saw Palmetto Extract 45-50%, Saw Palmetto Oil 85-95%, Saw Palmetto Powder, Schizandra Extract 10:1, Schizandra Extract 4:1, Scopolia Acutangula Powder, Sea Cucumber Powder, Senna Leaf Powder, Sesame (Black) Seed Powder, Shark Cartilage Powder, Shitake Mushroom Extract, Siberian Ginseng Extract 0.8%, Siberian Ginseng Extract 4:1, Siberian Ginseng Powder, Skullcap Extract 4:1, Skullcap Extract 4:1, Slippery Elm Powder, Sodium-Pyruvate 99%, Songaria Cynomorium Extract 4:1, Songaricum Powder, Spirulina Powder, St. John's Wort Extract 0.3%, St. John's Wort Extract 4:1, St. John's Wort Powder, Stanol 50%, Stephania Extract 4:1, Stevia Extract 4:1, Sulfate N+ Suma Root Extract 4:1, Suma Root Powder, Taurine Powder, Thorowax Extract 4:1, Tomato Extract, Tomato Extract (0.2% Lycopene), (trans)-Resveratrol 20-25%, *Tribulus* Extract 10:1, *Tribulus* Extract 40%, *Tribulus* Powder, Trifal Extract 4:1, Turmeric Extract 4:1, Turmeric Root Powder, Uva Ursi Extract 4:1, Uva Ursi Powder, Valerian Root Extract 0.8%, Valerian Root Extract 4:1, Valerian Root Powder, Vinca Major Seed Extract 10:1, White Wax Extract 4:1, White Willow Bark 15% (total salicins), White Willow Bark 20%, White Willow Bark 25%, White Willow Bark Extract 4:1, White Willow Bark Powder, Wild Yam Extract 10:1, Wild Yam Extract 16%, Wild Yarn Extract 4:1, Wild Yam Extract 6%, Wild Yam Powder, Williams Elder Extract 4:1, Wolfberry Fruit Extract 10:1, Wolfiporia Extract 8:1, Yellow Dock Root Extract 4:1, Yerba Mate Extract (2% caffeine), Yerba Mate Extract 4:1, Yohimbe Bark Extract 15:1, Yohimbe Bark Extract 2%, Yohimbe Bark Extract 3%, Yohimbe Bark Powder, and Yucca Extract 4:1.

Nutraceuticals are generally thought of as food or food product that reportedly provides health and medical benefits, including the prevention and treatment of disease, and can be defined as a product isolated or purified from foods that is generally sold in medicinal forms not usually associated with food. A nutraceutical may have a physiological benefit or provide protection against chronic disease. Such products may range from isolated nutrients, dietary supplements and specific diets to genetically engineered foods, herbal products, and processed foods such as cereals, soups, and beverages. With recent developments in cellular-level nutraceutical agents, researchers, and medical practitioners are developing templates for integrating and assessing information from clinical studies on complementary and alternative therapies into responsible medical practice.

In certain embodiments, particulate nutraceuticals are used as membrane components, including, but not limited to, 5-Hydroxytryptophan, Acetyl L-Carnitine, Alpha Lipoic Acid, Alpha-Ketoglutarates, Bee Products, Betaine Hydrochloride, Bovine Cartilage, Caffeine, Cetyl Myristoleate, Charcoal, Chitosan, Choline, Chondroitin Sulfate, Coenzyme Q10, Collagen, Colostrum, Creatine, Cyanocobalamin (Vitamin B12), DMAE, Fumaric Acid, Germanium Sesquioxide, Glandular Products, Glucosamine HCL, Glucosamine Sulfate, HMB (Hydroxyl Methyl Butyrate), Immunoglobulin (Immune System Support), Lactic Acid, L-Carnitine, Liver Products, Malic Acid, Maltose-anhydrous, Mannose (d-mannose), MSM, Other Carnitine Products, Phytosterols, Picolinic Acid, Pyruvate, Red Yeast Extract, S-adenylmethionine (SAMe), Selenium Yeast, Shark Cartilage, Theobromine, Vanadyl Sulfate, Velvet Deer Antler, Yeast, ATP, Forskolin, Sterol Esters, Stanol Esters, Probiotics, Lactoferin, Lutein Esters, Zeaxanthin, Immunoglobulins, Ipriflavone, Isoflavones, Fructo-Oligo-Saccharides, Inulin, Huperzine A, Melatonin, Medicinal Mushrooms, Bile Products, Peptone Products, Glandular Products, Pancreatic Products, Thyroid Products, Ribose, Probiotics, oleo resins, Dill Seed oleo resin, Black Pepper oleo resin, and Capsicum oleoresin.

Exemplary Food Objects in Transport Systems

In some embodiments, the transport system resembles a naturally occurring object such as, for example, a fruit, a vegetable, etc. In one example, the transport system resembles an orange and contains material derived from an orange and, optionally, other fruits or foods. Typically, a reconstituted orange has an outer shell formed from an exterior surface material as described herein, and optionally, the outer shell is formed of or contains particles of orange, or contains one or more odorants, colorants, texturants, flavoring agents, or the combination thereof such that the reconstituted orange is similar to an orange in one or more sensory experiences. In some embodiments, the outer shell is moldable and texturized such that it approximates the size (e.g., from about 10 to over 100 square inches of exterior surface area) and a tactile quality of an orange. Reconstituted oranges optionally contain other juices and/or other liquids. The reconstituted orange product is consumed by biting and chewing, or by insertion of a straw through the outer shell to draw out the internal contents. Alternatively, a portion of the outer shell is peeled and the contents consumed with a fork or spoon. In related embodiments, the products are reconstituted grapefruits, and have a size (e.g., from about 30 to over 300 square inches of exterior surface area) and a tactile quality of a grapefruit. The reconstituted grapefruit product is consumed by biting and chewing, or by insertion of a straw through the outer shell to draw out the internal contents. Alternatively, a portion of the outer shell is peeled and the contents consumed with a fork or spoon.

In related embodiments, the products are reconstituted grapes and resemble a grape, having a size in the range of about 0.5 to about 2 inches in length and about 0.2 to about 2 inches in girth, of any color. Such a reconstituted grape contains any variety of wine, fortified wine, or other alcoholic beverage, and/or non-alcoholic juice or extract from grapes or other fruits, containing a volume of liquid in the range of about 0.5 milliliter (ml) to about 300 ml or greater, e.g., 1, 5, 10, 20, 30, 50, 75, 100, 150, 200, 250, 300 or over 300 mls. The reconstituted grape product is consumed by insertion of the entire grape product into the mouth and chewing, by biting and chewing, or by insertion of a straw through the outer shell to draw out the internal contents. Alternatively, a portion of the outer shell is peeled and the contents consumed with a fork or spoon.

In related embodiments, the products are reconstituted watermelons, having a size from about 100 to over 4000 square inches, of any color or pattern. The exterior surface material is generally of sufficient thickness to contain the large volume of the reconstituted watermelon, and in some embodiments an additional outer material or casing is present around the exterior surface material to add rigidity and strength to the product. Such additional outer material or casing is generally easily penetrable to access the contents of the reconstituted watermelon. In some embodiments, the products are reconstituted avocado, having a size from about 8 to over 50 square inches, of any color or pattern, with an outer shell resembling in appearance and touch an avocado, and internal contents containing one or more of avocado, avocado paste, guacamole, and/or beverage such as juice, vegetable oil and/or plant oil. The reconstituted avocado product is consumed by biting and chewing, or by dividing into pieces, by cutting and breaking by hand, and consuming it by itself or in combination with another food product, e.g. salad.

In other embodiments, the food object is a dessert containing chocolate, candy, ice cream, caramel, honey, marmalade, bubble gum, or some combination thereof.

Beverage Materials for Use in Transport Systems

Beverage materials are generally liquid in form, are capable of providing nutrition and/or hydration when consumed by a subject such as a human, and are typically provided in a form suitable for the gastrointestinal tract of the subject.

In some embodiments, the beverage material contains a juice, such as fruit juice, vegetable juice, berry juice, or some combination thereof. In some embodiments, the beverage material contains an alcoholic beverage such as beer, wine, fortified wine, or a distilled spirit; optionally such alcoholic beverages are mixed with sugar-containing materials or other flavorants, as well as colorants and/or odorants. In some embodiments, the beverage material contains a dairy product, for example, milk, yogurt, cream, or kefir. Typically, such beverage materials are produced under conditions such that the dairy products do not require refrigeration and do not spoil over a substantial period of time as described herein. In some embodiments, the beverage material contains a soda product, meaning a carbonated flavored beverage. These beverage materials are capable of being chilled so as to be consumed in temperature conducive to best taste and enjoyment. In some embodiments, the beverage material contains water, either purified or from a natural source (e.g., mineral water), and optionally contains carbonation and/or flavorants. In some embodiments, the beverage material contains tea or coffee. The product is capable of being chilled or heated so as to provide the consumer flexibility to consume the product at a temperature most appealing to him or her. In some embodiments, the beverage material contains a sports drink, meaning a water-containing beverage that typically contains sugar (e.g., glucose and/or fructose) and optionally contains one or more vitamins and minerals. In some embodiments, the beverage material contains a soup such as tomato soup, a liquid food sauce such as barbeque sauce, fish sauce, or salad dressing, or a semi-liquid food sauce such as guacamole.

Supplements to Food Materials and Beverage Materials

In some embodiments, food and beverage materials are combined with one or more additional materials: exemplary materials include a vitamin, a mineral, a protein or peptide, dietary fiber material, a lipid, or a combination thereof, as described herein. In some embodiments, the exterior surface materials described herein and/or food or beverage materials contain food particles such as nuts (crushed or not), berries (finely shredded or not), seeds (crushed or not), powders, sugars (crystallized or powdered), and spices.

Exterior Surface Materials of Transport Systems

Exterior surface materials are generally those materials capable of being in contact with food materials or beverage materials so as to contain these materials in three dimensions, typically by interacting with the exterior surfaces of the food or beverage materials. As provided herein, a layer of an exterior surface material, for example a membrane polymer, particulates, and/or a combination of membrane polymer and particulates, is disposed on a food or beverage material so as to essentially completely cover the food or beverage material. In certain embodiments, it is desirable that the exterior surface material is moldable, meaning that the surface material, either in isolation or when contacted with the food or beverage material, is capable of adopting and retaining a desired three dimensional shape. An exterior surface material may be moldable to take the shape or form of a fruit or vegetable, or of a consumer product such as a coffee cup, soda can or bottle, or the like.

Generally, the exterior surface material is not altered in shape or consistency when handled, such as by a consumer. Thus, the exterior surface material generally does not melt or soften, or rupture or otherwise release the contents of the food or beverage object containing the exterior surface material, with typical handling.

In some embodiments, the exterior surface materials of the invention have useful combinations of properties. For example, the surface materials have a thickness in the range of about 10 micron to about 200 mm. In some embodiments, the surface materials have a moisture content in the range of about 10 to about 80%, although the exterior surface materials can optionally be dried or hydrated prior or subsequent to the production process. In some embodiments, the melting temperature of the exterior surface materials ranges from about 30 to about 772 degrees Celsius. The weight of the exterior surface materials may be in the range of about 15 to about 45 grams per 1 square inch sheet of surface material having a thickness of 1 inch. For example, provided are exterior surface materials containing calcium, which has a density of 2.15 g per cubic centimeter. In some embodiments, the exterior surface materials are edible or non-edible, and biodegradable or non-biodegradable.

In some embodiments, the exterior surface materials resemble, taste and smell like a food product or products contained within them. For example, the exterior surface resembles the skin of an orange with orange juice contained within it, or the skin of an apple and pineapple with apple juice and pineapple juice contained within it, whether mixed together or kept separately, thus creating new, yet seemingly familiar environments to experience a certain food or liquid product. Similarly, the exterior surface can bear close, distant, or in-between close and distant resemblance to any combination of any number of foods. In some embodiments, the exterior surface materials do not resemble, taste, or smell like the food or beverage material contained within them. Similarly, in some embodiments, the exterior surface materials resemble, taste, or smell like a particular food or liquid product (for example, an orange, as described herein) but the food or beverage material contain one or more different food or beverage products. Furthermore, in some embodiments, the exterior surface materials have an abstract or unique shape, not resembling an existing food or liquid product. In related embodiments, the exterior surface materials have hybrid shapes, which are expressed as combinations of both abstract or unique shape and resemblance to one or more food products. In related embodiments, the exterior surface materials have shapes or resemblances that appear inedible, for example, an inanimate object such as a house. Such embodiments create opportunities to excite and surprise consumers of reconstituted foods and beverages with new sensory experiences. Consumers typically consume various foods and beverages in combination with each other, and this approach provides these consumers an opportunity to continue this dietary habit while enjoying new combinatorial experiences.

In some embodiments, the exterior surface materials, separating membrane or internal content are composed only of ingredients adhering to standards of kosher certification, as well as to dietary standards desired and expected by individuals who are vegetarian or vegan.

Tensile strength characteristics are important attributes for the surface materials of the transport systems. The tensile strength determines the maximum strength of a surface material and the elastic modulus and elongation will determine the flexibility of a surface material. Additionally, compressive stress characteristics, defined as the capacity of a material or structure to withstand axially directed pushing forces, are also important attributes for the surface materials of the invention.

Flavor, odor, color, and texture are important elements to almost any food or food product. In some embodiments, the exterior surface materials are provided having one or more flavors that may or may not be different from the natural flavors of the food or beverage products contained therein. Flavorings can be natural, artificial, or combine in some proportion both natural and artificial ingredients. According to the Code of Federal Regulations, a natural flavoring is: "the essential oil, oleoresin, essence or extractive, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or similar plant material, meat, seafood, poultry, eggs, dairy products, or fermentation products thereof, whose significant function in food is flavoring rather than nutritional." Flavorings that do not meet the above requirements are considered artificial.

In some embodiments, the exterior surface materials are provided having one or more colors that may or may not be different from the natural colors of the food or beverage products contained therein. Some examples of colorants approved by the Food and Drug Administration are anthocyanin (blueberry and cherry colors), flavonoids (cocoa colors), phycoerythrin (layer colors), carotenoids (orange colors), polyphenol (persimmon colors), and more. Maximum heavy metal tolerance for colorants is generally at 40 parts per million or below.

In some embodiments, the exterior surface materials will have a texture or textures that may or may not be different from the natural textures prevalent in the food or beverage products contained beneath the exterior surface materials. Examples of texturants approved by the Food and Drug Administration include hydrocolloids, which assist with stabilization, suspension and thickening; pectins, which are derived from citrus peels or sugar beets; gelatin; or inulin, which is a natural plant ingredient that provides fiber enrichment.

In some embodiments, the exterior surface materials are combined with one or more odorants that may or may not be different from the natural odorants, if any, present in the food or beverage materials contained beneath the exterior surface materials. These embodiments enable consumers to have sensory-dietary experiences in ways that were not possible or available previously.

As described herein, a multitude of properties of the food and beverage objects provided herein can be modulated when the food and beverage objects are produced. For example, the size of the food and beverage object, along with the external surface area, thickness or thinness of the exterior surface material, and the internal volume, can be modulated. Similarly, the shape, taste, color, texture, smell, and/or mass of the overall product and the shape(s) of its internal content can be modulated.

Storage of Food and Beverage Transport Systems

It is generally desirable that food and beverage objects exhibit long-term stability and not subject to spoiling or deterioration. In some embodiments, the object retains its shape, color, taste, and internal composition for a period in the ranges from several hours to 1 day, 1 day to 3 days, 3 days to 1 week, 1 week to 2 weeks, 2 weeks to 1 month, 1 month to 3 months, 3 months to 6 months, 6 months to 1 year or over 1 year. In some embodiments, the product or constitutive parts will have water activity levels in the ranges from 0.1 to 0.3, 0.3-0.5, 0.5-0.8, or 0.8-1. Water Activity is defined as the amount of unbound, free water in a system available to support biological and chemical reactions (Potter, Food Science, 4th Ed., p. 296, AVI Publishing Co., Westport, Conn. (1986)). Some foods may have high levels of total water content while at the same time possess low water activity. Food designers use water activity to formulate products that are shelf stable. If a product is kept below a certain water activity, then mold growth is inhibited. This results in a longer shelf-life. Water activity values can also help limit moisture migration within a food product made with different ingredients.

It is desirable to possess flexibility in endowing all materials that are encased within the exterior surface materials with varying degrees of liquidity, semi-liquidity, viscosity, solidness, and/or frozenness. In some embodiments, the internal content of the transport system is juice that is liquid. In some embodiments, the internal content is the same kind of juice, but one that is viscous. Viscosity can be important for preventing rapid spillage of the internal content when the exterior surface materials are broken, separated, peeled or cut off in the event of the commencement of consumption.

Viscosity in liquids can be achieved by utilization of viscosity agents, which are substances that swell in water to form a gel. An example of a viscosity agent is methylcellulose, which is a methyl ester of cellulose prepared by the methylation of natural cellulose.

In related embodiments, the internal content of the transport system is an alcoholic beverage, for example, wine, cognac, gin, or some combination thereof, that is liquid. In some embodiments, the internal content is the same of kind of alcoholic beverage, but one that is viscous and/or completely frozen. Among other things, these and similar embodiments convey the fact that the method of consumption that is convenient and enjoyable can differ from one situation to another, and that internal contents of the product can be manipulated to create the desired convenience and enjoyment for the consumer.

Consumption of Food and Beverage Transport Systems

In some embodiments, the transport system or some of its content is ingested in full or in part by direct contact with the mouth. This embodiment is relevant for fruits and food products that are in size, mass and/or texture amenable for ingestion by direct applications to the mouth. Examples of such fruits and food products are grapes, berries, cherry tomatoes, nuts and more, and examples of such product embodiments are grape looking and/or tasting outer shells that contain wine or any other beverage, cherry tomato looking and/or tasting outer shells that contain tomato juice or any other beverage, berry looking and/or tasting outer shells that contain any berry juice or any other beverage. In related embodiments, certain transport systems are sized for convenient servings, such as grape sized membranes for single servings of, for example, ice cream, yogurts (frozen and semi-liquid), gelato, etc.

In some embodiments, the transport system or some of its contents is ingested via insertion of a straw or straw-like equipment. This embodiment is important for such applications as a reconstituted orange, reconstituted watermelon, or reconstituted grapefruit. All of these fruits tend to be too large and/or heavy for consumption in full through the mouth. However, orange- or watermelon- or grapefruit-looking shells could be penetrated by a straw, giving access to the internal contents, which could be juices of those fruits or any other juice or beverage. This embodiment is important because it is analogous to inserting a straw into a coconut and drinking its juice. The embodiment makes this process possible for other kinds of food products, fruits and their juices, providing consumers with new choices of dietary and sensory experiences.

In some embodiments, the transport system or some of its content are ingested via application of spoons, forks, or other forms of relevant cutlery. Reconstituted melon could be presented on a tray, cut with a knife, and consumed with forks or knifes. This embodiment is important because it allows for a communal, shared experience of consuming reconstituted fruit, food products, or beverage. This embodiment is important when consumption of a single product involves two or more people.

Figure 3:
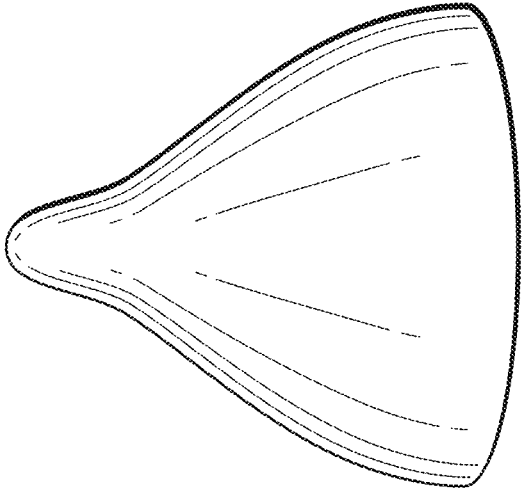
FIG. 3 illustrates another example of a method of consuming a transport system resembling a naturally occurring food product.
Figure 3:
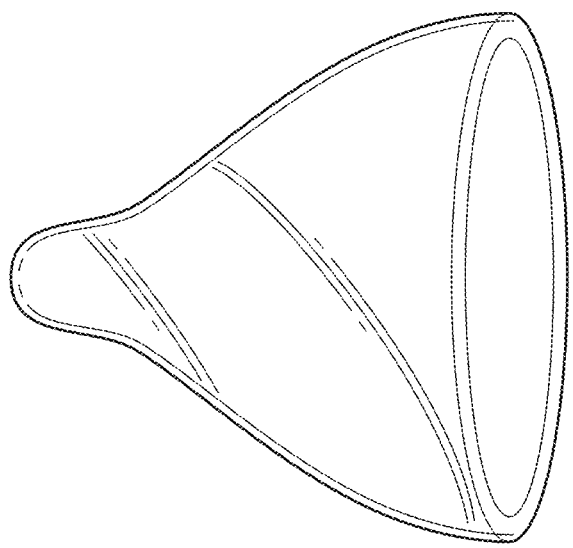

Alternatively, some transport systems can be consumed by removing a portion of the transport system (e.g., biting a portion of the membrane layer) and drinking the inner fluid before eating the membrane layer. For example, FIG. 3 illustrates an example of a transport system having a pointed tip. The tip can be bitten off to form a spout or nozzle from which the inner fluid can be consumed. As shown, the shell for such transport systems can be formed to conform to the non-uniform shape of the membrane layer.

In some embodiments, the product or some of its parts are ingested in combination with, in submergence to, or dissolution into other food products. It is common for people to consume food products and beverages in some combination with each other. In some embodiments, this should be no different for the reconstituted food or fruit product. For example, reconstituted berries could be consumed after submergence into a bowl of milk cereal. As another example, reconstituted fruits could be consumed after submergence into hot chocolate. This embodiment is useful to provide consumers new and exciting sensory experiences.

Packaging, Storage, Presentation and Delivery of the Food and Beverage Transport Systems In some embodiments, the transport system is packaged in various forms of packaging material: for example, wrapping paper, aluminum foil, plastic wrap, cellophane, or wax paper. Such packaging materials exhibit some or all of the following characteristics: light weight, thinness, transparency, or translucency. These qualities are important for aesthetic aspects of packaging that would promote the look and feel of the underlying product. Additionally, such packaging materials as aluminum foil and saran wrap share the quality of water-resistance, thus enabling an additional form of protection for the underlying product in environments where that is needed. Furthermore, flexibility in packaging material is useful for allowing labels or direct printing on the package so that a message about a product or any other message from the vendor could be communicated.

In some embodiments, the final product is presented without any form of wrapping material. The embodiment is important, among other instances, where the final product is produced in venues such as restaurants and cafes and then presented to the consumer for non-delayed consumption.

In some embodiments, the final product is packaged, presented and delivered in various quantities. This embodiment is important, among other instances, in shops and stores where the product is offered to the consumers. Flexibility in packaging in various quantities gives the consumer the flexibility in purchase and consumption of the final product.

In some embodiments, various final products are packaged together into one or more collective products. This embodiment is important, among other instances, because it gives the consumer the flexibility and ability to experience the final product in many or all its available varieties.

Machines for Producing Transport Systems

Figure 4:
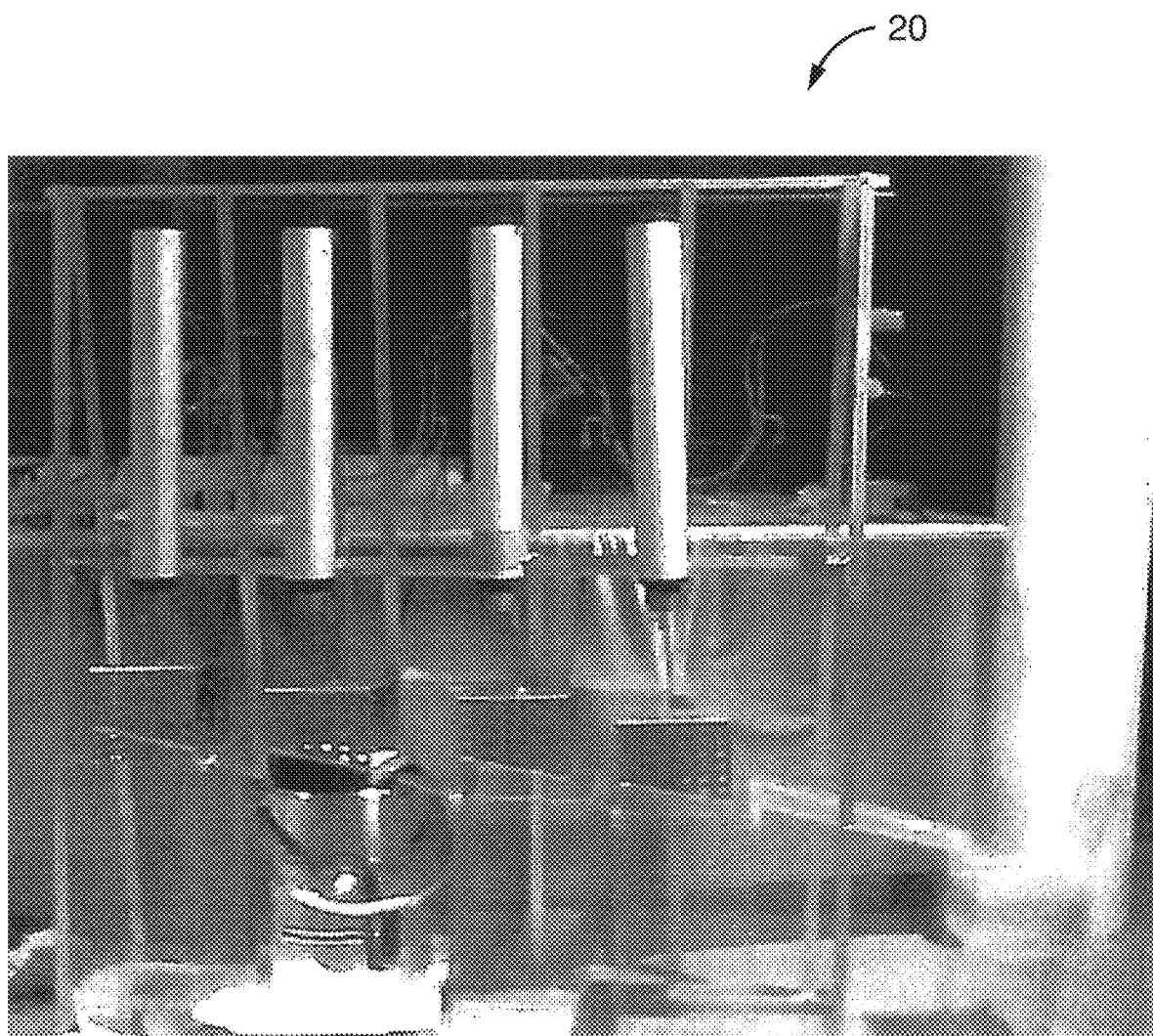
FIG. 4 is a front view of another system for coating objects to form natural transport systems.
Figure 5:
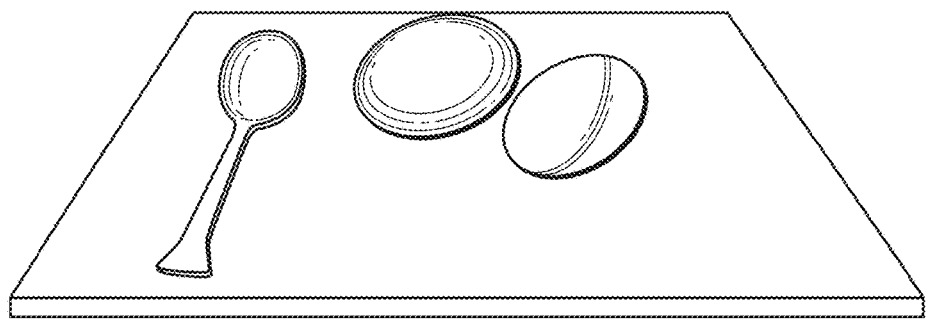
FIG. 5 illustrates a vessel in which liquid water is embedded in a fine jelly membrane of alginates.

FIG. 4 illustrates an exemplary machine for manufacturing edible compositions encased in a membrane as described herein. Systems of the machine may include multiple processing stations and one or more movement devices. The movement device transfers an edible composition among the different processing stations to produce the final edible composition. As shown in FIG. 5, we obtained an "egg of water" (water was used as a reference liquid, but other liquids can also be used), by following the process described later and summarized in FIG. 6. FIG. 7 illustrates the different processing steps that are performed in the different processing stations of a machine 100.

Figure 6:
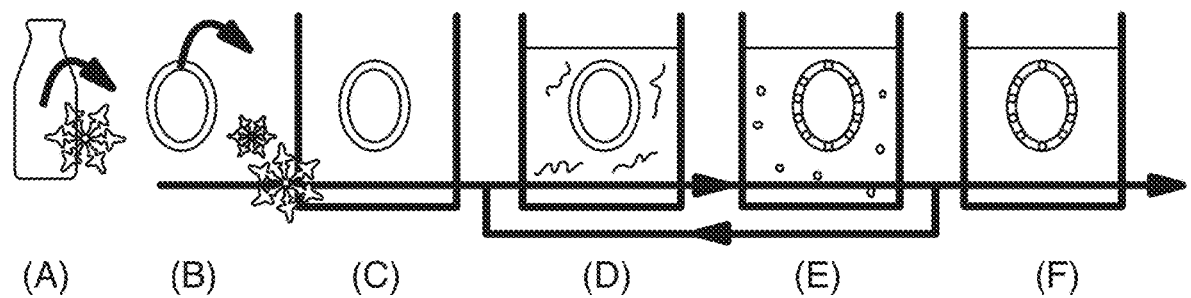
FIG. 6 illustrates a process to create the vessel of FIG. 5.
Figure 7:
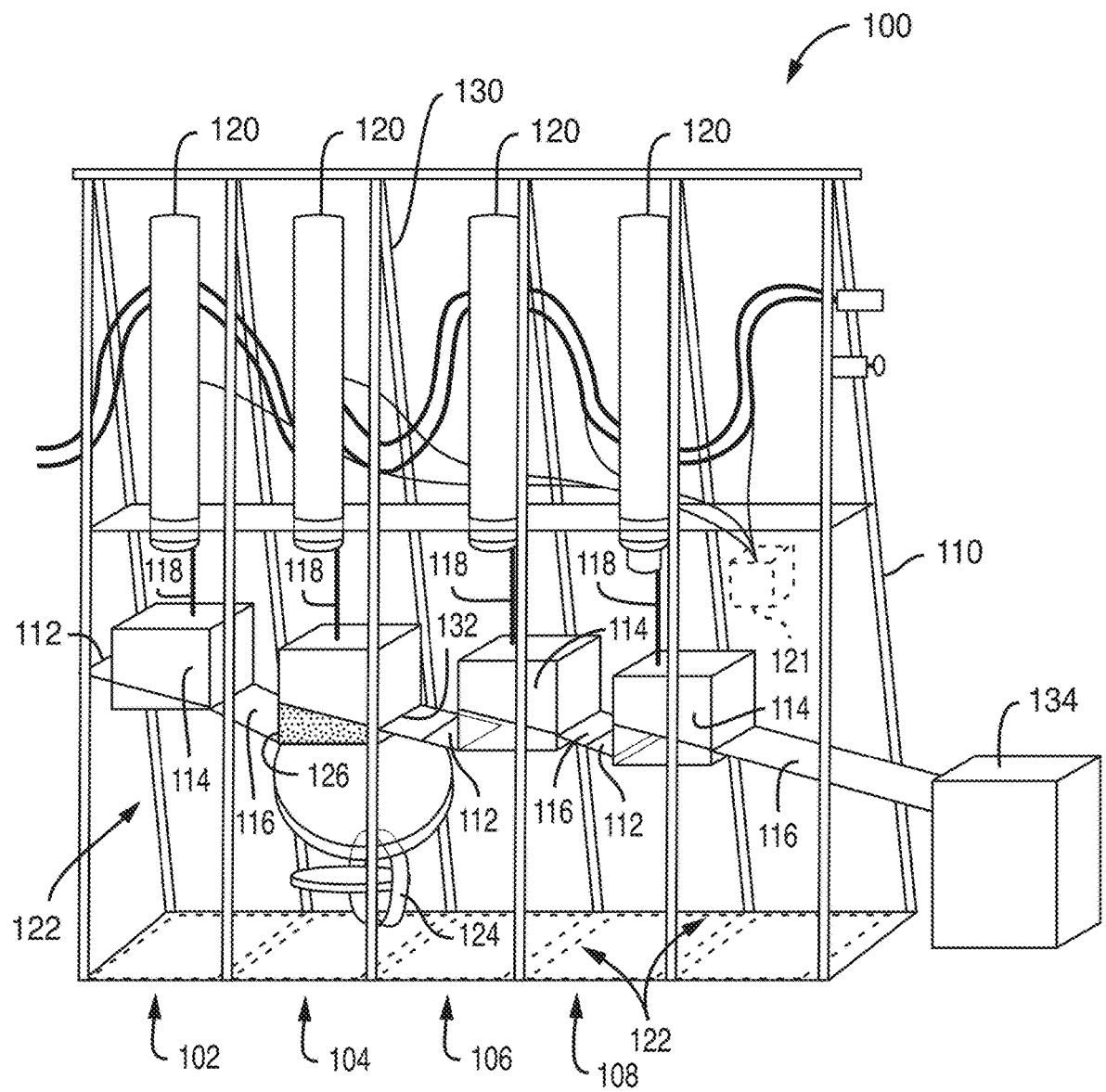
FIG. 7 illustrates the example machine of FIG. 4.

Referring to FIGS. 6 and 7, the exemplary process includes the following steps:

(a) The liquid is frozen in the desired form (e.g., by a person, by an external process or system).

(b) The solid object is then submerged into a bath of calcium solution (e.g., calcium chloride solution) at a first processing station 102. Submerging the solid object into the calcium solution provides a calcium layer on the solid object that produces a higher quality membrane layer. In some embodiments, a greater submersion time in the calcium solution will create a thicker membrane on the solid.

(c) At a second processing station 104, the solid form is then further cooled in liquid nitrogen.

(d) At a third processing station 106, the solid from step (c) is placed in a sodium alginate solution. As the solid is very cold, alginates freeze on the surface. Thus, the thickness of the final jelly membrane is readily tunable. For example, a greater submersion time in the alginates will generally create a thicker membrane on the solid.

Moreover, nitrogen liquid induces a "dried and cold" surface after the step (c), which is the reason alginates adhere easily on this surface. Through our experiments, we have discovered that the step (c) provides particularly improved results: in the case of the process of step (a) directly to step (d) (skipping steps (b) and (c)), the solid in contact with the alginate solution at room temperature (approximately 20° C.) melts quickly on the solid surface, thus creating a liquid film between the solid and the alginate solution. Consequently, it is very difficult to stabilize a homogeneous membrane.

(e) After the desired time needed to achieve the desired thickness of the membrane, the membrane-covered solid is moved to a fourth processing station 108 and is placed in calcium solution (e.g., calcium chloride solution), where gelation occurs.

Optionally the steps of placing the calcium-coated solid in alginates and then placing the membrane-covered solid in calcium (step (d) and step (e)) can be repeated to produce a thicker, harder, and more rigid shell, with or without the other steps (e.g. additional cooling in liquid nitrogen).

(f) The membrane covered frozen solid is rinsed (e.g., in water). The liquid within the calcium-coated membrane is allowed to melt gradually.

The machine 100 has a frame 110 that supports components of the machine including individual processing stations. The first processing station 102 includes an inlet chute 112 to receive an object and deliver it to a cage 114. The inlet chute 112 is inclined to permit the object being coated to roll (or slide) towards the cage 114. In this example, the inlet chute 112 is inclined about 15° downward.

The cage 114 is sized to receive and contain the objects being coated. The cage 114 is formed of material allowing fluid to freely flow in and out of the cage 114. The exemplary cage 114 is a box-like structure made of aluminum sheet metal having multiple holes to permit fluid to flow in and out of the cage 114 surrounding the object. The cage can also have other constructions and be made from other types of materials. For example, in some embodiments, the cage is shaped like a sphere, an ellipsoid, a pyramid or other semi-rigid shapes. Alternatively, in some embodiments, the cage is non-rigid, for example, a net, a sling, a bag, a suspended platform, and/or other object-supporting devices. While the cage has been described as being made from perforated sheet metal, other types of materials can be used. For example, in some embodiments, the cage is made of mesh, textile, netting, and/or cables. In some embodiments, the cage is made from other metals, plastics, glass materials, and/or composites.

A lower surface of the cage 114 is inclined downwards away from the inlet chute 112 which tends to cause an object supported in the cage 114 to roll or slide away from the inlet chute 112. In this example, the lower surface of the cage 114 is inclined about 15° downward. The lower surface is typically covered with or made from a non-stick material (e.g., Teflon®) to prevent the object from sticking to the cage 114. The lower surface of the cage 114 includes a flange to act as a stop preventing the object from rolling off of the inlet chute 112 until the cage 114 is properly aligned with the inlet chute 112. An upper surface of the cage 114 provides a downward force onto the object when the object is submerged in a fluid and has the tendency to float. Two opposing sides of the cage 114 are open so that the object can roll into the cage 114 from the input chute 112 and exit the cage 114 via an outlet chute 116 arranged on the opposite side of the cage 114.

The outlet chute 116 is offset at a generally lower vertical position relative to the inlet chute 112 and is inclined downward away from the cage 114. In this example, the outlet chute 116 is inclined about 15° downward. As a result of the inclination, during machine operation, the object can roll (or slide) from the input chute 112 into the cage 114 and subsequently from the cage 114 to the outlet chute 116. The inlet chute 112 and the outlet chute 116 are inclined and the outlet chute 116 is at a lower general vertical position than the inlet chute 112. This configuration provides a station in which the lower end of the inlet chute is at a lower vertical position than the upper end of the outlet chute 116. As a result, when an object enters the cage 114 from the inlet chute 112, it is prevented from exiting the cage 114 via the outlet chute 116 until it is lifted above the upper end of the outlet chute.

Within the first processing station 102, the cage 114 is raised and lowered to submerge the object within and remove the object from a liquid bath. In this machine 100, the cage 114 is secured to a vertical moving arm 118 extending from a movement device 120. The movement device 120 is a linear actuator that vertically moves the cage 114 vertically for receiving the object from the inlet chute 112 and submerging the object into and retrieves the object out of a volume of fluid contained in a fluid vessel 122. From the fluid, the movement device 120 lifts the cage 114 to deliver the object to an outlet chute 116 of the first processing station. In the exemplary machine 100, the movement device 120 is a 24V DC electric actuator having 300 mm of maximum displacement. The movement device 120 has a maximum displacement speed of about 80 mm/s, a maximum driving force of about 200N and upper and lower position detectors that restrict motion to within a desired distance range. The movement device 120 is in communication with a control unit 121 that controls the movement of the device 120 and the position of the cage 114. The movement device 120 is typically operated using timers (e.g., double pole, double throw (DPDT) switch times). Other types of control devices and actuators (e.g., other types of electromechanical actuators or pneumatic actuators) can also be used as the movement device.

The fluid vessel 122 is a reservoir filled with a volume of liquid to coat the object when submerged by the movement device 120. The fluid vessel 122 is made of materials suitable to contain fluid (e.g., Plexiglass) and is sized to permit submersion of the cage 114. For example, the fluid vessel is about 140 mm wide, about 140 mm deep, and about 360 mm high. In some embodiments, walls of the fluid vessel are an integrated part of the frame 110. In the first processing station 102, the fluid vessel contains a calcium solution (e.g., calcium chloride solution) that surrounds the object in a calcium layer. The calcium layer formed between the object and a subsequently formed alginate membrane layer typically results in a higher quality alginate membrane layer. While the fluid vessel 122 has been described as containing a volume of still fluid, in some embodiments, the cage 114 lowers the object into stream of flowing fluid. Via the movement device 120 and the cage 114, the object is submerged for a length of time and is then raised and delivered to the output chute 116 from which the object can roll to an input chute 126 of the second processing station 104.

An inlet chute 126 of the second processing station 104 is in proximity to and extends substantially along the same plane as the first processing station outlet chute 116. The second processing station 104 is similar to the first processing station 102. However, in this machine 100, unlike the first processing station 102, the second processing station 104 is configured to submerge the object into a bath of liquid nitrogen. Due to the material properties of liquid nitrogen (e.g., very low temperatures) the fluid vessel containing liquid nitrogen (e.g., a liquid nitrogen vessel 124) is sized and constructed to suitably contain the liquid nitrogen. For example, in this machine 100, the liquid nitrogen vessel 124 is a round Dewar flask (e.g., an AGIL6 model flask from Air Liquide). However, other types of vessels suitable for housing liquid nitrogen can be used.

Since the liquid nitrogen vessel 124 is round (i.e., as opposed the general rectangular shaped fluid vessel 112), some components of the second processing station 104 are different than those of the first processing station 102 to accommodate the round shape. For example, the second processing station inlet chute 126 has a curved lower edge to more closely conform to the round shape of the liquid nitrogen vessel 124. The cage 114 of the second processing station has a flange 130 attached to its right side (i.e., the side of the cage 114 opposite from the inlet chute 126). The flange 130 has a curved forward edge that is sized to roughly fit along the inner surface of the liquid nitrogen vessel 124 so that a gap between the curved flange 130 and the inner surface of the liquid nitrogen vessel 124 is small enough to allow the object to slide or roll out the cage 114 and onto a second processing station outlet chute 132.

The second processing station outlet chute 132 is inclined downward away from the cage 114 and is at a lower vertical position than the second processing station inlet chute 126. Like the second processing station inlet chute 126, in this example, the second processing station outlet chute 132 has a curved edge that is offset from the curved edge of the flange 130 or an outer surface of the liquid nitrogen vessel 124 to accommodate the round liquid nitrogen vessel 124.

These features increase the likelihood that the object rolls into and out of the cage 114 without getting stuck or lodged between the inlet chute 126 and the cage 114 or the cage 114 and the outlet chute 132.

An inlet chute 112 of the third processing station 106 is in proximity to and extends substantially along the same plane as the second processing station outlet chute 132. The third processing station 106 is generally the same as the first processing station 102. The third processing station 106 is configured to raise and lower the object into a bath containing a solution for coating the object with a membrane. For example, in this machine 100, a fluid vessel 122 in the third processing station 106 contains an alginate solution (e.g., 1.5% sodium alginate solution) that coats the object when a cage 114 is lowered into the bath via the movement device 120. Once the object is raised from the liquid bath, the cage 114 delivers the coated object to an outlet chute 116 of the third processing station 106 that is at a lower vertical position than the inlet chute 112 of the of the third processing station 104.

An inlet chute 112 of the fourth processing station 108 is connected to and extends substantially along the same plane as the third processing station outlet chute 116. The fourth processing station 108 is generally the same as the first and third processing stations 102, 106. The four processing station 108 is configured to raise and lower the object into a bath containing a solution for solidifying the membrane applied to the object at the third processing station 106. For example, in this machine 100, a fluid vessel 122 of the fourth processing station 108 contains a calcium solution (e.g., calcium chloride solution) that coats and solidifies the object membrane when a cage 114 is lowered into the bath via the movement device 120. Once raised from the liquid bath, the cage 114 delivers the solidified object to an outlet chute 116 of the fourth processing station 108 that is at a lower vertical position than the inlet chute 112 of the of the fourth processing station 106.

The output chute 116 of the fourth processing station 108 delivers the object from the machine 100 to a container (e.g., hopper) 134 for rinsing/cleaning, packaging, storage, shipping, or immediate use and consumption.

During operation, an object (e.g., a frozen object) is moved throughout each of the processing stations to form the transport system. In this example, the frozen object is generally round. However, in some embodiments, the object is pre-frozen to be other shapes.

First, a frozen object, such as a frozen amount of a liquid food product (e.g., water, juice, soup, soft drink, alcohol, or other food) is placed onto the inlet chute 112 of the first processing station 102. In this example, the object is placed on the inlet chute 112 manually, for example, by a machine operator. An "Archimedes' Screw" device can optionally be used to introduce frozen objects one-by-one into the machine, to help prevent the objects from sticking to each other. In some embodiments, frozen objects are automatically placed on the inlet chute 112 by a machine. In some cases, the machine placing the frozen objects on the inlet chute 112 also molds and freezes, or otherwise forms liquid into frozen objects.

Once on the inlet chute 112, the frozen object rolls (or slides) downward along the inlet chute and stops against the cage 114. Due to an initial position (e.g., an upper position) of the cage 114 relative to the inlet chute 112, the lower surface of the cage 114 keeps the object on the inlet chute 112 until the cage 114 is moved to submerge the object in the fluid vessel 122. The movement device 120 of the first processing station then receives a signal from the control unit 121 and begins moving the cage 114 downward. Once the cage 114 moves far enough so that object is no longer blocked by the lower surface of the cage 114, the object rolls into the cage 114. The cage 114 continues to move downward until it is fully submerged in the calcium solution (e.g., a 2% calcium solution) in the fluid vessel 122 and reaches a bottom position. Once in the bottom position, the object is held in the calcium solution long enough so that a calcium layer is formed on the object. In this example, the cage 114 remains at the bottom position for a submerging time of about 3 seconds to about 15 seconds (e.g., about 5 seconds). After the submersion time, the movement device 120 moves the cage 114 upwards towards the upper position. When the cage 114 reaches the upper position, its lower surface substantially aligns with the outlet chute 116 of the first processing station 102 so that the object can roll out of the cage 114 and towards the inlet chute 126 of the second processing station 104 to be deep-frozen.

When the object rolls from the first processing station outlet chute 116 to the second processing station inlet chute 126, the cage 114 of the second processing station 104 is typically in its upper position. Like the first processing station 102, a lower surface of the cage 114 of the second processing station 104 holds the object on the inlet chute 126 until the cage 114 is moved downward towards its bottom position within the liquid nitrogen vessel 124. After a brief pause, the movement device 120 of the second processing station 104 receives a signal from the control unit 121 and begins moving downward. Once the cage 114 is moved downward far enough that the object is no longer held in place by the lower surface of the cage 114, the object rolls into the cage 114. While the cage 114 moves downward into the liquid nitrogen vessel 124, the object is submerged into liquid nitrogen. Once the cage 114 reaches its bottom position, it remains in place while the object undergoes deep freezing due to the liquid nitrogen bath. In some cases, this also dries the object and allows membrane-forming materials to crystalize onto and stick to the surface of the object. In this example, the object is submerged in the liquid nitrogen for about 45 seconds to about 60 seconds to form a super-frozen object. Once the object is submerged for the desired time, the movement device 120 begins moving the cage 114 upwards towards its upper position. Once the cage reaches the upper position, the super-frozen object rolls or slides from the cage 114 to the outlet chute 132 of the second processing station 104.

From the outlet chute 132 of the second processing station 104, the super-frozen object rolls onto the inlet chute 112 of the third processing station 106 to have a membrane layer applied. Like the first and second processing stations 102, 104, a lower surface of the cage 114 of the third processing station holds the super-frozen object on the inlet chute 112 while the cage 114 is in its upper position. After a brief pause, the movement device 120 of the third processing station 106 receives a signal from the control unit 121 and begins moving the cage 114 downward towards its bottom position to submerge the super-frozen object in the alginate solution in the fluid vessel 122. Once the cage 114 is moved downward far enough that the super-frozen object is no longer held in place by the lower surface of the cage 114, the object rolls into the cage 114. While the cage 114 moves downward into the fluid vessel 122, the super-frozen object is submerged into the alginate solution. Once the cage 114 reaches its bottom position, it remains in place while the alginate solution forms a membrane layer around the object. Typically, greater submersion times in the alginate tend to create thicker membrane layers around the object. In this example, the super-frozen object is submerged in the alginate solution for about 45 seconds to about 60 seconds to form a membrane layer. Once a membrane is formed having a desired thickness, the movement device 120 begins moving the cage 114 back upwards towards its upper position. Once the cage reaches the upper position, a membrane-covered object rolls or slides from the cage 114 to the outlet chute 132 of the third processing station 106.

From the outlet chute 116 of the third processing station 106, the membrane-covered object rolls onto the inlet chute 112 of the fourth processing station 108 to solidify a portion of the membrane layer. Like the first, second, and third processing stations 102, 104, 106 a lower surface of the cage 114 of the fourth processing station holds the membrane-covered object on the inlet chute 112 while the cage 114 is in its upper position. After a brief pause, the movement device 120 of the fourth processing station 108 receives a signal from the control unit 121 and begins moving the cage 114 downward towards its bottom position to submerge the membrane-covered object in the calcium solution in the fluid vessel 122. Once the cage 114 is moved downward far enough that the membrane-covered object is no longer held in place by the lower surface of the cage 114, the membrane-covered object rolls into the cage 114. While the cage 114 moves downward into the fluid vessel 122, the membrane-covered object is submerged into the calcium solution. Once the cage 114 reaches its bottom position, it remains in place while the calcium solution solidifies the outer surface of the membrane. Typically, the greater submersion times tend to create thicker, stronger solidified surfaces on the membrane layers. In this example, the membrane-covered object is submerged in the calcium solution for about 5 seconds to about 60 seconds to form a membrane layer. When the order is Calcium, Nitrogen, Alginate, Calcium, the first Calcium is 5 s and the second Calcium is 60 s. The membrane thickness is also impacted by the particles in solution. These submersion times have been observed to form membranes ranging between about 2 and about 7 mm (e.g., thin membranes, ~2 mm; membranes with small particles, ~3 mm; membranes with large particles up to ~7 mm). Often the membranes are about 5 mm thick.

Once a membrane is formed having a desired thickness, the movement device 120 begins moving the cage 114 upwards towards its upper position. Once the cage reaches the upper position, a final membrane-covered object rolls or slides from the cage 114 to the outlet chute 116 of the fourth processing station 108.

From the outlet chute 116 of the fourth processing station 108, the final membrane-covered object rolls into the container 134 for rinsing/cleaning, packaging, storage, shipping, or immediate thawing, use, and consumption.

In this example, since the processing stations submerge the object in different fluids for different submersion times, only one object is typically processed at a time using the machine 100. Therefore, when the final membrane-covered object is delivered from the fourth processing station 108, a new frozen object is placed in the inlet chute 112 of the first processing station 102. However, other processing sequences are possible. For example, in some embodiments, each movement device 120 is configured to submerge their respective cage 114 for the same submersion times. By submerging the cages in each processing station for the submersion time, multiple objects can be processed at the same time without substantial delay or lag time. Furthermore, with more complex timing, "holding chambers" in between certain processing stations, or other minor modifications, different submersion times can be maintained while also having more than one object processed at a time, without substantial delay or lag time. A well-run machine may be able to produce up to about 30, up to about 60, up to about 80, up to about 100, or more transport systems per hour.

While the inlet chutes, outlet chutes, and lower surfaces of the cages have been described as all being inclined at substantially the same angle, other configurations are possible. For example, in some embodiments, the inlet chutes, outlet chutes, and lower surfaces of the cages are arranged at different inclinations relative to one another While certain processing stations and sequences have been described, the machine can include more or fewer processing stations and/or processing steps. For example, in some embodiments, the machine includes additional processing stations for submerging the object in alginate and calcium to provide additional layers on the object. In some embodiments, it has been found that applying a first layer of calcium, a layer of alginate, and a second layer of calcium, in that order (with or without intervening steps) may allow for thinner, stronger membranes. Other sequences may give rise to a variety of membrane properties.

While the machine has been described as having multiple movement devices that are configured to move independent of one another, other configurations are possible. For example, in some embodiments, the machine has more or fewer movement devices.

While the machine has been described as advancing an object along a substantially straight path, other configurations are possible. For example, in some embodiments, the machine is curved to advance the object around an arc-like or circular path.

While the machine has been described with specific mechanisms and features to transition objects to and from cages 114, including inlet and outlet chutes, other configurations are possible. For example, in some embodiments, objects can be transferred to/from cages 114 without the need for inlet and/or outlet chutes. In some embodiments, the relative heights of the cages 114 and inlet and outlet chutes can vary, depending on the designs of each, and the vertical position of the cages 114 at different times.

In some embodiments, the machine includes one or more aesthetic auditory and/or visual stimulations. For example, in some embodiments, the machine includes audio or visual (e.g., strobe lights, neon lights, colored lights or sequences, or other visual stimulation) that coincides with the object being moved between the various stations. In some embodiments, consumers select a specific consumable substance, membrane characteristics (e.g., flavor and/or texture), and shell characteristics before activating the machine. The consumers can then watch as their selected transport system is made. In some embodiments, this can provide a "custom-made" and rapidly formed edible transport system for immediate consumption. In some embodiments, this can provide a more robust transport system for longer-term use or storage. In some embodiments, the machine is enclosed in a substantially transparent or translucent protective case. In some embodiments, the machine is enclosed in a more opaque protective case.

While the fluid vessels have been described as containing certain solutions for forming a substantially homogenous membrane layer around the object, other configurations are possible. For example, in some embodiments, the solutions contain any of various particles, substances, or materials to modify the texture, composition, structural capabilities, flavor, or other properties of the membrane layer.

While the machines, systems, and methods disclosed herein have been described as being configured to receive, handle, and enclose a typically frozen substance in a membrane, other approaches are possible. For example, in some embodiments, a liquid or semi-solid inner material (e.g., in a non-frozen state) that contains divalent cations is dispensed directly into an alginate solution to form an initial membrane layer that is structurally suitable for handling the inner material and the membrane layer. The membrane-covered inner material can then be removed from the alginate solution (e.g., lifted from the alginate solution), in some cases then submerged in calcium solution (e.g., lowered into the calcium solution), and then further processed in a similar manner as described above, for example, with reference to the machine 100.

The alternative approach can thus reduce or eliminate the steps of freezing the inner material to form a frozen object to be submerged in liquid nitrogen, a first calcium solution, an alginate solution, and then a second calcium solution.

Additionally, the machine for producing the transport system can be simplified, for example, by eliminating the processing station having a liquid nitrogen bath.

Example 1—Preparation of a Reconstituted Orange

A reconstituted orange is obtained by the following process.

1) Orange juice is frozen in a desired shape. 2 ounces of orange juice are poured into a container of desired shape—in this case, a container with two semi-spherical concave shapes.

2) The container with the orange juice is then submerged into a bath of liquid nitrogen (−196 degrees Celsius) for a period from 10 to 30 seconds to form a super-frozen object.

3) Two orange semi-spheres are then removed from the container and attached together to resemble the shape of an orange sphere.

4) Upon attachment, the frozen juice shape is then submerged into an alginate bath. This forms an inner layer around the orange. Alginate (alginic acid) is an anionic polysaccharide. It is a copolymer -(M)m-(G)n-, composed by mannuronate M (manurronic acid) and guluronate G (guluronic acid) monomers respectively. As the solid is very cold, alginates freeze on the surface. Thus, the thickness of the final jelly membrane is readily tunable. Greater submersion times in the alginates will generally create a thicker jelly membrane on the solid. In this example, the object is submerged in the alginate solution for about 5 seconds to 20 seconds to form a membrane layer that is that is 0.5 mm to 2 mm thick.

Notably, liquid nitrogen induces a "dried and cold" surface, which is the reason alginates adhere easily on this surface. Skipping the submersion of the juice into liquid nitrogen by, for example, utilizing an alternative freezing system, puts the solid in contact with the alginate solution at room temperature (approximately 20 degrees Celsius), which makes the solution melt quickly on the solid surface. This creates a liquid film between the solid and the alginate solution, consequently making it difficult to stabilize a homogeneous membrane.

5) The frozen shape enveloped with alginate solution is then again briefly submerged into a liquid nitrogen bath (−196 degrees Celsius) for a period of 10 seconds. This step cools, dries, and/or solidifies the inner layer.

6) The orange juice covered with alginate is submerged into a solution (e.g., calcium chloride solution) which solidifies with the alginates into an edible membrane, with the orange juice inside, which can be allowed to unfreeze. Similar to the alginate layer deposition stage, greater submersion time in the calcium chloride solution generally creates a thicker membrane. In this example, the object is submerged in the alginate solution for about 10 seconds to 30 seconds to form a membrane/shell layer that is 2 mm to 6 mm thick. The membrane/shell is now able to effectively contain the juice within this edible structure.

Example 2—Preparation of a Reconstituted Grape Containing Wine

A reconstituted wine-bearing grape is obtained by the following process.

1) Wine is frozen in a desired shape. In this example, 1 ounce of wine with a pH level of 3.5 is used. The ounce of wine is poured equally into two elongated semi-spherical containers.

2) The container with the wine is then submerged into a bath of liquid nitrogen (−196 degrees Celsius) for a period from 20 to 40 seconds to turn liquid wine into a super-frozen object. This process stabilizes the liquid and enables the further steps of deposition of membranes and encapsulating layers around the wine.

3) The frozen shape is then submerged into a bath of polyglutamic acid for a period of about 5 seconds to about 10 seconds to form a membrane layer that is about 0.5 mm to about 1mm thick. Because the object is very cold, the polyglutamic acid immediately freezes on the surface, forming the first membrane layer. This is an important step, for that membrane layer is both edible and acid-resistant around the coated wine.

4) To prepare the object for the deposition of the second layer, the object is re-frozen again by being re-submerged into a bath of liquid nitrogen for a period from about 5 seconds to about 10 seconds.

5) The frozen object is then submerged into an alginate solution with a 10% concentration of grape particles for a period from about 20 seconds to 30 seconds. This action forces the alginate to freeze and form a second membrane layer around the first membrane that is acid-resistant. The presence of grape particles in the alginate solution gives the wine object a real grape flavor.

6) The frozen wine object with the two membranes is finally submerged into a solution (e.g., calcium chloride solution) for a period from about 10 seconds to about 20 seconds which forms a layer that is about 1 mm to 2 mm thick. This step solidifies the outer membrane and orange juice in an edible container.

Example 3—Preparation of a Soda Can Made of Fruit-Tasting Gellan Gum

A soda-bearing container with edible outer shell is obtained by the following process.

1) Soda is frozen in a desired shape. In this example, 3 ounces of soda with a pH level of 2.5 are used. The ounces of soda are poured into a soda can-shaped container with an open top.

2) The container with the soda is then submerged into a bath of liquid nitrogen (−196 degrees Celsius) for a period from 10 to 20 seconds to turn the soda into a super-frozen object. This process stabilizes the liquid and enables the further steps of deposition of membranes and encapsulating layers.

3) The frozen shape is then submerged into a bath of chitosan-citrate for a period of about 5 seconds to about 10 seconds to form an edible, acid-resistant membrane around the soda that is about 0.5 mm to about 1 mm thick. Because the object is very cold, the chitosan-citrate solution immediately freezes on the surface, forming the first membrane layer. This is an important step, for that membrane layer is both edible and acid-resistant around the soda.

4) The object is then submerged in a gellan gum hot solution. Gellan gum is a polysaccharide, consisting of two residues of D-glucose and one of each residue of L-rhamnose and D-glucoronic acid. This polysaccharide is a good candidate for this process because, contrary to alginates, the gel is mechanically very stable and rigid, and it keeps the form perfectly. The gellan gum solution contains an 8% concentration of fruit particles, which endow the gellan gum solution with a distinct fruit flavor.

5) As the surface of the object is cold, the gelation occurs suddenly.

6) The frozen soda melts slowly into a liquid, which is then firmly embedded in the gellan membrane.

Example 4—Preparation of an "Orange"

In another exemplary process, we prepared an "orange" using the following steps:

1) Orange juice was frozen in spherical mold.
2) The orange juice sphere was submerged into a bath of calcium solution (e.g., calcium chloride solution). Submerging the solid object into the calcium solution provides a calcium layer on the solid object that produces a higher quality membrane layer.
3) The calcium-coated orange juice sphere was then further cooled in liquid nitrogen.
4) The resulting solid was submerged in a sodium alginate solution. The alginate solution included small pieces of orange peel, and orange flavoring. As the solid is very cold, alginates freeze on the surface. Thus, the thickness of the final jelly membrane is readily tunable.
5) After the desired time needed to achieve the desired thickness of the membrane, the covered solid was placed in calcium solution again (e.g., calcium chloride solution), leading to further gelation.
6) The membrane-covered frozen solid is rinsed (e.g., in water). The liquid within the calcium-coated membrane is allowed to melt gradually.

Example 5—Preparation of an Alginate Shell Containing Particles

By adjusting the properties of an alginate solution, a membrane can be designed to be stronger, thinner/thicker, or taste in a particular way, by adding suspended particles of food, e.g. chocolate, nuts, seeds, caramel, fruit or vegetable fragments (e.g., orange rind), or other particles at least partially insoluble in water.

The particles can be sized (e.g., chosen or formed) such that the maximum dimension of the container formed by the membrane is about 10 or 20 or 50 or 100 times larger (or more) than the maximum dimension of the particles.

Figure 8:
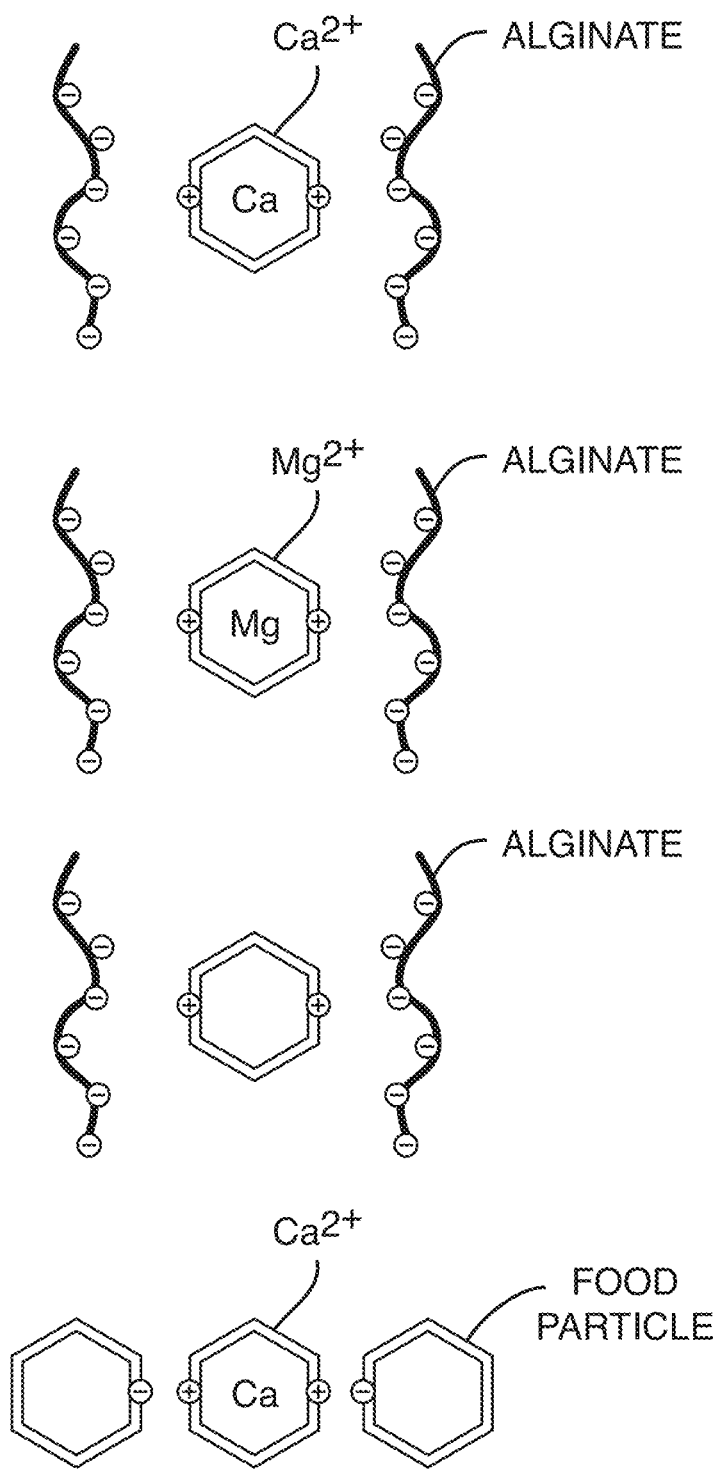
FIG. 8 is a schematic illustrating bonding between positive particles (e.g., $Ca^{2+}$ or $Mg^{2+}$) and negative particles (e.g., alginate or food particles).

Often these particles will be charged (i.e., most particle surfaces have some charge or zeta potential). This charge can be modified by the way each particle is created, its size, and the nature of the particle surface. Surfactants can be added to enhance the charged nature and the ionic atmosphere of the water can also be modified beneficially. When in solution (e.g., alginate or an aqueous medium), these particles (assuming they are zwitterionic or oppositely charged to the membrane forming material, such as the alginate) will undergo strong or weak associations with alginate but not so strong as to cause gel formation. When in contact with calcium, for example, particles will form with alginate a gelled membrane through interaction of the calcium and food particles trapped within the membrane, possibly strengthening it, improving flavor, etc. FIG. 8 schematically illustrates the interaction between positively charged particles (e.g., $Ca^{2+}$ or $Mg^{2+}$) with negatively charged alginate or food particles. The maximum weight of the added material (e.g., chocolate particles) relative to the alginate, can be quite large, i.e., far larger than 1:1 ratio of particles to alginate by mass. This will depend on the desired membrane nature as well as the nature of the particles and the interactions they may have with calcium and alginate.

These same methods can be extended to many kinds of small particles with a charge, thus creating a new class of membrane, formed by a charged polymer, such as alginate, and charged particles, with or without the addition of a multivalent cation such as calcium.

Figure 9:
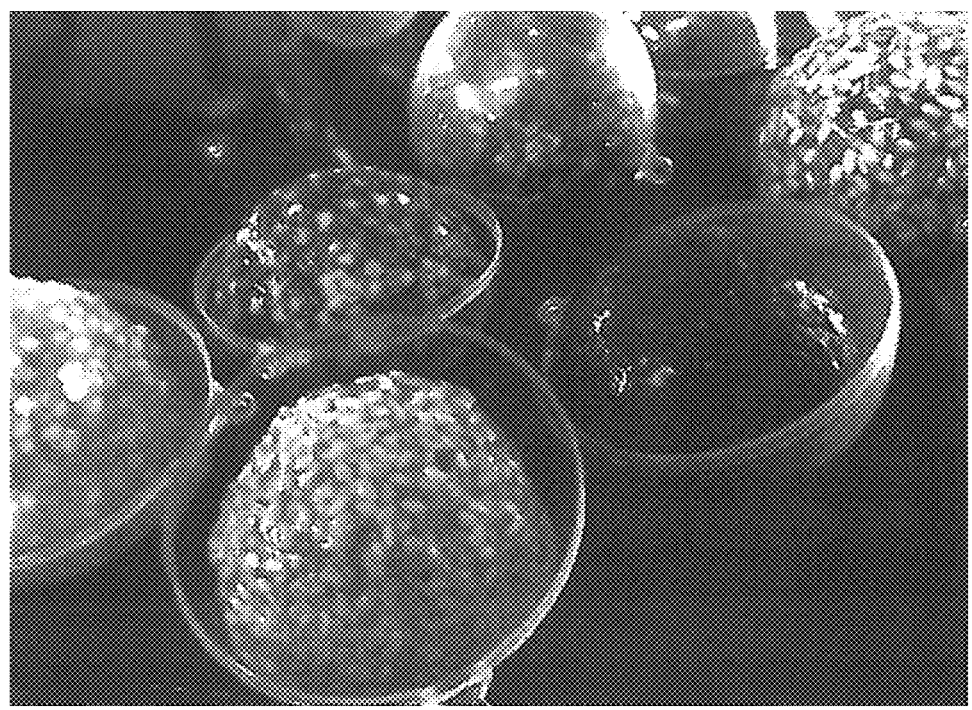
FIG. 9 illustrates multiple transport systems arranged in shells.

FIG. 9 illustrates various transport systems having membrane layers containing different particles (e.g., edible particles). By way of an example, membrane layers can include differently sized particles, different types of particles, or different orientations or configurations of particles. The membrane layers of the transport system can have various sized characteristic dimensions (e.g., diameters). In some embodiments, the diameter of a membrane layer is greater than 1.5 centimeters (e.g., 2 centimeters, 3 centimeters, 4 centimeters, 5 centimeters, 7.5 centimeters, 10 centimeters, 15 centimeters, or 20 centimeters, or greater). Additionally, the transport systems can be enclosed in various shells for packaging, transportation, or storage.

Figure 10:
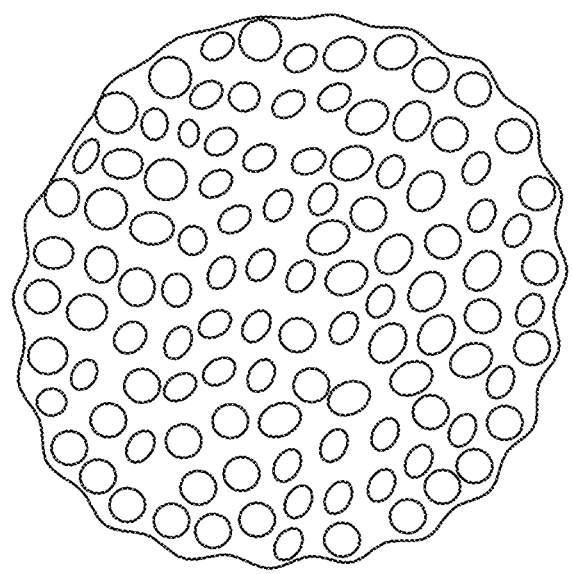
FIG. 10 illustrates a transport system having large particles suspended in an outer membrane layer.

Referring to FIG. 10, in some embodiments, a membrane layer around an ingestible substance includes large particles suspended in the alginate polymer matrix. The large particles can provide structural stability to the membrane and help reduce the likelihood of deformation or the membrane. Such a membrane can have an unusual (e.g., non-spherical) shape. Additionally, large particles can reduce the likelihood of evaporation of the membrane and/or the fluid inside the membrane. Having embedded particles exposed to the exterior of the membrane can also provide a more rigid and/or less sticky surface for holding the vessel. The large particles can have a characteristic dimension (e.g., mean diameter of a sphere or length or radius of a cylinder) that is, for example, roughly about 1 mm to about 30 mm (e.g., about 2 mm to about 5 mm). In some embodiments, the large particles have a diameter that is less than $\frac{1}{5}$, less than $\frac{1}{10}$, or less than $\frac{1}{20}$ of the diameter of the membrane layer.

Some examples of large particles are large seeds (e.g., sesame seeds, linseed), grains, puffed grains (e.g., puffed quinoa or puffed rice), fruit or vegetable pieces (e.g. lemon or orange peel, rind, zest), and nuts. In some cases, these are prepared by blending or grating. In some embodiments, the membrane layer includes one or more different types of large particles.

Figure 11:
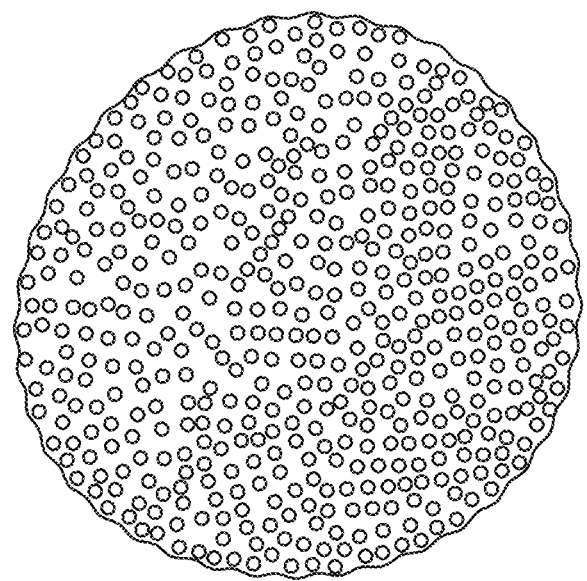
FIG. 11 illustrates a transport system having small particles suspended in an outer membrane layer.

Referring to FIG. 11, in some embodiments, a membrane layer includes small particles suspended in the alginate polymer matrix. The small particles typically have a characteristic dimension (e.g., diameter) that is less (e.g., much less) than $\frac{1}{10}$ or $\frac{1}{50}$ or $\frac{1}{100}$ of the diameter of the membrane. Such small particles can also improve the evaporation properties of the membrane layer, some structural stability, and improve the texture and handling of the vessel. For example, the small particles can have a diameter that is, for example, roughly about 0.1 microns to about 3 mm (e.g., about 0.2 mm to about 1.5 mm).

Some examples of small particles are small seeds (e.g., poppy seeds, chia seeds), small grains, pulverized fruit or vegetable skin, and pulverized seeds. In some embodiments, the membrane layer includes one or more different types of small particles.

Figure 12:
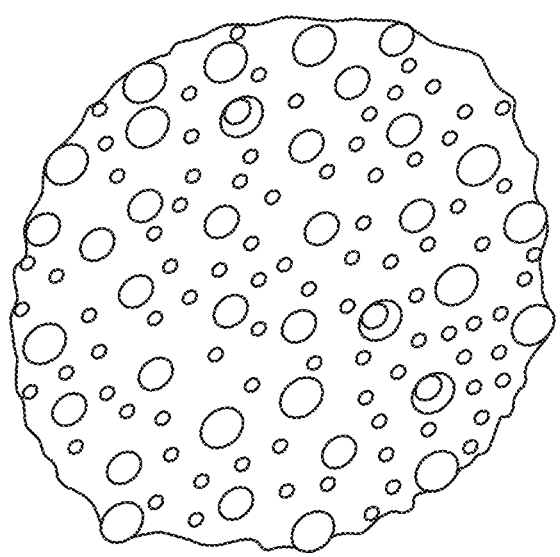
FIG. 12 illustrates a transport system having both large and small particles suspended in an outer membrane layer.

Referring to FIG. 12, in some embodiments, a membrane layer includes a mixture of both the large and small particles suspended in the alginate polymer matrix. In some embodiments, a characteristic dimension (e.g., diameter) of the small particles is less than 75% (e.g., less than 50%, less than 25%, less than 10%, less than 5%, or less than 1%) of a corresponding characteristic dimension of the large particles also suspended in the membrane. In some embodiments, a ratio by weight of the large particles suspended in the membrane to the small particles suspended in the membrane is about 1:2 to about 2:1. For example, an edible bottle may have roughly 4 grams puffed quinoa, 2 grams poppy seeds, and 2 grams sesame seeds.

The membrane layer having both large and small particles has been shown to produce better particle packing and arrangement within the membrane layer, possibly better structural integrity, reduced water evaporation from the membrane or the fluid contained therein, and forming more useful textures than membrane layers having only large or small particles.

For example, samples having puffed quinoa, linseed, sesame seed, poppy seed, and/or chia seed were tested. The tested samples with both large and small particles were shown to maintain adequate evaporation and structural properties for up to 1-2 weeks, whereas similar membrane layers having no particles suspended in the membrane were shown to maintain similar structural properties for only 48 hours. Membranes with only large or small particles, or with fewer particles, were shown to generally maintain similar structural properties for an intermediate duration (i.e., in some cases, between 48 hours and 1 week).

It is also important to note that particles of a variety of sizes can be used together, even if the sizes do not clearly correspond to "large" and "small". The distinction between large and small particles described here is meant to be exemplary of having particles of more than one typical size in a membrane. In some embodiments, there will be one kind of "large" particle and one kind of "small" particle; in other embodiments, there may be more than two kinds (i.e. characteristic sizes) of particles, or there may be more than one kind of "large" particle, or there may be more than one kind of "small" particle, etc. Overall, the mixture of larger and smaller particles generally leads to tighter packing of the particles.

Figure 13:
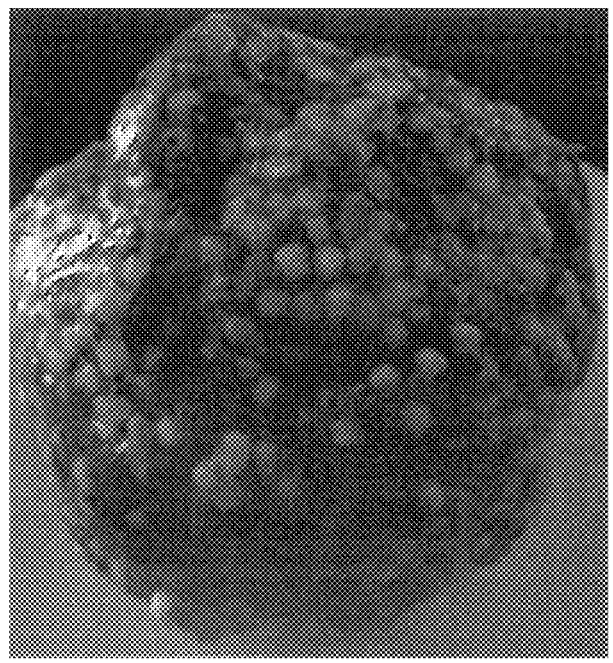
FIG. 13 illustrates a transport system having an outer membrane layer that is non-uniformly shaped.

In some embodiments, transport systems are formed as non-spherical, non-uniform shapes. Referring to FIG. 13, a membrane of a transport system can include ridges or features for aesthetic and/or structural purposes. As discussed below, in some embodiments, the transport system is constructed to resemble naturally occurring objects (e.g., fruits and vegetables). In some cases, the membrane is formed to be non-spherical by forming a non-spherical object on which the membrane is applied. For example, to make a cylindrical membrane, a cylindrical frozen object can be molded or sculpted and a membrane subsequently formed thereon. However, non-spherical or non-uniform shapes are also created by other means. For example, in the membrane solutions, random particle arrangements, agglomeration, higher viscosity, and particle packing during the formation of the membrane, can lead to unusual shapes. It is believed that larger particles in the membrane tend to increase the likelihood of getting unusual (non-spherical) shapes, and that these also increase the overall rigidity of the membrane. Such non-homogeneous shapes can be used to create "substructures" in the membrane, whereby perhaps taste, dosage release, or other properties are modulated by the presence of agglomerates, or other particle formations.

Example 6—Protective Effects of Inner Membrane

To demonstrate that a hard, external, biodegradable membrane can be protected from the water that it contains by a soft internal membrane, e.g., produced by calcium alginate, we produced outer shells of polylactic acid (PLA) and exposed them to either water or to water with a membrane of calcium alginate between the water and the PLA. We exposed the PLA shells, with and without the calcium alginate membranes, to 45 degrees C. external temperatures for 30 days and then observed the PLA shells afterward.

In the presence of water and no calcium alginate membrane, the PLA shells became opaque, reflecting a degradation of the PLA shell through contact with water. In contrast, the PLA shells separated from water by a calcium alginate membrane remained transparent, indicating little or no degradation.

Additionally, the PLA surface in the presence of the alginate membrane remained relatively smooth. In contrast, the surface of the PLA shell exposed to water without the intervening calcium alginate membrane remained comparatively rough. This is understood to indicate that the calcium alginate membrane protects the PLA shell from degradation due to the presence of the internal liquid.

Figure 14:
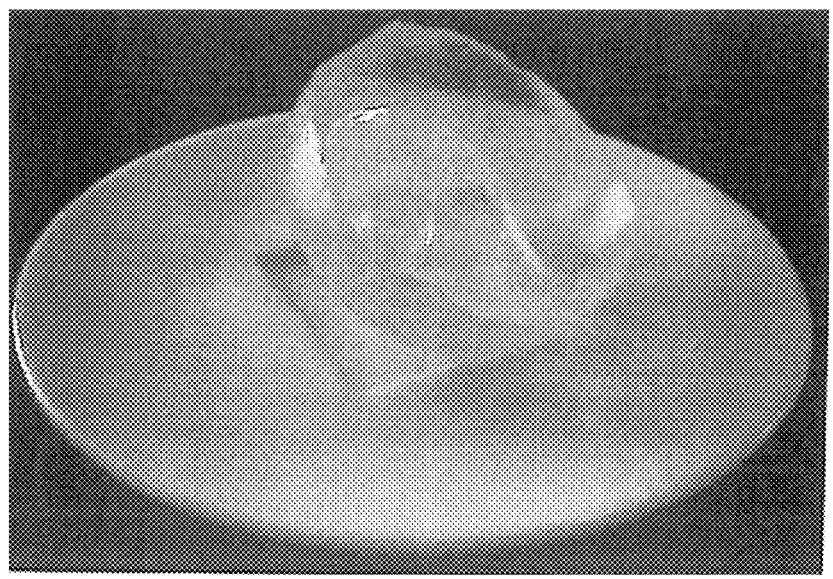
FIG. 14 illustrates a portion of a shell layer for enclosing a transport system.

In some embodiments, the transport systems are enclosed in shell made of an ingestible shell material. The shell material is generally harder and more structurally resilient at room temperature than the membrane layer. The shell layer can be made from various edible or biodegradable materials, such as, for example, isomalt, poly(lactic acid) (PLA), caramel, bees wax, chocolate, hard candy, pastry shells, cookies, wafers, waffles, or other materials. FIG. 14 illustrates a translucent shell made of isomalt that is roughly 2 mm in thickness.

Shells can be made of edible materials that are relatively solid and dry at room temperatures but become liquid at higher temperatures. For example, isomalt and caramel have been used. In one embodiment, translucent isomalt shells have been prepared as follows: Mixing 3 parts isomalt powder with 1 part water
  Heating to approximately 170 degrees C.
  Pouring into molds for making spheres (i.e. a pair of "half sphere" molds)
  Allowing to cool for roughly 5 minutes
  The isomalt in contact with the mold surface cools and hardens more rapidly than the rest of the isomalt, so this more-liquid isomalt can be removed (e.g. poured out) from the mold, leaving an "empty", harder shell in the shape of the mold.
  A membrane-enclosed vessel may be added now to a first half of a spherical isomalt shell
  A second half-sphere isomalt shell can be joined to the first, the two connected and sealed by wetting the isomalt at the joining edges (making the isomalt sticky) and allowing the shell to dry Caramel shells have been prepared similarly, heating to 130 degrees C. For both caramel and isomalt, the temperatures to which they are heated for melting tend to yield, upon cooling, harder, more stable solids.

Figure 15:
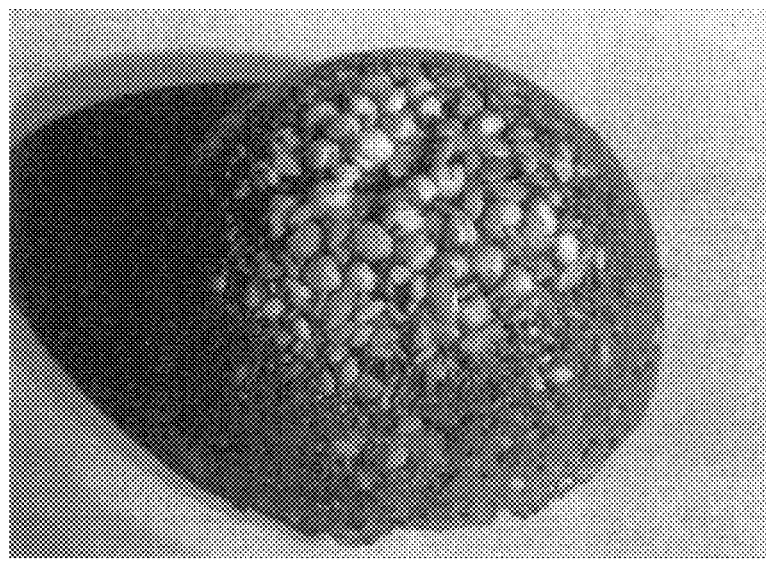
FIG. 15 illustrates a portion of a shell layer for enclosing a transport system having particles arranged within the shell layer.

Like the membrane layer, particles can be added to the shells to change the structure, appearance, stability, taste, texture, "stickiness", humidity, or other characteristics of the shell, and/or reduce evaporation of internal liquid. Particles added to the shell can include sesame seeds, puffed quinoa, or other particles mentioned. Referring to FIG. 15, for example, in some embodiments, a shell includes multiple, different types of particles (e.g., puffed quinoa, linseed, sesame seeds, chia seeds, and poppy seeds) distributed throughout the isomalt shell. In this particular embodiment, soluble apple flavoring, green coloring agents, and citric acid, were also added to the shell.

In some embodiments, a glazing agent such as shellac (E904) can be used to help improve the impermeability of a shell (or membrane) at least temporarily. Shellac has also been used in the preparation of isomalt shells in molds. Applied to the mold surface directly, it can act as a temporary "glue" and hold in place food particles against the mold surface. After liquid isomalt is poured in, the particles then adhere to the isomalt, and end up on the external surface of the isomalt shell. Particles can also be added to the external face of an isomalt shell by adding moisture, causing it to become sticky, and rolling the shell in the particles or otherwise attaching the particles to the shell. Among other advantages, having particles on the exterior of the shell can provide a way to handle the vessel that minimizes direct contact with the shell, which in some cases (e.g. isomalt) is sensitive to humidity and may be sticky and unpleasant to touch.

Further research has shown that mixing one of the membrane-forming substances, such as calcium solution, with the shell liquid, such as isomalt, may be another method to create more stable vessels. In one embodiment, a solid (e.g. frozen) edible substance can be dipped into the isomalt+ calcium solution, and then in an alginate solution, to create a protective layer. Gum arabic has been used in such studies to vary the viscosity of the solutions.

Other studies are directed toward the addition of particles to the inside of the shell, and the addition of powders to the shell (outside, inside, or throughout), to enhance the humidity-barrier, structural, aesthetic (e.g., opacity), or other properties of the shell.

Figure 16A:
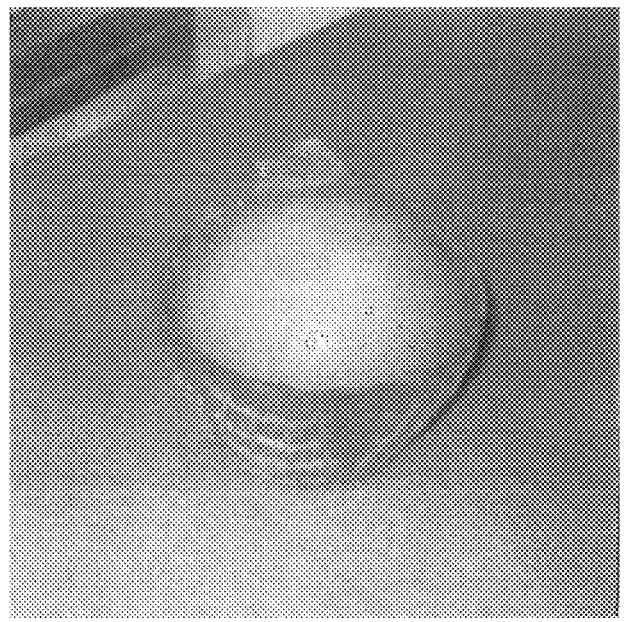
FIGS. 16*a-c* illustrate an example of enclosing a transport system in a shell.
Figure 16B:
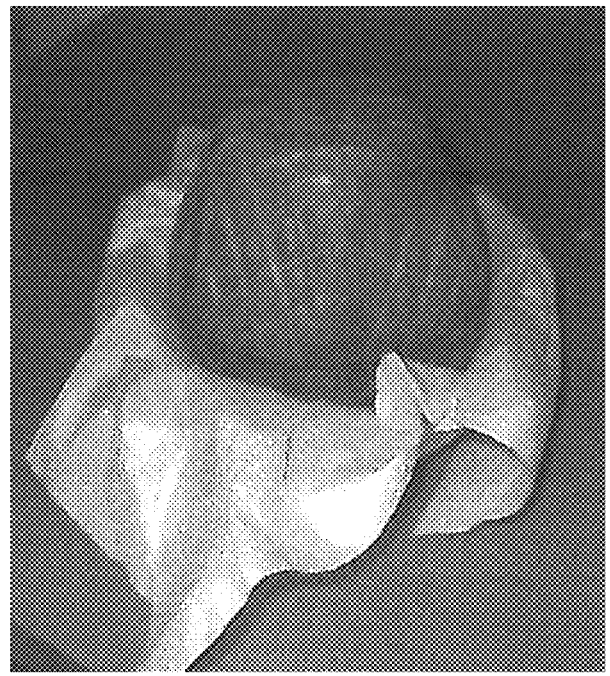
Figure 16C:
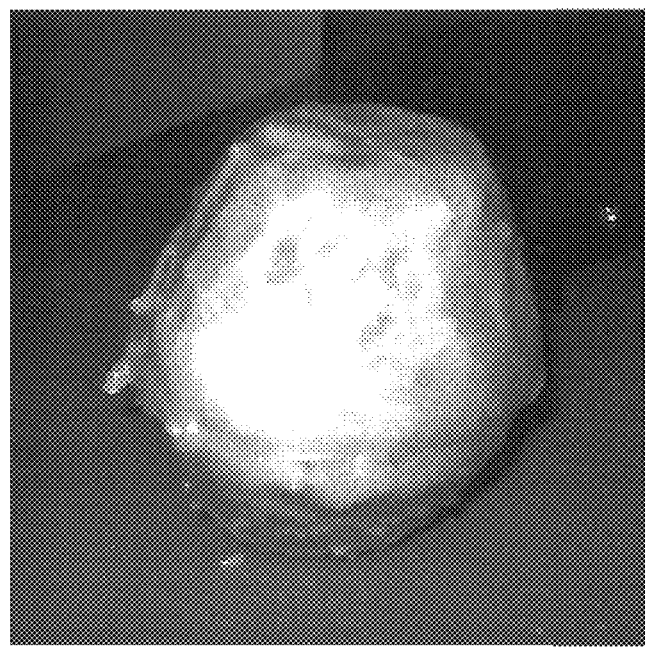

Other types of shells are possible. FIGS. 16a-16c show an example of a shell and a method for enclosing a transport system within a shell. First, referring to FIG. 13a, a transport system can be placed into a lower, bowl-like portion of a shell. In this example, the transport system contains a pear flavored filling encased in a membrane. The shell can be made from a commercially available edible food container or a container that is made specifically for the transport system that it will contain. The lower portion is typically sized and configured to enclose or contain at least about 50% of the volume of the transport system. In this example, the container is a commercially available waffle cone bowl.

Referring to FIG. 16b, an upper portion of the shell can be placed on top of the lower portion to enclose the transport system. The upper portion can be substantially the same as the lower portion to form a generally symmetrical shell. In this example, the upper portion, like the lower portion, is a commercially available waffle cone bowl (e.g., the same waffle cone bowl as the lower portion). The upper portion is placed onto the lower portion to enclose the transport system in a clamshell manner. The upper and lower portions can be bonded to one another or they can include mating features to secure the shell together. In some embodiments, the shell can be implemented in other shapes and configurations. For example, a flat wafer could be used as the top portion of the shell.

Once assembled, the shell can be coated by a sealing material. The sealing material can bond the upper and lower portions of the shell to one another, as well as reduce the likelihood that the shell will degrade (e.g., due to environmental conditions). The sealing material can also reduce the likelihood that moisture will pass from inside the shell to outside the shell, which could result in water evaporating from the membrane layer of the transport system. Referring to the FIG. 16c, the enclosed shell is covered in an edible sealing material (e.g., wax, frosting, glaze, icing, or other spreadable food product). In one example (shown in FIG. 16c), an edible wax is applied to the shell that forms a hard outer surface that can dry or set to have a touchable surface that is not sticky to the touch when cooled (e.g., to room temperature). As a result, the enclosed transport system and shell can generally be handled for consumption. In another example (shown in FIG. 16c), alternatively or additionally, a sealing substance (e.g., oil) is applied to the inner surfaces of the shell portions. The oil can absorb into the shell and reduce the likelihood that moisture will pass through the shell. In some embodiments, the shell is pre-treated with the oil applied to the inner surfaces of the shell).

These types of shells can help preserve the structural integrity and flavors of the transport systems that they enclose. In this example, both the waffle cone bowl covered in wax and the waffle cone bowl with oil applied were tested relative to one another. Similar transport systems were prepared and enclosed in each of the two waffle bowl shells. One of the shells was treated with oil and the other shell had a wax coating applied. The two shells were exposed to environmental tests and the waffle bowl coated in wax was shown to preserve the structural and flavor characteristics of the pear flavored transport system longer than a similar transport system enclosed in the waffle bowl treated with oil.

Example 4—Barrier Layers Between Shells and Membranes

Figure 17A:
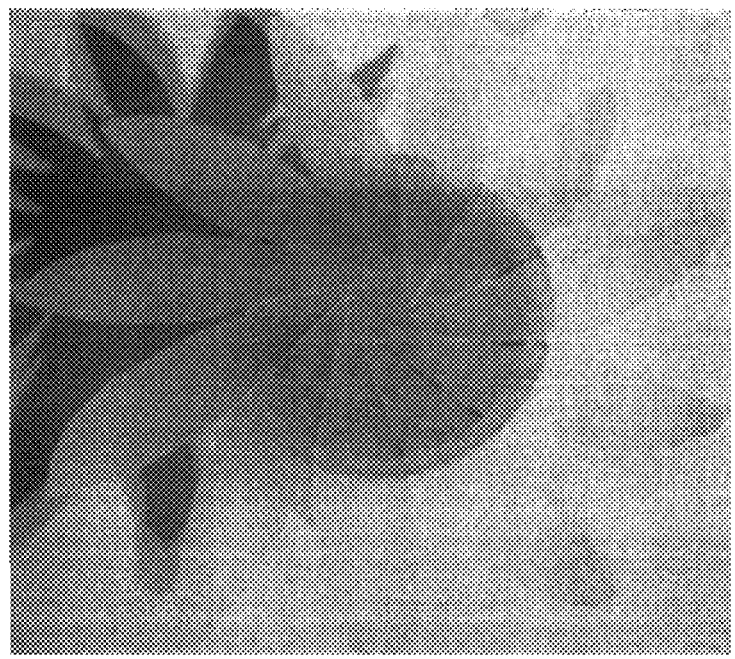
Figure 17B:
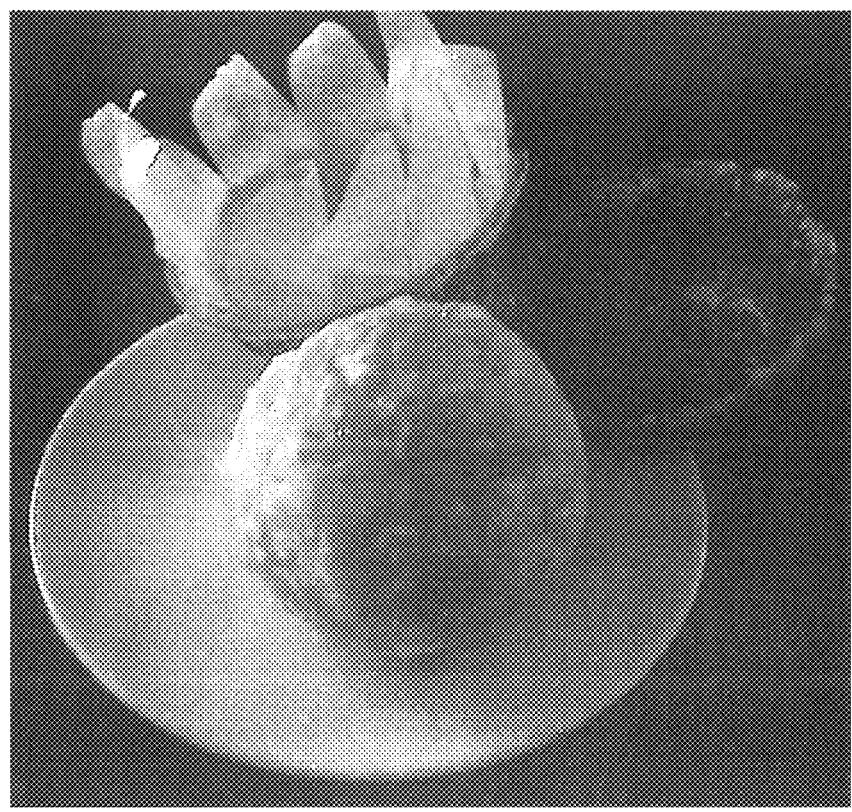
Figure 17C:
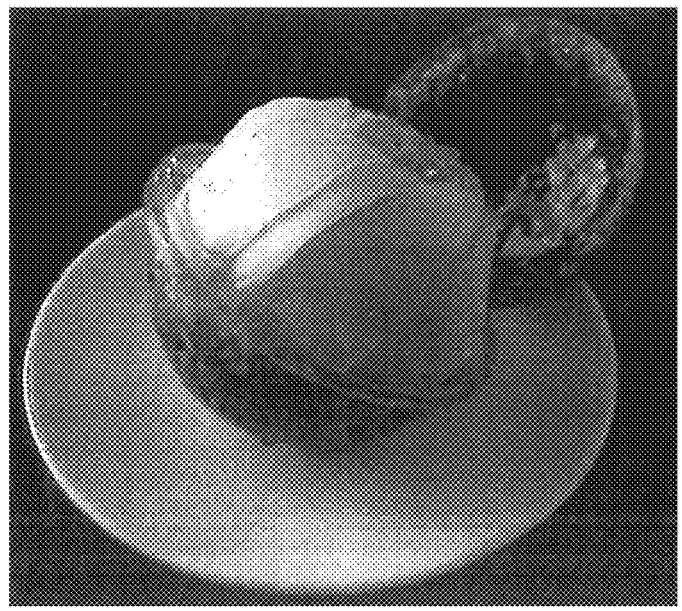
Figure 17D:
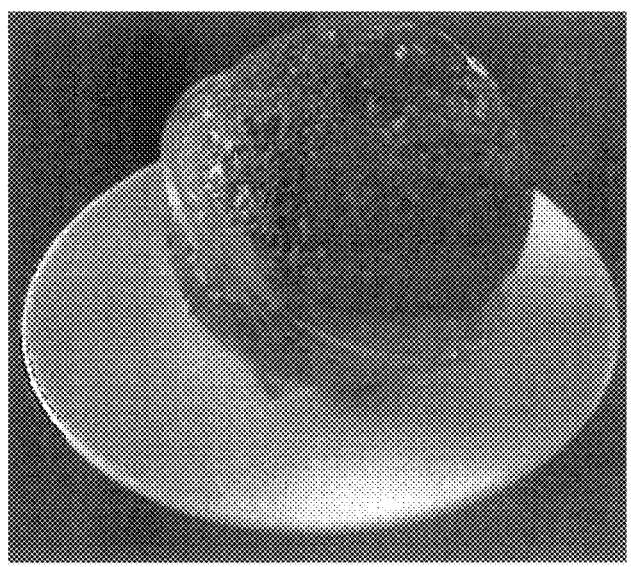

In some embodiments, a barrier layer is arranged between the membrane layer of the natural transport system and the shell. Barrier layers can be made of various materials (e.g., wax paper, thin plastic, caramel, or edible waxes) to help (i) reduce the evaporation of materials from the inner membrane or its contents; (ii) sequester degradation products of the inner membrane or its contents; and/or (iii) reduce the likelihood that the membrane layer substantially sticks to or becomes bonded with the shell during storage or transportation. This can further protect, and increase the longevity, of the outer shell. By way of an example, FIGS. 17a-17d illustrate packaging a transport system into a shell with a barrier layer between the membrane layer of the transport system and the shell. FIG. 17a shows a piece of wax paper cut into a pattern placed on top of a bottom half of a shell. The wax paper pattern is formed so that the wax paper can conform to the substantially spherical inner surfaces of the shell. FIG. 17b shows the wax paper inserted down into the bottom half of the shell. With the wax paper inserted into the bottom half of the shell, the transport system can be placed into the bottom half of the shell inside the wax paper. As shown in FIG. 17c, with the transport systems inside the wax paper, upper portions of the wax paper can be wrapped onto and around an upper portion of the transport systems, which substantially surrounds the membrane layer with the wax paper. With the wax paper surrounding the transport system, a top half of the shell can be placed onto the bottom half of the shell to enclose the transport system. As shown in FIG. 17d, the top half can be placed on and attached to the bottom half. In this particular embodiment, the shell is made of isomalt, and the two molded portions can be attached to each other by humidifying (e.g., adding small amounts of water) to the edges to be attached; this causes the isomalt to become sticky, and the two portions can be thus secured together. Another example of how such portions may be attached is by adding a separate amount of melted isomalt. Similar techniques can be used for other shells, such as caramel shells. By way of another example, referring to FIG. 18, a transport system can also be packaged in a wafer, waffle-like material. In such systems, a barrier layer may be particularly useful.

Example 6—Systems for Producing Transport Systems

Figure 18:
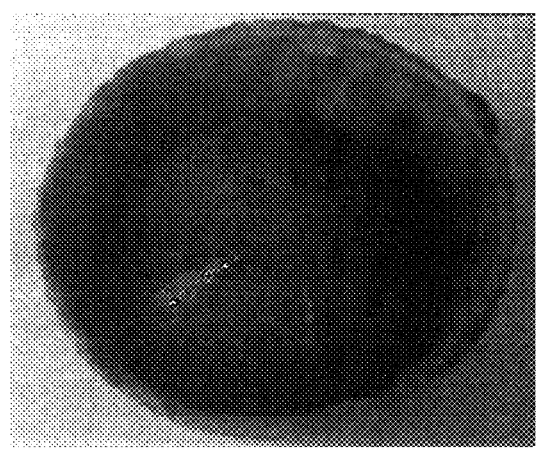
Figure 19:
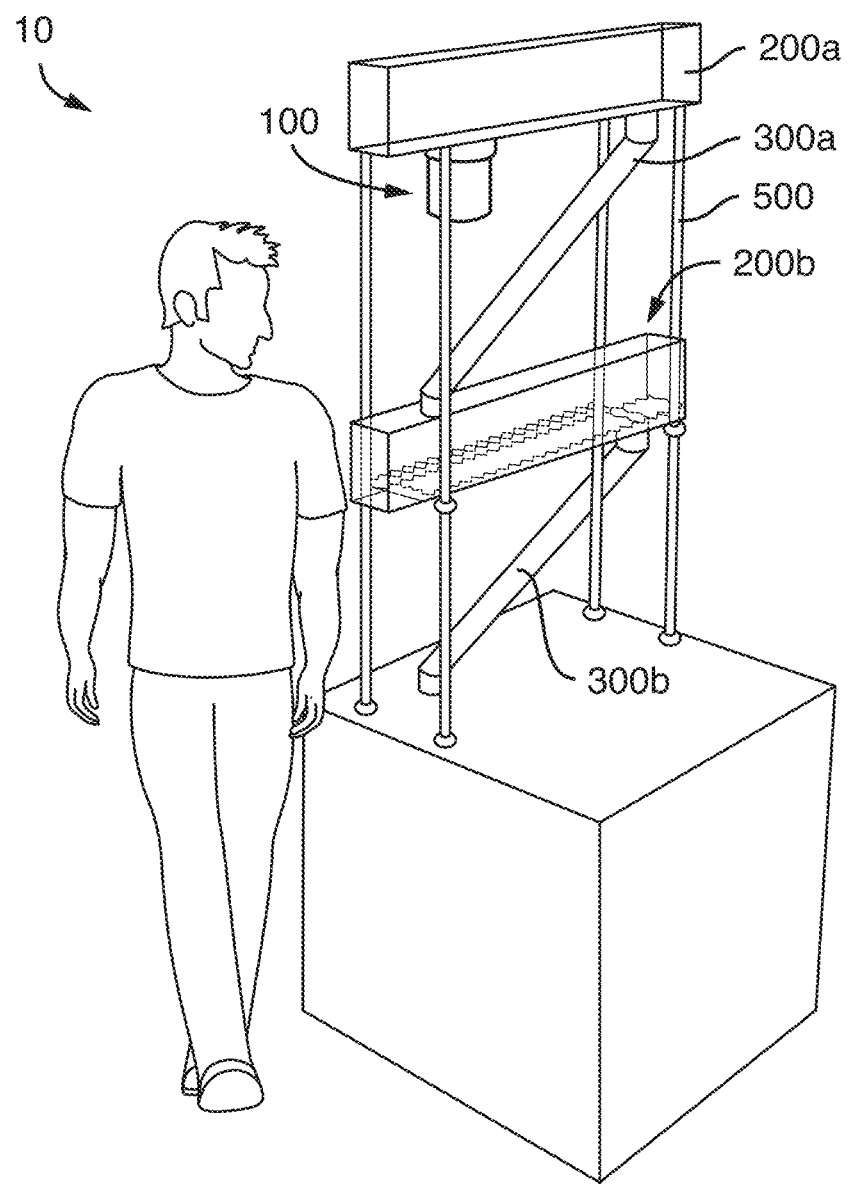

FIG. 18 is a perspective view of an exemplary fluid enclosing system 10 for coating objects to form natural transport systems. The fluid enclosing system 10 includes a fluid delivery apparatus 100, and at least one reactor module 200 for coating an object (e.g., a frozen object) with a membrane layer. Other details and disclosure about the fluid enclosing system 10 can be found in International Publication Number WO 2011/103594 A1, the contents of which are hereby incorporate by reference in their entirety.

Figure 20:
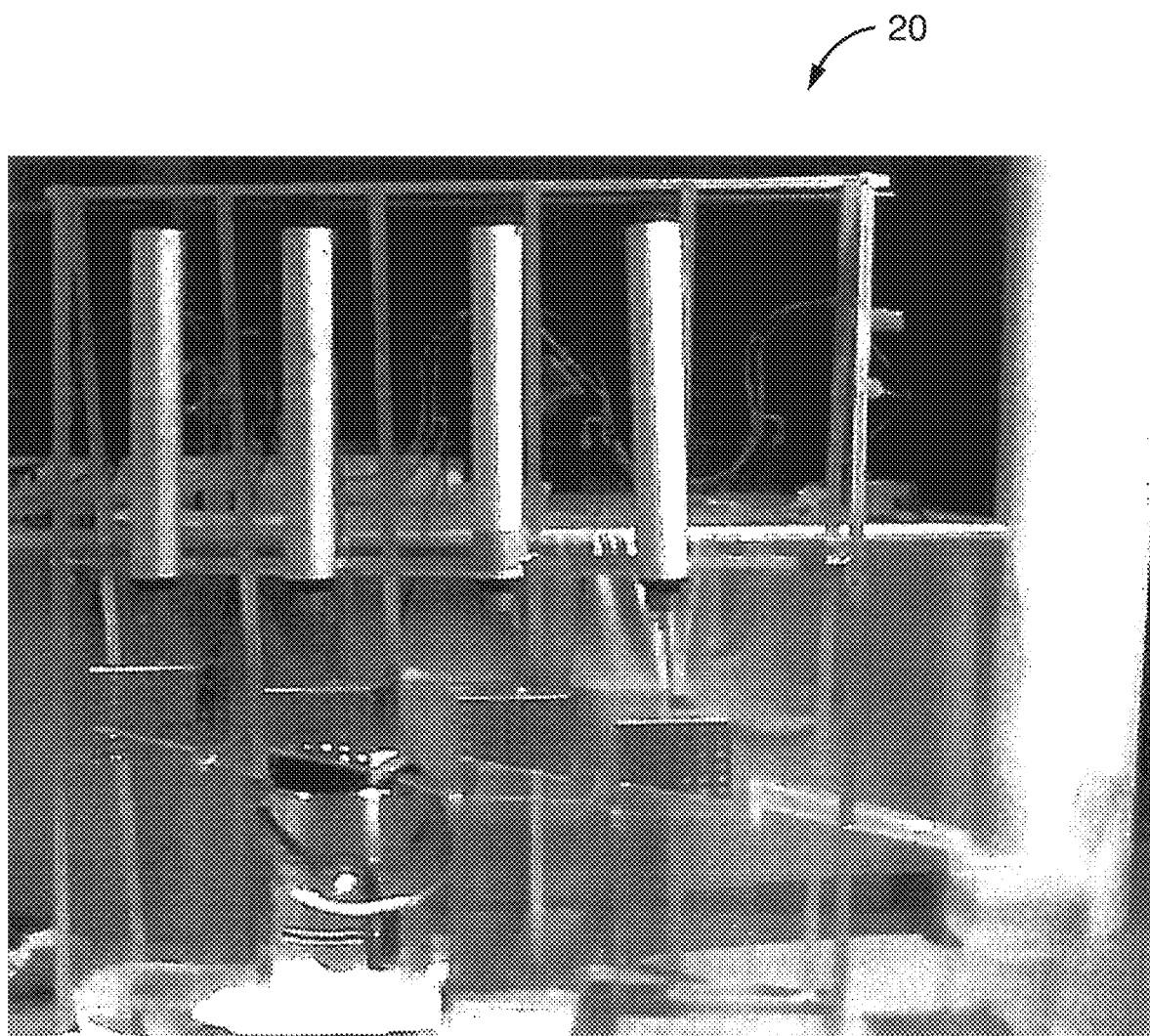

FIG. 20 is a front view of another exemplary fluid enclosing system 20 for coating objects to form natural transport systems. The fluid enclosing system 20 includes multiple processing stations in which an object (e.g., a frozen object) is raised and lowered into multiple fluid baths. The object is lowered into the multiple fluid baths to enclose the object in a membrane layer. Other details and disclosure about the fluid enclosing system 20 can be found in U.S. Provisional Patent Application 61/591,225, filed on Jan. 26, 2012, U.S. Provisional Patent Application 61/601,866, filed on Feb. 22, 2012, U.S. Provisional Patent Application contents of which are incorporated herein by reference in their entirety. Other related details and disclosures can be found in U.S. Provisional Patent Application 61/591,054, filed on Jan. 26, 2012, U.S. Provisional Patent Application 61/591,233, filed on Jan. 26, 2012, U.S. Provisional Patent Application 61/591,262, filed on Jan. 26, 2012, U.S. Provisional Patent Application 61/601,852, filed on Feb. 22, 2012, U.S. Provisional Patent Application 61/647,721, filed on May 16, 2012, U.S. Provisional Patent Application 61/713,138 filed on Oct. 12, 2012, U.S. Provisional Patent Application 61/713,100 filed on Oct. 12, 2012, and U.S. Provisional Patent Application 61/713,063 filed on Oct. 12, 2012, contents of which are incorporated herein by reference in their entirety.

Example 7—Compositions and Recipes of the Transport System

Membrane layer and inner liquid compositions to be used in the transport systems shown, e.g., in FIGS. 9-13 can include various ingredients to achieve different results (e.g., different flavors or textures) based on the requirements or needs of the intended end user. Several examples of membrane layer compositions and liquids to be enclosed by membrane are provided below.

In some embodiments, transport systems are made from various ingredients to be consumed as a food product (e.g., as a component in a meal or a dessert). Examples of membrane layer compositions and corresponding liquids to be enclosed by the membrane are provided in the tables below.

Example 7A—Compositions and Recipes: Cocktails/Alcohol Beverages

In some embodiments, transport systems are comprised of various ingredients of an alcohol beverage (e.g., a cocktail). Examples of membrane layer compositions and corresponding cocktail beverages to be enclosed by the membrane are provided in the tables below. While certain combinations of membranes and inner liquids are provided herein, other combinations are possible, or neat solutions of alcohol drinks are possible. Membrane transport systems with the following ingredients and formulations may be constructed as described or with alternative methods of preparation as described herein.

TABLE 7.1A

Kir Cocktail
Inner Liquid

| Ingredient | Mass per 1000 g |
|---|---|
| Blackberry Liqueur | 400 g |
| Apple Grape Blackcurrant Juice | 600 g |

TABLE 7.1B

Membrane

| Ingredient | Mass per 1000 g |
|---|---|
| Sodium Alginate (1.5% solution) | 878 g |
| Sugar | 120 g |
| Apple Flavoring (e.g., from Givaudan company) | 2 g |

TABLE 7.2A

1084 Cocktail
Inner Liquid

| Ingredient | Mass per 1000 g |
|---|---|
| Triple sec (e.g., Cointreau) | 188 g |
| Cranberry Juice | 250 g |
| Grapefruit Juice | 312 g |
| Strawberry Syrup | 250 g |

TABLE 7.2B

Membrane

| Ingredient | Mass per 1000 g |
|---|---|
| Sodium Alginate (1.5% solution) | 778 g |
| Sugar | 120 g |
| Strawberry Syrup (e.g., Teissere brand) | 100 g |
| Strawberry Flavoring (e.g., from Firmenich company) | 2 g |

TABLE 7.3A

Blue Monster Cocktail
Inner Liquid

| Ingredient | Mass per 1000 g |
|---|---|
| Triple sec (e.g., Cointreau) | 150 g |
| Curacao | 100 g |
| Schweppes | 750 g |

TABLE 7.3B

Membrane

| Ingredient | Mass per 1000 g |
|---|---|
| Sodium Alginate (1.5% solution) | 812 g |
| Sugar | 120 g |
| Orange peel from non-treated (natural) oranges | 50 g |
| Sodium Citrate | 3 g |

TABLE 7.4A

Vodka Cocktail
Inner Liquid

| Ingredient | Mass per 1000 g |
|---|---|
| Vodka (e.g., Grey Goose) | 400 g |
| Water | 350 g |
| Amaretto | 750 g |
| Creme Cacao | 80 g |
| Caramel liquor | 40 g |

TABLE 7.4B

Membrane

| Ingredient | Mass per 1000 g |
|---|---|
| Sodium alginate (1.5% solution) | 980 g |
| Powder of *vanilla* beans | 5 g |

TABLE 7.5A

Plain Parroquet Cocktail
Inner Liquid

| Ingredient | Mass per 1000 g |
|---|---|
| Ricard (Pernot Ricard) | 250 g |
| Water | 750 g |

TABLE 7.5B

Membrane

| Ingredient | Mass per 1000 g |
|---|---|
| Sodium alginate (1.5% solution) | 770 g |
| Sugar | 50 g |
| Green Mint Syrup | 140 g |
| Frozen Mint Syrup | 40 g |

TABLE 7.6A

Fruity Cocktail
Inner Liquid

| Ingredient | Mass per 1000 g |
|---|---|
| Blackberry Liquor | 50 g |
| Grapefruit Vodka | 300 g |
| Sprite | 400 g |
| Orange Juice | 250 g |

TABLE 7.6B

Membrane

| Ingredient | Mass per 1000 g |
|---|---|
| Sodium alginate (1.5% solution) | 827 g |
| Sugar | 120 g |
| Orange Peel | 50 g |
| Sodium Citrate | 3 g |

TABLE 7.7A

Pina Colada
Inner Liquid

| Ingredient | Mass per 1000 g |
|---|---|
| Pineapple Juice | 460 g |
| Coconut Liquor | 300 g |
| Rum | 240 g |

TABLE 7.7B

Membrane

| Ingredient | Mass per 1000 g |
|---|---|
| Sodium alginate (1.5% solution) | 870 g |
| Sugar | 80 g |
| Grated coconut | 50 g |

TABLE 7.8A

Ladies Cocktail
Inner Liquid

| Ingredient | Mass per 1000 g |
|---|---|
| Vodka | 300 g |
| Cranberry Juice | 400 g |
| Lime Syrup | 50 g |
| Raspberry Syrup | 100 g |
| Lime Juice | 70 g |
| Contreau | 80 g |

TABLE 7.8B

Membrane

| Ingredient | Mass per 1000 g |
|---|---|
| Sodium alginate (1.5% solution) | 876 g |
| Sugar | 80 g |
| Grated lime peel | 40 g |
| Sodium Citrate | 4 g |

TABLE 7.9A

Irish Coffee Cocktail
Inner Liquid

| Ingredient | Mass per 1000 g |
|---|---|
| Water | 432 g |
| Lyophilized coffee | 18 g |
| Whiskey | 300 g |
| Coffee Liquor | 180 g |
| Sugar | 70 g |

TABLE 7.9B

Membrane

| Ingredient | Mass per 1000 g |
|---|---|
| Sodium alginate (1.5% solution) | 880 g |
| Maple Syrup | 120 g |

TABLE 7.10A

Tiramisu
Inner Liquid

| Ingredient | Mass per 1000 g |
|---|---|
| Coffee | 600 g |
| Amaretto | 200 g |
| Sugar Syrup (e.g., simple syrup) | 200 g |

TABLE 7.10B

Membrane

| Ingredient | Mass per 1000 g |
|---|---|
| Sodium Alginate | 15 g |
| Sugar | 120 g |
| Cocoa Powder | 60 g |
| Water | 1 Liter |

Example 7B—Compositions and Recipes: Beverages

In some embodiments, transport systems are comprised of various ingredients to be flavored like a beverage (e.g., soft drinks, energy drinks, juice, coffee/tea). Examples of membrane layer compositions and corresponding beverages to be enclosed by the membrane are provided in the tables below. While certain combinations of membranes and inner liquids are provided together, other combinations are possible, or neat solutions of beverage drinks are possible. Membrane transport systems with the following ingredients and formulations may be constructed as described or with alternative methods of preparation as described herein.

TABLE 7.11A

Cucumber Drink
Inner Liquid

| Ingredient | Mass per 1000 g |
|---|---|
| Cucumber flavoring | 2 g |
| Water | 998 g |

TABLE 7.11B

Membrane

| Ingredient | Mass per 1000 g |
|---|---|
| Sodium alginate (1.5% solution) | 968 g |
| Sodium citrate | 2 g |
| Grated Cucumber Skin | 30 g |

TABLE 7.12A

Black Forest Dessert
Inner Liquid

| Ingredient | Mass per 1000 g |
|---|---|
| Dark Chocolate | 400 g |
| Cherry Syrup | 200 g |
| Kirsch | 100 g |
| Water | 300 g |

TABLE 7.12B

| Membrane | |
|---|---|
| Ingredient | Mass per 1000 g |
| Sodium Alginate | 15 g |
| Sugar | 120 g |
| Concentrated Cherry Juice | 100 g |
| Cherry Flavoring (e.g., from AM Todd company) | 2 g |
| Water | 1 Liter |
| Sodium Citrate | 5 g |

TABLE 7.13A

| Orange Juice Inner Liquid | |
|---|---|
| Ingredient | Mass per 1000 g |
| Orange Juice | 432 g |

TABLE 7.13B

| Membrane | |
|---|---|
| Ingredient | Mass per 1000 g |
| Sodium alginate (1.5% solution) | 827 g |
| Sugar | 120 g |
| Orange Peel | 50 g |
| Sodium Citrate | 3 g |

TABLE 7.14A

| Coffee Drink I Inner Liquid | |
|---|---|
| Ingredient | Mass per 1000 g |
| Liquid Coffee extract | 70 g |
| Sugar | 80 g |
| Liquid cream, 35% fat | 520 g |
| Whole milk | 330 g |

TABLE 7-14B

| Membrane | |
|---|---|
| Ingredient | Mass per 1000 g |
| Sodium alginate (1.5% solution) | 830 g |
| Cacao powder | 80 g |
| Sugar | 90 g |

TABLE 7.15A

| Coffee Drink II Inner Liquid | |
|---|---|
| Ingredient | Mass per 1000 g |
| Dried Coffee powder | 40 g |
| Sugar | 80 g |
| Liquid cream, 35% fat | 550 g |
| Whole milk | 330 g |

TABLE 7.15B

| Membrane | |
|---|---|
| Ingredient | Mass per 1000 g |
| Sodium alginate (1.5% solution) | 830 g |
| Cacao powder | 80 g |
| Sugar | 90 g |

TABLE 7.16A

| Almond Membrane with Pear Juice Inner Liquid | |
|---|---|
| Ingredient | Mass per 1000 g |
| «Nectar de poire» (e.g. mix of pear syrup, juice, puree, sugar, and/or water) | 1000 g |

TABLE 7.16B

| Membrane | |
|---|---|
| Ingredient | Mass per 1000 g |
| Sodium Alginate | 15 g |
| Sugar | 120 g |
| Cookie/Biscuit Flavoring (e.g., from Givaudan company) | 2 g |
| Powdered almond | 60 g |
| Water | 1 Liter |

TABLE 7.17A

| Lemonade in Lemon Membrane Inner Liquid | |
|---|---|
| Ingredient | Mass per 1000 g |
| Lemonade/Lemon Juice (e.g., from Minute Maid ®) or squeezed-lemon juice, e.g. from Andros) | 1000 g |

TABLE 7.17B

| Membrane (sodium alginate) | |
|---|---|
| Ingredient | Mass per 1000 g |
| Sodium Alginate | 15 g |
| Sodium Citrate (optional) | 5 g |
| Powdered Sugar | 120 g |
| Peels of 6 untreated (natural) lemons | |
| Mineral Water | 1 Liter |

TABLE 7.17C

| Membrane (calcium lactate) | |
|---|---|
| Ingredient | Mass per 1000 g |
| Calcium lactate | 20 g |
| Water | 1 Liter |

TABLE 7.17D

| Rinsing Solution | |
| --- | --- |
| Ingredient | Mass per 1000 g |
| Pulp and juice of 6 lemons | |
| Water | 1 Liter |
| A few drops of food coloring, e.g. yellow E102 | |

Method of preparation for lemon: Before creating the transport system (e.g., 24 hours before), freeze the lemon inner liquid into molds to form balls having a diameter of about 4 to 5 cm. Set aside in freezer.

In a pot, combine the sodium alginate and mineral water, then heat over a low heat until it simmers. Remove from heat and combine the prepared sodium alginate solution with the sugar and the lemon peels. Place in a blender and blend until homogeneous. Keep refrigerated.

Prepare the calcium solution by mixing 20 g of calcium lactate with 1 liter of water, and place this solution in two separate containers.

In another container, prepare the rinse solution by mixing 1 liter of water, the pulp and juice of 6 lemons, and the few drops of yellow food coloring (e.g., E102).

Place the liquid nitrogen in a suitable container.

Remove the lemon ice cubes from the freezer.

Dip one of the lemon ice cubes into the liquid nitrogen for 1-60 seconds and then dip it into the first container of calcium solution for 1-60 seconds.

Remove the ice cube from the calcium solution and dip it back into the liquid nitrogen for 1-60 seconds and then into the calcium solution for 1-60 seconds.

Dip the ice cube again in liquid nitrogen for 1-60 seconds and then place it in the alginate solution.

After 1-60 seconds, gently remove the ice cube from the alginate solution and place it in the second container of calcium solution. Leave the ice cube in the calcium solution for 1-60 minutes, then gently remove the ice cube from the calcium solution and place it in the rinse solution. From the rinse solution, the transport system can be packaged or stored (e.g., in a shell) and placed in a refrigerator or freezer. Alternatively, the transport system can be allowed to thaw and prepared for consumption.

Example 7C—Compositions and Recipes: Food Products

Membrane layer and inner liquid compositions to be used in the transport systems can include various ingredients to achieve different results (e.g., different flavors or textures) based on the requirements or needs of the intended end user. Several examples of membrane layer compositions and payloads to be enclosed by a membranous transport system are provided below.

In some embodiments, transport systems are made from various ingredients to be consumed as a food product (e.g., as a component in a meal or a dessert). Examples of membrane layer compositions and corresponding payloads to be enclosed by the membrane are provided in the tables below. Membrane transport systems with the following ingredients and formulations may be prepared as described or with alternative methods of preparation as described herein. Ice cream, cheese, mousse, etc. is made using methods known to those in the art using the ingredients exemplified in the tables described herein, or ice cream, cheese, etc. is available through commercial venues.

TABLE 7.18A

| Tomato Juice in Basil or Spinach Membrane Inner Liquid | |
| --- | --- |
| Ingredient | Mass per 1000 g |
| Tomato Juice or Soup | 1000 g |

TABLE 7.18B

| Membrane (sodium alginate) | |
| --- | --- |
| Ingredient | Mass per 1000 g |
| Sodium Alginate | 15 g |
| Sodium Citrate (optional) | 5 g |
| Salt and pepper | Pinch |
| Fresh Basil (or Spinach) | Bunch |
| Mineral Water | 1 Liter |

TABLE 7.18C

| Membrane (calcium lactate) | |
| --- | --- |
| Ingredient | Mass per 1000 g |
| Calcium Lactate | 20 g |
| Water | 1 Liter |

TABLE 7.18D

| Rinsing Solution | |
| --- | --- |
| Ingredient | Mass per 1000 g |
| Fresh Basil (or Spinach) Leaves | |
| Water | 1 Liter |

Method of preparation for tomato: Before creating the transport system (e.g., 24 hours before), freeze the tomato juice or soup into molds to form balls each having a diameter of about 4 to 5 cm. Set balls aside in freezer.

In a pot, combine the sodium alginate and water, and heat over low heat until it simmers. Remove from heat and combine the prepared sodium alginate solution with the salt, pepper, and basil (or spinach). Place in a blender, then blend until homogeneous. Keep refrigerated.

Prepare two calcium solutions by mixing 20 g of calcium lactate and 1 liter of water, and placing the solution in two different containers.

In another container, prepare the rinse solution by mixing 1 liter of water and additional basil (or spinach) leaves.

Place the liquid nitrogen in an appropriate container.

Remove the tomato ice cubes from the freezer.

Dip one of the tomato ice cubes in liquid nitrogen for 1-60 seconds and then dip it in the first container of calcium solution for 1-60 seconds. Remove the ice cube from the calcium solution and dip it back into the liquid nitrogen for 1-60 seconds and then into the calcium solution for 1-60 seconds. Dip the ice cube again in liquid nitrogen for 1-60 seconds and then place it in the alginate solution.

After 1-60 seconds, gently remove the ice cube from the alginate solution and place it in the second container of calcium solution. Leave the ice cube in the calcium solution for 1-60 minutes, then gently remove the ice cube from the calcium solution and place it in the rinse solution. From the rinse solution, the transport system can be packaged or stored (e.g., in a shell) and placed in a refrigerator or freezer. Alternatively, the transport system can be allowed to thaw and prepared for consumption.

While certain combinations of membranes and inner liquids have been provided and described as being used together, other combinations are possible. For example, the basil or spinach membrane can enclose pumpkin soup instead of tomato soup.

TABLE 7.19A

Chocolate Mousse
Membrane (calcium lactate)

| Ingredient | Mass per 1000 g |
|---|---|
| Alginate (1.5% solution) | 935 g |
| *Cacao* powder | 65 g |

TABLE 7.19B

Inner composition

| Ingredient | Mass per 1000 g |
|---|---|
| Chocolate mousse | 1000 g |

TABLE 7.20A

Hazelnut-chocolate ice cream
Inner composition

| Ingredient | Mass per 1000 g |
|---|---|
| Sugar | 93 g |
| Liquid cream, 30% fat | 520 g |
| Whole milk | 120 g |
| *Cacao* powder | 30 g |
| Dark chocolate | 250 g |

TABLE 7.20B

Membrane

| Ingredient | Mass per 1000 g |
|---|---|
| Sodium alginate (1.5% solution) | 720 g |
| *Cacao* butter | 75 g |
| Sugar | 93 g |
| Hazelnut powder | 112 g |

TABLE 7.20A

Hazelnut-chocolate ice cream
Inner composition

| Ingredient | Mass per 1000 g |
|---|---|
| Sugar | 93 g |
| Liquid cream, 30% fat | 520 g |
| Whole milk | 120 g |
| *Cacao* powder | 30 g |
| Dark chocolate | 250 g |

TABLE 7.20B

Membrane

| Ingredient | Mass per 1000 g |
|---|---|
| Sodium alginate (1.5% solution) | 720 g |
| *Cacao* butter | 75 g |
| Sugar | 93 g |
| Hazelnut powder | 112 g |

TABLE 7.21A

Coco-chocolate ice cream
Inner composition

| Ingredient | Mass per 1000 g |
|---|---|
| Sugar | 80 g |
| Liquid cream, 30% fat | 520 g |
| Whole milk | 120 g |
| *Cacao* powder | 30 g |
| Dark chocolate | 250 g |

TABLE 7.21B

Membrane

| Ingredient | Mass per 1000 g |
|---|---|
| Sodium alginate (1.5% solution) | 520 g |
| Creme of coconut | 230 g |
| Sugar | 80 g |
| Coconut powder | 180 g |

TABLE 7.22A

Cookie dough *vanilla* ice cream
Inner composition

| Ingredient | Mass per 1000 g |
|---|---|
| Sugar | 140 g |
| Liquid cream, 35% fat | 660 g |
| Whole milk | 128.8 g |
| *Vanilla* bean | 0.9 g |
| *Vanilla* extract | 0.3 g |

TABLE 7.22B

Membrane

| Ingredient | Mass per 1000 g |
|---|---|
| Sodium alginate (1.5% solution) | 660 g |
| Speculos cream | 40 g |
| Speculos powder | 40 g |
| Chocolate chips | 100 g |
| Fine chocolate flakes | 70 g |
| Sugar | 90 g |

TABLE 7.23A

Hazelnut-chocolate ice cream
Inner composition

| Ingredient | Mass per 1000 g |
|---|---|
| Sugar | 99.6 g |
| Mango puree | 900 g |

TABLE 7.23A-continued

Hazelnut-chocolate ice cream
Inner composition

| Ingredient | Mass per 1000 g |
|---|---|
| Citric acid + water (50%/50%) | 0.2 g |
| Natural flavoring powder | 0.2 g |

TABLE 7.23B

Membrane

| Ingredient | Mass per 1000 g |
|---|---|
| Sodium alginate (1.5% solution) | 490 g |
| Cream of coconut | 270 g |
| Sugar | 60 g |
| Coconut powder | 180 g |

TABLE 7.24A

**Chocolate fudge *vanilla* ice cream**
Inner composition

| Ingredient | Mass per 1000 g |
|---|---|
| Sugar | 140 g |
| Liquid cream, 35% fat | 660 g |
| Whole milk | 128.8 g |
| *Vanilla* bean | 0.9 g |
| *Vanilla* extract | 0.3 g |

TABLE 7.24B

Membrane

| Ingredient | Mass per 1000 g |
|---|---|
| Sodium alginate (1.5% solution) | 126.4 g |
| Dark chocolate | 105.2 g |
| Milk chocolate | 692.4 g |
| Natural cacao flavor (Pova, Inc.) | 1.05 g |
| Cacao flavor (Givaudin, Inc.) | 1.25 g |
| Sugar | 73.7 g |

TABLE 7.25A

Hazelnut Honey Cheese
Membrane

| Ingredient | Mass per 1000 g |
|---|---|
| Alginate (1.5% solution) | 740 g |
| Hazelnut powder | 130 g |
| Honey | 130 g |

TABLE 7.25B

Inner composition

| Ingredient | Mass per 1000 g |
|---|---|
| Goat's cheese | 1000 g |

TABLE 7.26A

Curry Cheese
Membrane

| Ingredient | Mass per 1000 g |
|---|---|
| Alginate (1.5% solution) | 948 g |
| Ground curry | 14 g |
| Turmeric | 10 g |
| Poppy seeds | 28 g |

TABLE 7.26B

Inner composition

| Ingredient | Mass per 1000 g |
|---|---|
| Kiri Goat's cheese | 97.6 g |
| Salt | 2.4 g |

TABLE 7.27A

Cumin Cheese
Membrane

| Ingredient | Mass per 1000 g |
|---|---|
| Alginate (1.5% solution) | 968 g |
| Ground cumin | 29 g |
| Sodium citrate | 3 g |

TABLE 7.27B

Inner composition

| Ingredient | Mass per 1000 g |
|---|---|
| Kiri Goat's cheese | 97.6 g |
| Salt | 2.4 g |

TABLE 7.28A

Herbs & Garlic Cheese
Membrane

| Ingredient | Mass per 1000 g |
|---|---|
| Alginate (1.5% solution) | 976 g |
| Chopped garlic | 14 g |

TABLE 7.28B

Inner composition

| Ingredient | Mass per 1000 g |
|---|---|
| Kiri Goat's cheese | 976 g |
| Salt | 24 g |
| Dried parsley + Dried basil, 50%/50% | A serving of cheese + salt is rolled into this powder mixture |

TABLE 7.29A

Onion & Cherry Tomato Cheese Membrane

| Ingredient | Mass per 1000 g |
|---|---|
| Alginate (1.5% solution) | 945.5 g |
| Sodium citrate | 3 g |
| Dried onion | 50 g |
| Salt | 1 g |
| Ground pepper | 0.5 g |

TABLE 7.29B

Inner composition

| Ingredient | Mass per 1000 g |
|---|---|
| Kiri Goat's cheese | 1000 g |
| Dried cherry tomato powder | A serving of cheese is rolled into powder |

TABLE 7.30A

Beetroot and sweet red pepper cheese Membrane

| Ingredient | Mass per 1000 g |
|---|---|
| Alginate (1.5% solution) | 995 g |
| Sodium citrate | 3 g |
| Salt | 1.5 g |
| Ground pepper | 0.5 g |

TABLE 7.30B

Inner composition

| Ingredient | Mass per 1000 g |
|---|---|
| Kiri Goat's cheese | 1000 g |
| Beetroot powder + ground sweet red pepper (50%/50%) | A serving of cheese is rolled into powder mixture |

Example 8: Multi-Membrane Transport Systems

Multimembrane transport systems can be provided with two or more membranes encasing an inner product. Variations of a multimembrane transport systems exemplified below include an ingestible powder product rolled onto the surface of an inner membrane, followed by subjecting the transport system to at least one additional membrane forming process. Membrane transport systems with the following ingredients and formulations may be prepared as described or with alternative methods of preparation as described herein.

Example 8A: Double Membrane Transport Systems

TABLE 8.1A

Vanilla Cream Double Layer Inner Substance

| Ingredient | Mass per 1000 g |
|---|---|
| Yogurt | 926 g |
| Sugar | 74 g |

TABLE 8.1B

Inner Membrane

| Ingredient | Mass per 1000 g |
|---|---|
| 1.5% Alginate base | 980 g |
| Sugar | 20 g |

TABLE 8.1C

Powder Layer

| Ingredient | Mass per 1000 g |
|---|---|
| Vanilla Powder | 150 g |
| Mascarpone Powder | 850 g |

TABLE 8.1D

Outer Membrane

| Ingredient | Mass per 1000 g |
|---|---|
| 1.5% Alginate Base | 934 g |
| Sugar | 66 g |

In a pot, combine the 15 g sodium alginate and into 985 g of mineral water, then heat over a low heat until it simmers. Mix until alginate is completely dissolved and solution has a uniform consistency. Let set at 4 C for 2-3 hours. Add Sugar and mix to a uniform consistency. Prepare a 2% calcium bath by mixing 20 g of calcium lactate with 1 liter water. Dissolve completely. To alginate mixture for skin 1, add 100 g of powder to be used additionally for the powder layer, and mix to a uniform blend. Blend yogurt and sugar to consistent texture, and add to a pastry bag, piping bag or similar device. Dip end of pastry bag into inner membrane alginate solution, and form small spheres of 1-2 inch diameter. Remove spheres from inner membrane alginate solution and place into calcium bath for 10-15 minutes. Remove spheres and dry the surface with absorbing paper. Cover spheres with powder for the powder layer by rolling or with any other appropriate method, and dip into outer membrane alginate solution, followed by placement into calcium bath for 10-15 minutes. Store at 4 C.

TABLE 8.2A

Green Mint-Green Peas Double Layer Inner Substance

| Ingredient | Mass per 1000 g |
|---|---|
| Yogurt | 926 g |
| Sugar | 74 g |

TABLE 8.2B

Inner, Outer Membranes

| Ingredient | Mass per 1000 g |
|---|---|
| 1.5% Alginate base | 970 g |
| Sugar | 30 g |

TABLE 8.2C

| Powder Layer | |
| --- | --- |
| Ingredient | Mass per 1000 g |
| Green mint powder | 40 g |
| Green peas powder | 960 g |

TABLE 8.3A

| Cinnamon Cream Double Layer Inner Substance | |
| --- | --- |
| Ingredient | Mass per 1000 g |
| Yogurt | 926 g |
| Sugar | 74 g |

TABLE 8.3B

| Inner, Outer Membranes | |
| --- | --- |
| Ingredient | Mass per 1000 g |
| 1.5% Alginate base | 970 g |
| Sugar | 30 g |

TABLE 8.3C

| Powder Layer | |
| --- | --- |
| Ingredient | Mass per 1000 g |
| Cinnamon powder | 150 g |
| Cream powder | 850 g |

TABLE 8.4A

| Raspberry Beetroot Cherry Tomato Double Layer Inner Substance | |
| --- | --- |
| Ingredient | Mass per 1000 g |
| Yogurt | 926 g |
| Sugar | 74 g |

TABLE 8.4B

| Inner, Outer Membranes | |
| --- | --- |
| Ingredient | Mass per 1000 g |
| 1.5% Alginate base | 970 g |
| Sugar | 30 g |

TABLE 8.4C

| Powder Layer | |
| --- | --- |
| Ingredient | Mass per 1000 g |
| Raspberry powder | 500 g |
| Cherry tomato powder | 300 g |
| Beetroot powder | 100 g |
| Sugar powder | 100 g |

TABLE 8.5A

| Milky Lemon Double Layer Inner Substance | |
| --- | --- |
| Ingredient | Mass per 1000 g |
| Yogurt | 926 g |
| Sugar | 74 g |

TABLE 8.5B

| Inner, Outer Membranes | |
| --- | --- |
| Ingredient | Mass per 1000 g |
| 1.5% Alginate base | 970 g |
| Sugar | 30 g |

TABLE 8.5C

| Powder Layer | |
| --- | --- |
| Ingredient | Mass per 1000 g |
| Lemon powder | 900 g |
| Yogurt powder | 100 g |

TABLE 8.6A

| Strawberry Banana Double Layer Inner Substance | |
| --- | --- |
| Ingredient | Mass per 1000 g |
| Yogurt | 926 g |
| Sugar | 74 g |

TABLE 8.6B

| Inner, Outer Membranes | |
| --- | --- |
| Ingredient | Mass per 1000 g |
| 1.5% Alginate base | 970 g |
| Sugar | 30 g |

TABLE 8.6C

| Powder Layer | |
| --- | --- |
| Ingredient | Mass per 1000 g |
| Strawberry powder | 650 g |
| Banana powder | 350 g |

TABLE 8.7A

| Raspberry Double Layer Inner Substance | |
| --- | --- |
| Ingredient | Mass per 1000 g |
| Yogurt | 926 g |
| Sugar | 74 g |

TABLE 8.7B

| Inner, Outer Membranes | |
|---|---|
| Ingredient | Mass per 1000 g |
| 1.5% Alginate base | 970 g |
| Sugar | 30 g |

TABLE 8.7C

| Powder Layer | |
|---|---|
| Ingredient | Mass per 1000 g |
| Raspberry powder | 1000 g |

Example 8B: Triple Membrane Transport Systems

TABLE 8.8A

| Strawberry Triple Membrane Yogurt Inner Substance | |
|---|---|
| Ingredient | Mass per 1000 g |
| Yogurt | 926 g |
| Sugar | 74 g |

TABLE 8.8B

| Inner, Middle, Outer Membranes | |
|---|---|
| Ingredient | Mass per 1000 g |
| 1.5% Alginate base | 934 g |
| Sugar | 66 g |

TABLE 8.8C

| Powder Layer | |
|---|---|
| Ingredient | Mass per 1000 g |
| Strawberry Powder | 1000 g |

Figure 21A:
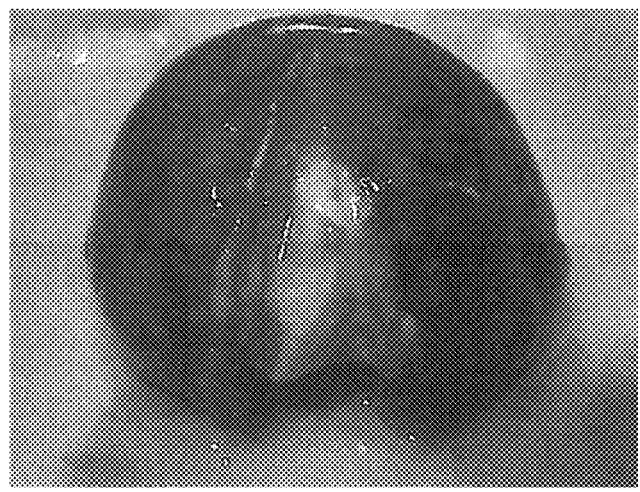
Figure 21B:
Figure 21C:
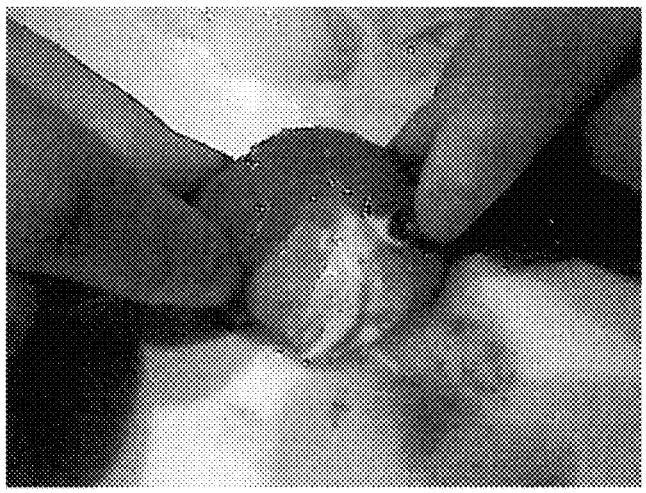

In a pot, combine the 15 g sodium alginate and into 985 g of mineral water, then heat over a low heat until it simmers. Mix until alginate is completely dissolved and solution has a uniform consistency. Let set at 4 C for 2-3 hours. Add sugar and mix until uniform consistency. Prepare a 2% calcium bath by mixing 20 g of calcium lactate with 1 liter water. Dissolve completely. Blend yogurt and sugar to consistent texture, and add to a pastry bag, piping bag or similar device. Dip end of pastry bag into inner membrane alginate solution, and form small spheres of 1-2 inch diameter. Remove spheres from inner membrane alginate solution and place into calcium bath for 10-15 minutes. Remove spheres and dry the surface with absorbing paper. Cover spheres with powder for the powder layer by rolling or with any other appropriate method, and dip into outer membrane alginate solution, followed by placement into calcium bath for 10-15 minutes. Cover spheres a second time with powder for the powder layer by rolling or with any other appropriate method, and dip into outer membrane alginate solution, followed by placement into calcium bath for 10-15 minutes. Store at 4 C. See FIG. 21a-21c.

TABLE 8.9A

| Raspberry Triple Layer Inner Substance | |
|---|---|
| Ingredient | Mass per 1000 g |
| Yogurt | 926 g |
| Sugar | 74 g |

TABLE 8-3B

| Inner, Middle and Outer Membranes | |
|---|---|
| Ingredient | Mass per 1000 g |
| 1.5% Alginate base | 970 g |
| Sugar | 30 g |

TABLE 8-3C

| Powder Layer | |
|---|---|
| Ingredient | Mass per 1000 g |
| Raspberry powder | 1000 g |

EMBODIMENTS

A number of embodiments have been described. Nevertheless, it will be understood that various modifications may be made without departing from the spirit and scope of the invention.

For example, the containers can include ingestible substances contained in a soft membrane; ingestible substances contained in a soft membrane inside a hard edible shell; multiple membrane-enclosed servings disposed in a hard edible shell; and multiple membrane-enclosed servings disposed in a hard biodegradable shell. The exemplary membranes discussed above are generally 5-6 cm, but we have made shells of 7-8 cm and smaller "grape" membranes (1-3 cm) as well.

In some embodiments, containers include a PLA outer shell and use inner membranes ranging from the sodium alginate membranes to edible waxes of the kinds used on fine chocolates occasionally. The latter have a distinct advantage of repelling water. Some embodiments may contain one or more combinations of such materials as "shells" or "membranes", for example, a sodium alginate membrane, hardened/cured with calcium, may be covered with an edible wax and then placed within a PLA shell.

In some embodiments, multiple inner containers can be protected by a single outer shell. For example, in some embodiments, a shell of PLA is filled with 'grapes' of liquid and closed up like a bottle. The outer shell can be opened and the 'grapes' consumed with the liquid they contain. The outer shell is biodegradable and the advantage of the inner membranes is to reduce direct contact of water bottle and water and therefore avoid degradation of the bottle itself.

Selected illustrative embodiments of the machines and compositions are described above in some detail. It should be understood that only the essential machine components, ingredients and/or formulations which are considered necessary for clarifying the exemplified embodiments have been described herein. Other machine components, ingredients and/or formulations equivalents are assumed to be known and understood by those skilled in the art. Moreover, while working examples of machine components, ingredients and/or formulations have been described, the present invention is not limited to the working examples described above, but various design alterations may be carried out without departing from the machine components, ingredients and/or formulations as set forth in the claims.

What is claimed is:

1. An edible composition, comprising:
   an edible substance;
   a first edible polymer membrane encapsulating the edible substance; and
   a second edible polymer membrane encapsulating the first edible polymer membrane,
   wherein the first edible polymer membrane is comprised of at least one different edible polymer than the second edible polymer membrane, and wherein the first edible polymer membrane and the second edible polymer membrane form a melded interface;
   wherein the melded interface comprises an electrostatic attraction between the first edible polymer membrane and the second edible polymer membrane; and wherein the edible substance is fully solid, partially solid, or viscous.

2. The edible composition of claim 1, wherein the melded interface forms a moisture-retaining barrier layer.

3. The edible composition of claim 2, wherein the moisture-retaining barrier layer retains moisture content of the edible substance.

4. The edible composition of claim 3, wherein the first edible polymer membrane or the second edible polymer membrane has a moisture content of about 85%.

5. The edible composition of claim 4, wherein the first edible polymer membrane or the second edible polymer membrane forms a moisture barrier, wherein the first edible polymer membrane or the second edible polymer membrane is substantially insoluble in water or other aqueous solution.

6. The edible composition of claim 1, further comprising a separate and distinct edible barrier layer between the first edible polymer membrane and the second edible polymer membrane.

7. The edible composition of claim 1, wherein, the edible substance comprises at least one of a liquid, powder, a gel, a foam, a solid, and combinations thereof.

8. The edible composition of claim 1, wherein the first edible polymer membrane and the second edible polymer membrane each comprise a hydrocolloid selected from the group consisting of an alginate, an agar, a starch, a gelatin, carrageenan, xanthan gum, gellan gum, galactomannan, gum arabic, a pectin, a milk protein, a cellulosic, a carboxymethylcellulosic, a methylcellulosic, gum tragacanth and karaya, xyloglucan, curdlan, a cereal $\beta$-glucan, soluble soybean polysaccharide, a bacterial cellulose, a microcrystalline cellulose, chitosan, inulin, an emulsifying polymer, konjac mannan/konjac glucomannan, a seed gum, and pullulan.

9. The edible composition of claim 1, wherein the edible substance is ice cream, frozen yogurt or gelato.

10. The edible composition of claim 1, wherein the first edible polymer membrane, the second edible polymer membrane and/or the melded interface contain particles.

* * * * *